(12) United States Patent
Zhong et al.

(10) Patent No.: US 8,273,901 B2
(45) Date of Patent: Sep. 25, 2012

(54) PROCESS OF FORMING A PYRROLE COMPOUND

(75) Inventors: Guofu Zhong, Singapore (SG); Bin Tan, Singapore (SG); Zugui Shi, Singapore (SG); Pei Juan Chua, Singapore (SG)

(73) Assignee: Nanyang Technical University, Singapore (SG)

( * ) Notice: Subject to any disclaimer, the term of this patent is extended or adjusted under 35 U.S.C. 154(b) by 70 days.

(21) Appl. No.: 12/782,708

(22) Filed: May 18, 2010

(65) Prior Publication Data

US 2011/0124881 A1     May 26, 2011

Related U.S. Application Data

(60) Provisional application No. 61/179,556, filed on May 19, 2009, provisional application No. 61/292,990, filed on Jan. 7, 2010.

(51) Int. Cl.
*C07D 207/30*     (2006.01)
(52) U.S. Cl. .................................................. 548/530
(58) Field of Classification Search ................... 548/530
See application file for complete search history.

(56) References Cited

OTHER PUBLICATIONS

Organic Chemistry Portal: Synthesis of pyrroles, [online], [retrieved on Oct. 24, 2011]. Retrieved from the Internet: <URL: http://www.organic-chemistry.org/synthesis/heterocycles/pyrroles.shtm >.*
Paine et al. (J. Org. Chem., 1987, 52, 3986-3993).*
Elghamry (Synthetic Comm., 32(6), 2002, 897-902).*
Chiba et al. (Org. Lett., 2008, 10, 313-316).*
Paine et al. (J. Org. Chem. 1985, 50, 5598-5604).*
Attanasi et al., J. Org. Chem. (2002) 67, 8178.
Baciocchi et al., J. Org. Chem. (1992) 57, 2486.
Balme, G., Angew. Chem. Int. Ed. (2004) 43, 6238.
Barbas III, Angew. Chem. Int. Ed. (2008) 47, 42-47.
Binder, J.T., & Kirsch, S.F., Org. Lett. (2006) 8, 2151.
Blackmond et al., Angew. Chem. Int. Ed. (2007) 46, 3798.
Bullington et al., J. Org. Chem. (2002) 67, 9439.
Dhawan, R., & Arndtsen, B.A., J. Am. Chem. Soc. (2004) 126, 468.
Enders et al., Angew. Chem. Int. Ed. (2007) 46, 1570.
Gorin et al., J. Am. Chem. Soc. (2005) 127, 11260.
Hayashi, Y., Angew. Chem. Int. Ed. (2006) 45, 8103.
Hekmatshoar, Heteroatom Chemistry (2008) 19, 100-103.
Kim et al., Angew. Chem. Int. Ed. (2003) 42, 98.
Narayan et al., Angew. Chem. Int. Ed. (2005) 44, 3275.
Palomo et al., Angew.Chem. Int. Ed. (2007) 46, 8431-8435.
Ramón, D.J., & Yus, M., Angew. Chem. Int. Ed. (2005) 44, 1602).
Shindo et al., Org. Lett. (2007) 9, 1963.
St. Cyr, D.J., Am. Chem. Soc.(2007) 129, 12366.
St. Cyr, D.J., et al., Org. Lett. (2007) 9, 449.
Syper, L., Tetrahedron Lett. (1966) 7, 4493.
Tan et al., Angew. Chem. Int. Ed. (2009) 48, 758-761.
Wang et al., Adv. Synth. Catal. (2008) 350, 1830).
Yamamoto et al., J. Am. Chem. Soc. (2005) 127, 10804.

* cited by examiner

*Primary Examiner* — Robert Havlin
(74) *Attorney, Agent, or Firm* — Sam K. Tahmassebi; TechLaw LLP

(57) ABSTRACT

Disclosed is a process of forming a pyrrole compound. The process comprises contacting an α-carbonyl oxime compound 1

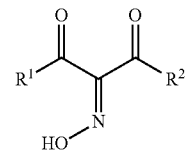

(1)

and an α,β-unsaturated aldehyde 2

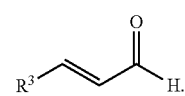

(2)

$R^1$ and $R^2$ in compound 1 are independently selected from the group consisting of H, a silyl-group, an aliphatic group, an alicyclic group, an aromatic group, an arylaliphatic group, and an arylalicyclic group. The aliphatic, alicyclic, aromatic, arylaliphatic, and arylalicyclic groups comprise 0 to about 3 heteroatoms selected from the group N, O, S, Se and Si. $R^3$ in aldehyde 2 is selected from the group consisting of H, a silyl-group, an aliphatic group, an alicyclic group, an aromatic group, an arylaliphatic group, and an arylalicyclic group. The aliphatic, alicyclic, aromatic, arylaliphatic, and arylalicyclic groups comprise 0 to about 3 heteroatoms selected from the group N, O, S, Se and Si. The α-carbonyl oxime compound 1 an the α,β-unsaturated aldehyde 2 are contacted in a suitable solvent in the presence of a secondary amine. The compounds are contacted for a sufficient period of time to allow the formation of an N-hydroxypyrrole compound 3

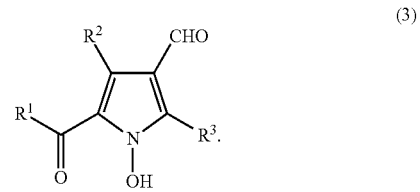

(3)

13 Claims, 65 Drawing Sheets

| Entry | Catalyst | Solvent | Time [h] | Yield [%][a] |
|---|---|---|---|---|
| 1 | I | toluene | 10 | 58 |
| 2 | II | toluene | 12 | 61 |
| 3 | III | toluene | 12 | 63 |
| 4 | IV | toluene | 10 | 82 |
| 5 | V | toluene | 18 | 66 |
| 6 | VI | toluene | 18 | 67 |
| 7 | VII | toluene | 18 | 83 |
| 8 | VII | CH$_2$Cl$_2$ | 24 | 79 |
| 9 | VII | Et$_2$O | 24 | 33 |
| 10 | VII | DMSO | 24 | 0 |

| Entry | Oxime 1 R¹ | R² | Enal 2 R³ | Time [h] | Yield of 3 [%][a] |
|---|---|---|---|---|---|
| 1 | EtO | Me | nPr | 18 | 3a, 83 |
| 2 | EtO | Me | Me | 18 | 3b, 83 |
| 3 | EtO | Me | Et | 18 | 3c, 81 |
| 4 | EtO | Me | Me(CH$_2$)$_4$ | 18 | 3d, 76 |
| 5 | EtO | Me | PhCH$_2$CH$_2$ | 24 | 3e, 82 |
| 6 | EtO | Me | BnOCH$_2$CH$_2$CH$_2$ | 24 | 3f, 78 |
| 7 | MeO | Me | Me | 18 | 3g, 73 |
| 8 | tBuO | Me | Me | 24 | 3h, 72 |
| 9 | BnO | Me | Me | 18 | 3i, 75 |
| 10 | MeO | Et | Me | 24 | 3j, 77 |
| 11 | MeO | Et | nPr | 24 | 3k, 67 |
| 12 | MeO | Et | Et | 24 | 3l, 79 |
| 13 | MeO | Et | Me(CH$_2$)$_4$ | 24 | 3m, 66 |
| 14 | Me | Me | Me | 18 | 3n, 79 |
| 15 | Me | Me | nPr | 18 | 3o, 81 |
| 16 | Me | Me | Et | 18 | 3p, 83 |
| 17 | Me | Me | Me(CH$_2$)$_4$ | 18 | 3q, 77 |
| 18 | Me | Me | PhCH$_2$CH$_2$ | 18 | 3r, 82 |
| 19 | Me | Me | BnOCH$_2$CH$_2$CH$_2$ | 18 | 3s, 73 |
| 20 | Me | Me | BocNHCH$_2$CH$_2$ | 24 | 3t, 61 |
| 21[b] | Ph | Ph | Me | 48 | 3u, 58 |

Fig. 5A
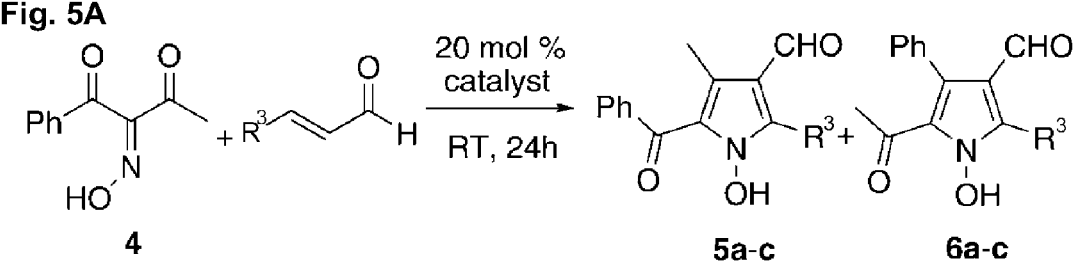
Fig. 5B
| Entry | R³ | Cat | Solvent | Yield of 5 [%][a] | Yield of 6 [%][a] |
|---|---|---|---|---|---|
| 1 | Me | VII | toluene | 5a, 76 | 6a, trace[b] |
| 2 | nPr | VII | toluene | 5b,(62) | 6b, 13 |
| 3 | Me(CH₂)₄ | VII | toluene | 5c, 60 | 6c, 16 |
| 4 | Me(CH₂)₄ | VII | CH₂Cl₂ | 5c, 64 | 6c, 13 |
| 5 | Me(CH₂)₄ | IV | toluene | 5c, 71 | 6c, trace |
| 6 | Me(CH₂)₄ | V | toluene | 5c, 61 | 6c, trace |
| 7 | nPr | IV | toluene | 5b, 78 | 6b, trace |
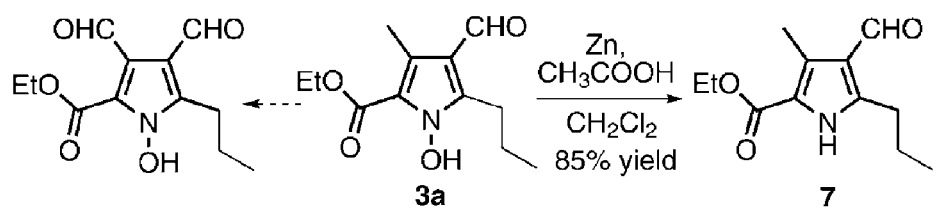
Fig. 6

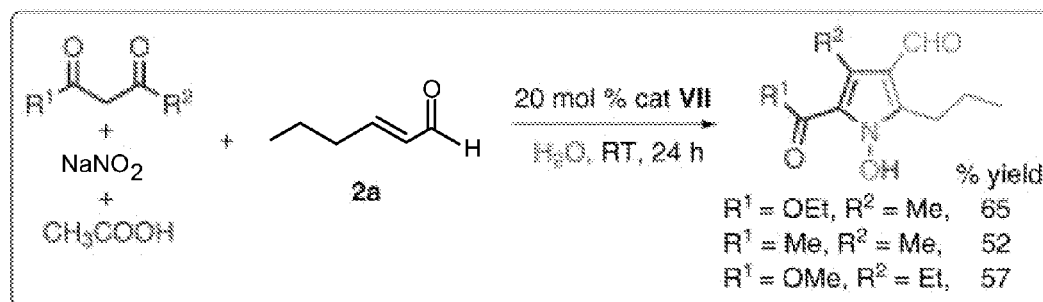
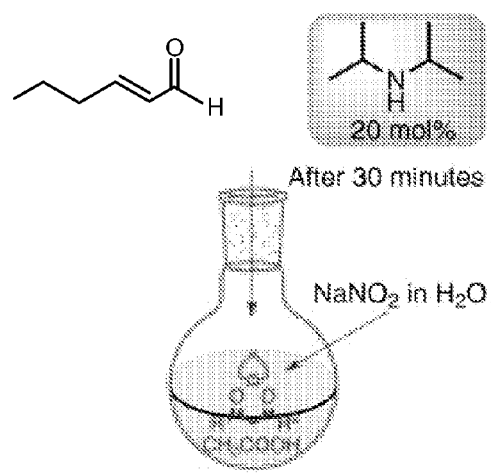
Fig. 8
Fig. 9A
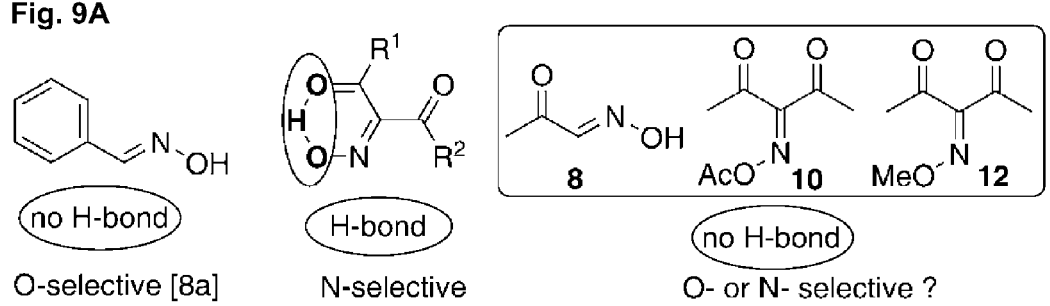

PROCESS OF FORMING A PYRROLE COMPOUND

CROSS-REFERENCE TO RELATED APPLICATIONS

This application makes reference to and claims the benefit of priority of an application for "Unusual Domino Michael/Aldol Condensation Reactions Employing Oximes As N-Selective Nucleophiles: Synthesis Of N-Hydroxypyrroles" filed on May 19, 2009 with the United States Patent and Trademark Office, and there duly assigned Ser. No. 61/179,556. Further, this application makes reference to and claims the benefit of priority of an application for a "Process of Forming a Pyrrole Compound" filed on Jan. 7, 2010 with the United States Patent and Trademark Office, and there duly assigned Ser. No. 61/292,990. The contents of said applications filed on May 19, 2009 and on Jan. 7, 2010 are incorporated herein by reference for all purposes in their entirety.

FIELD OF THE INVENTION

The present invention provides a process of forming a pyrrole compound. The process includes the formation of a N-hydroxypyrrole compound in a cyclization reaction based on a domino Michael/Aldol condensation.

BACKGROUND OF THE INVENTION

As one of the most important classes of heterocycles, pyrroles are not only important building blocks in the synthesis of natural products, but also key structural units in compounds with interesting biological activities. Pyrroles have also found broad application in materials chemistry. Accordingly, substantial attention has been paid to develop efficient methods for their synthesis. One of the common approaches to pyrrole synthesis is the Paal-Knorr reaction, in which 1,4-dicarbonyl compounds are converted into pyrroles by acid-mediated dehydrative cyclization. However, this approach is usually subject to significant limitations in terms of substituents introduced, substitution patterns, or regioselectivities.

Although several novel synthetic strategies have been described in recent years, [for metal-catalyzed pyrrole syntheses see e.g. J. T. Kim, J T, et al., *Angew. Chem. Int. Ed.* (2003) 42, 98; Balme, G, *Angew. Chem. Int. Ed.* (2004) 43, 6238; St. Cyr, D J, et al., *Org. Lett.* (2007) 9, 449; Binder, J T, & Kirsch, S F, *Org. Lett.* (2006) 8, 2151; Gorin, D J, et al., *J. Am. Chem. Soc.* (2005) 127, 11260; Dhawan, R, & Arndtsen, B A, *J. Am. Chem. Soc.* (2004) 126, 468; Yamamoto, Y, et al., *J. Am. Chem. Soc.* (2005) 127, 10804; for metal-free pyrrole syntheses see e.g. Bullington, J L, et al., *J. Org. Chem.* (2002) 67, 9439; Attanasi, O A, et al., *J. Org. Chem.* (2002) 67, 8178; Shindo, M, et al., *Org. Lett.* (2007) 9, 1963; St. Cyr, D J, *Am. Chem. Soc.* (2007) 129, 12366] a general facile and regioselective approach to generate pyrroles with a wide functional group tolerance from readily available precursors is still lacking.

Accordingly, it is an object of the present invention to provide a process that allows a simple formation of pyrrole compounds under mild conditions.

SUMMARY OF THE INVENTION

The invention relates to a process of forming a pyrrole compound. The process includes providing an α-carbonyl oxime compound of general formula (1)

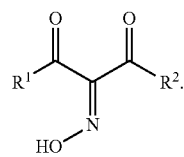

(1)

In formula (1) $R^1$ and $R^2$ are independently from one another selected from the group consisting of H, a silyl-group, an aliphatic group, an alicyclic group, an aromatic group, an arylaliphatic group and an arylalicyclic group. The aliphatic, alicyclic, aromatic, arylaliphatic and arylalicyclic groups of $R^1$ and $R^2$ may include 0 to about 3 heteroatoms. These heteroatoms are selected from the group N, O, S, Se and Si. The aliphatic, alicyclic, aromatic, arylaliphatic and arylalicyclic groups of the groups —$OR^{10}$ and —$NR^{10}$ may likewise include 0 to about 3 heteroatoms. These heteroatoms are selected from the group N, O, S, Se and Si. The process also includes providing an α,β-unsaturated aldehyde of the general formula (2)

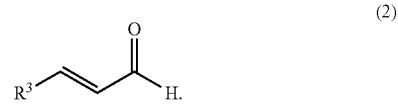

(2)

In formula (2) $R^3$ is one of H, a silyl-group, an aliphatic group, an alicyclic group, an aromatic group, an arylaliphatic group, and an arylalicyclic group. In some embodiments aromatic groups are excluded. In some embodiments arylaliphatic groups and arylalicyclic groups are excluded in which an aromatic ring is directly linked to the α,β-unsaturated bond of the α,β-unsaturated aldehyde (2). The aliphatic, alicyclic, aromatic, arylaliphatic, and arylalicyclic groups may include 0 to about 3 heteroatoms. These heteroatoms are selected from the group N, O, S, Se and Si. The process also involves providing a secondary amine. The process further includes contacting the α-carbonyl oxime compound of general formula (1) and the α,β-unsaturated aldehyde of the general formula (2) in a suitable solvent. The α-carbonyl oxime compound and the α,β-unsaturated aldehyde are contacted in the presence of the secondary amine. The α-carbonyl oxime compound and the α,β-unsaturated aldehyde are contacted in the presence of the secondary amine for a sufficient period of time to allow the formation of an N-hydroxypyrrole compound of the general formula (3):

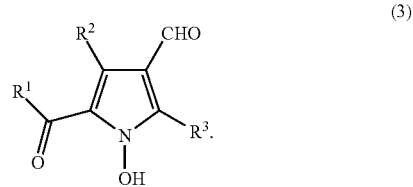

(3)

In formula (3) $R^1$ to $R^3$ are as defined above (see formulas (1) and (2)).

In some embodiments the secondary amine is of the general formula (XX)

(XX)

In formula (XX) $R^{20}$ and $R^{21}$ are independently from one another selected from the group consisting of an aliphatic group, an alicyclic group, an aromatic group, an arylaliphatic group and an arylalicyclic group. In some embodiments one of $R^{20}$ and $R^{21}$ defines an aliphatic, aromatic or arylaliphatic bridge that is linked to the respective other moiety of $R^{20}$ and $R^{21}$. Accordingly, $R^{20}$ and $R^{21}$ may define one common cyclic structure. The aliphatic, alicyclic, aromatic, arylaliphatic, and arylalicyclic groups of $R^{20}$ and $R^{21}$ may include 0 to about 3 heteroatoms. These heteroatoms are selected from the group N, O, S, Se and Si.

In some embodiments the process is carried out with the proviso that DMSO and DMF are excluded as solvents.

BRIEF DESCRIPTION OF THE DRAWINGS

The invention will be better understood with reference to the detailed description when considered in conjunction with the non-limiting examples and the accompanying drawings.

FIG. 5A is a scheme illustrating the regioselectivity of the domino reaction of the process of the invention. FIG. 5B shows the regioselectivity in the domino reaction of diketone oximes 4 and α,β-unsaturated aldehydes. Reactions were carried out using compound 4 (0.3 mmol, 1.0 equivalents) and different aldehydes (0.6 mmol, 2.0 equivalents) in the presence of the indicated amine (20 mol %) as a catalyst in the indicated solvent (1.0 mL) at room temperature. The reaction time was 24 hours. [a]: Yield of isolated product. [b]: Almost undetectable.

FIG. 6 shows the further transformation of compound 3a into 1H-pyrrole 7.

FIG. 8 illustrates a one-pot synthesis of N-hydroxypyrrole according to an embodiment of the process of the invention in water.

FIG. 9A illustrates a preliminary conjecture of the reaction mechanism: the effect of intramolecular hydrogen bonding.

FIG. 10A depicts a $^1$H NMR spectrum and FIG. 10B a $^{13}$C NMR spectrum of compound 3a.

FIG. 30 depicts $^1$H NMR (A) and $^{13}$C NMR (B) spectra of compound 5a.

DETAILED DESCRIPTION OF THE INVENTION

Figure 1A:
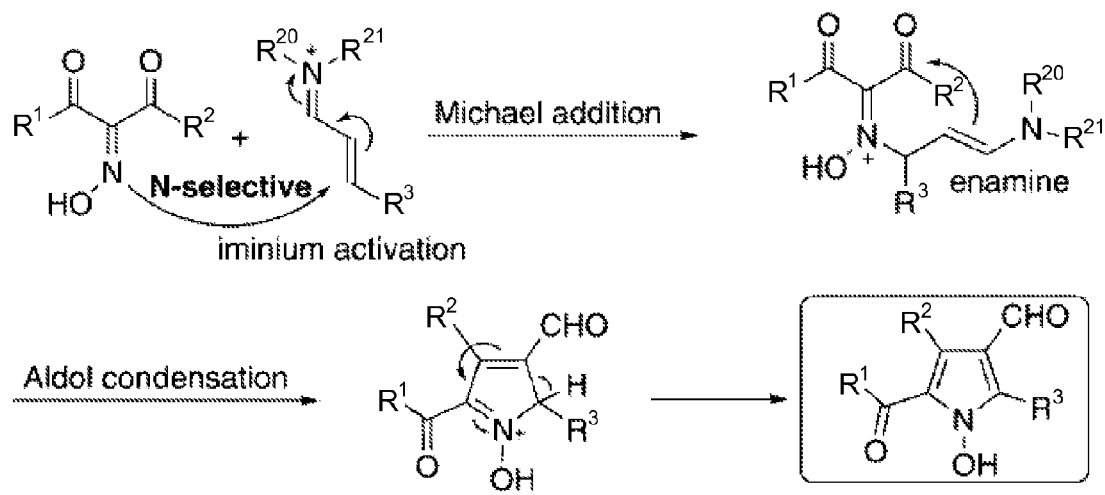
FIG. 1A depicts a proposed reaction mechanism of the domino Michael addition/aldol condensation reaction by iminium activation that is thought to be involved in the process of the invention.

The invention provides a process that involves forming a N-hydroxypyrrole compound. In a simple step under mild conditions the N-hydroxypyrrole compound can be further converted to a 1H pyrrole compound (e.g. FIG. 6). Compounds with a functionalized pyrrole ring system are an important class for instance in the pharmaceutical field and in polymer technology.

The N-hydroxypyrrole compound is of the general formula (3):

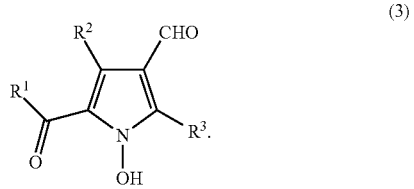

(3)

In formula (3) $R^1$ to $R^3$ may, independently from one another, be one of H, a silyl-group, an aliphatic group, an alicyclic group, an aromatic group, an arylaliphatic group, an arylaliphatic group and an arylalicyclic group. In some embodiments $R^3$ is a group other than an aromatic group. The aliphatic, alicyclic, aromatic, arylaliphatic, and arylalicyclic groups may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The respective aliphatic, alicyclic, aromatic or arylaliphatic moiety of $R^1$, $R^2$ or $R^3$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si. Furthermore, $R^1$ and $R^2$ may be independently selected from the group —$OR^{10}$ and the group —$NR^{10}$. In these embodiments each respective moiety $R^{10}$, where present, is independently selected from H, a silyl-group, an aliphatic group, an alicyclic group, an aromatic group, an arylaliphatic group, and an arylalicyclic group. The aliphatic, alicyclic, aromatic, arylaliphatic, and arylalicyclic groups may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The respective aliphatic, alicyclic, aromatic or arylaliphatic moiety of $R^{10}$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si.

A respective silyl group may be represented as

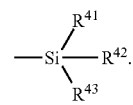

Each of $R^{41}$, $R^{42}$ and $R^{43}$ may be an independently selected aliphatic, alicyclic, aromatic, arylaliphatic or arylalicyclic group. A respective aliphatic, alicyclic, aromatic or arylaliphatic group may have a main chain of about 1 to about 30 carbon atoms, such as 2 to about 30 carbon atoms or 3 to about 30 carbon atoms, including about 1 to about 25 carbon atoms, about 1 to about 20 carbon atoms, about 2 to about 20 carbon atoms, about 1 to about 15 carbon atoms, about 2 to about 15 carbon atoms, about 3 to about 15 carbon atoms, about 1 to about 10 carbon atoms, about 2 to about 10 carbon atoms or about 3 to about 10 carbon atoms, such as 1, 2, 3, 4, 5, 6, 7, 8, 9, 10, 11, 12, 13, 14, 15, 16, 17, 18, 19, 20, 21, 22, 23, 24 or 25 carbon atoms. The main chain of the aliphatic, alicyclic, aromatic or arylaliphatic moiety may further have 0 to about 6, e.g. 0 to about 5 or 0 to about 4, such as 0, 1, 2, 3, 4, 5 or 6 heteroatoms. A respective heteroatom may be one of N, O, S, Se and Si.

Accordingly, in some embodiments the proton (H), the silyl-group, the aliphatic group, the alicyclic group, the aromatic group or the arylaliphatic group of $R^1$ and $R^2$ may be linked to the general structure depicted above via a nitrogen atom or an oxygen atom. In some of these embodiments the N-hydroxypyrrole compound of the general formula (3) may for example be depicted as:

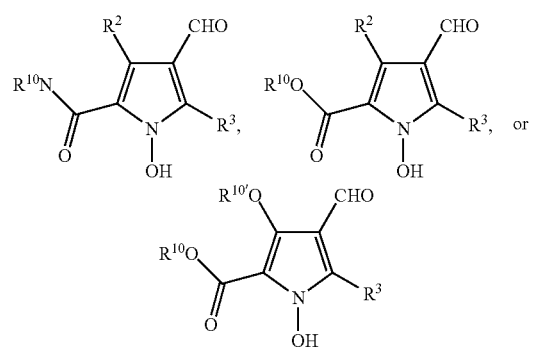

In these depicted N-hydroxypyrrole compounds $R^{10}$ and $R^{10'}$ are as defined above for $R^{10}$.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

The term "alicyclic" may also be referred to as "cycloaliphatic" and means, unless stated otherwise, a non-aromatic cyclic moiety (e.g. hydrocarbon moiety), which may be saturated or mono-or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the term "aromatic" means an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl—, [10]annulenyl-(1,3,5,7,9 -cyclodecapentaenyl—), [12]annulenyl—, [8]annulenyl—, phenalene (peri-naphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moietie may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-, (azacyclodecapentaenyl-), diazecinyl-, azacyclododeca-1,3,5,7, 9,11-hexaene-5,9-diyl-, azozinyl-, diazocinyl-, benzazocinyl-, azecinyl-, azaundecinyl-, thia[11]annulenyl-, oxacyclotrideca-2,4,6,8, 10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited to, 1-ethyl-naphthalene, 1,1'-methylenebisbenzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethyl-phenyl)ethyl]-4-ethyl-quinazoline or 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents may be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzene-sulfonyl, nitrobenzenesulfonyl, and methanesulfonyl.

The process of the invention is generally carried out in the liquid phase. Any solvent may be used, as long as the compounds used dissolve therein sufficiently. Solvents used may be polar or non-polar liquids, including aprotic non-polar liquids (see also below).

A polar solvent, such as a polar protic solvent, can be a solvent that has, for example, a hydrogen atom bound to an oxygen as in a hydroxyl group or a nitrogen as in an amine group. More generally, any molecular solvent which contains dissociable $H^+$, such as hydrogen fluoride, is called a protic solvent. The molecules of such solvents can donate an $H^+$ (proton). Examples of polar protic solvents include, but are not limited to, water, methanol, ethanol or acetic acid. In one embodiment of the present invention water may be used.

In the process of the invention an α-carbonyl oxime compound of general formula (1) is provided:

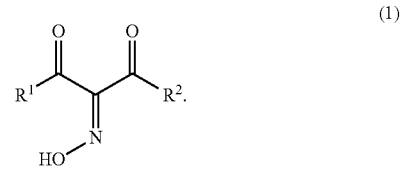

(1)

In formula (1) moieties $R^1$ and $R^2$ are as defined above. The α-carbonyl oxime compound may be formed according to any procedure known in the art. In some embodiments it is formed from a 1,3-dicarbonyl compound (20)

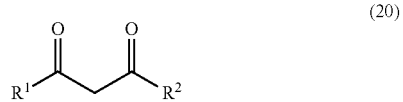

(20)

and an inorganic nitrite, i.e. generally a metal nitrite, in a carboxylic acid solvent. Illustrative examples of an inorganic nitrite are sodium nitrite, potassium nitrite, lithium nitrite, zinc nitrite, iron (II) nitrite or nickel nitrite. Any carboxylic acid may be used as the respective solvent. Illustrative examples include acetic acid, propionic acid, butyric acid, valeric acid, caproic acid, heptanoic acid (enanthic acid), caprylic acid, pelargonic acid, capric acid, myristic acid, lauric acid, palmitic acid, myristoleic acid, palmitoleic acid, benzoic acid, naphthylic acid, adipic acid, fumaric acid, maleic acid, glutaric acid or citric acid.

In some embodiments the α-carbonyl oxime compound is formed in situ as described above. The 1,3-dicarbonyl compound may be reacted with the inorganic nitrite and subsequently the α,β-unsaturated aldehyde and the secondary amine be added. The α,β-unsaturated aldehyde may for example be added to a solution, in which the 1,3-dicarbonyl compound has been contacted with an inorganic nitrite, typically after a period of time sufficient for the formation of an α-carbonyl oxime compound. In some embodiments the secondary amine is added subsequently. In some embodiments the secondary amine is used as the solvent and already present during the formation of the α-carbonyl oxime from an 1,3-dicarbonyl compound. The α,β-unsaturated aldehyde may in some embodiments be added to a solution of the α-carbonyl oxime compound, to which the secondary amine has been added, for example after the formation of the α-carbonyl oxime from an 1,3-dicarbonyl compound. The α,β-unsaturated aldehyde may in some embodiments be added to a solution of the α-carbonyl oxime compound before the secondary amine is being added. In some embodiments the α-carbonyl oxime compound is synthesized and subsequently isolated before being reacted with the α,β-unsaturated aldehyde and the secondary amine.

In the process of the invention the α-carbonyl oxime compound of general formula (1) is reacted with an α,β-unsaturated aldehyde of the general formula (2)

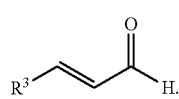

(2)

In formula (2) moiety $R^3$ is as defined above. The α-carbonyl oxime compound and the α,β-unsaturated aldehyde are contacted with each other. They are brought into such close proximity that molecules of these two reactants are able to undergo a chemical reaction with each other. The two reactants are generally added to the same solvent. Typically the two reactants dissolve in the solvent. The two reactants may be brought in contact by allowing diffusion to occur or by means of agitation, such as stifling. The reaction of the α-carbonyl oxime compound of general formula (1) and α,β-unsaturated aldehyde of general formula (2) is typically allowed to start by contacting oxime (1) and aldehyde (2) in the presence of a secondary amine. Accordingly, the a secondary amine is allowed to contact the α,β-unsaturated aldehyde of general formula (2), typically in a solvent.

The aldehyde (2) and the α-carbonyl oxime compound may be provided in any desired ratio. As Michael reactions as such are already well known in the art, the skilled artisan will generally decide on a predefined ratio based on the expected reactivity of the reactants. This predefined ratio may then be adjusted in optimization experiments. In some embodiments the aldehyde (2) and the α-carbonyl oxime compound may be provided in similar, including at least essentially equal amounts. In some embodiments the aldehyde may be provided in an excess relative to the α-carbonyl oxime compound, such as an excess in the range from about 1.01- to about 7-fold, from about 1.1- to about 5-fold, from about 1.1- to about 3-fold or from about 1.1- to about 2-fold, including e.g. about 1.5-fold or about 2.5-fold.

In the process of the invention the reaction between the α-carbonyl oxime compound (1) and the aldehyde (2) is allowed to proceed in the presence of a secondary amine. Any secondary amine may be used that is capable of forming an imine with a selected aldehyde (cf. below).

In some embodiments the secondary amine is of the general formula (XX)

(XX)

In formula (XX) moieties $R^{20}$ and $R^{21}$ are independently from one another one of an aliphatic group, an alicyclic group, an aromatic group, an arylaliphatic group and an arylalicyclic group. The aliphatic, alicyclic, aromatic, arylaliphatic, and arylalicyclic groups may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The respective aliphatic, alicyclic, aromatic or arylaliphatic moiety of $R^1$, $R^2$ or $R^3$ may have 0 to about 8 heteroatoms, such as 0 to about 7 or 0 to about 6, e.g. 0 to about 5 or 0 to about 4, such as 0, 1, 2, 3, 4, 5 or 6 heteroatoms. A respective heteroatom may be one of N, O, S, Se and Si.

In some embodiments the secondary amine is of the general formula (XXI)

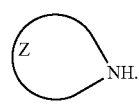

(XXI)

In formula (XXI) Z is a 4- to 20-membered bridge, such as a 4- to 18-membered bridge, including a 20-membered bridge, a 19-membered bridge, an 18-membered bridge, a 17-membered bridge, a 16-membered bridge, a 15-membered bridge, a 14-membered bridge, a 13-membered bridge, a 12-membered bridge, an 11-membered bridge, a 10-membered bridge, a 9-membered bridge, an 8-membered bridge, a 7-membered bridge, a 6-membered bridge, a 5-membered bridge or a 4-membered bridge. The bridge Z may include saturated and unsaturated carbon-carbon bonds, including double and triple bonds. The bridge Z may be an aliphatic bridge, an aromatic bridge or an arylaliphatic bridge. The bridge may include 0 to about 10 heteroatoms. The heteroatom(s) may for example be Si, N, O, S or Se.

Figure 1B:
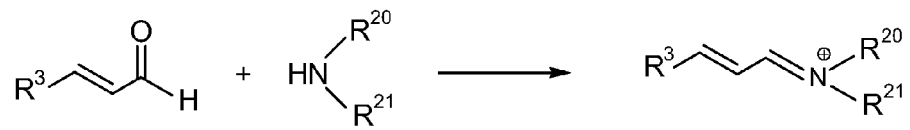
FIG. 1B illustrates the formation of an imine from the α,β-unsaturated aldehyde of the general formula (2) during the process of the invention.
Figure 2:
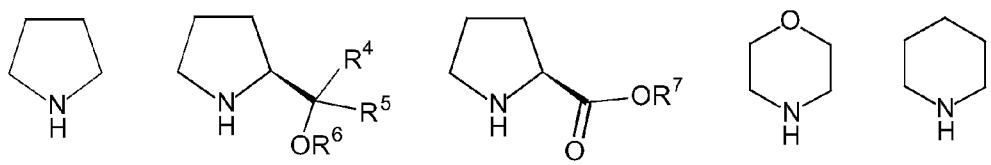
FIG. 2 shows illustrative examples of cyclic secondary amines that may be used in the process of the invention. $R^4$ to $R^7$ may be one of H, a silyl-group, an aliphatic group, an alicyclic group, an aromatic group, an arylaliphatic group, and an arylalicyclic group. The aliphatic, alicyclic, aromatic, arylaliphatic, and arylalicyclic groups may include 0 to about 4, including 1, 2, 3 or 4 heteroatoms selected from the group N, O, S, Se and Si. "n" is an integer selected in the range from 0 to about 6, such as 1, 2, 3, 4, 5 or 6 (cf. also Palomo, C., et al., *Angew. Chem. Int. Ed.* (2007) 46, 8431-8435).
Figure 2:
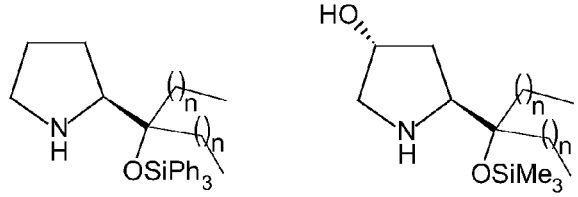

Without being bound by theory, it is believed that the secondary amine used in the process of the invention undergoes a condensation reaction with the α,β-unsaturated aldehyde (FIG. 1B). Thereby an iminium ion is thought to be formed, as depicted in FIG. 1A and FIG. 1B. This iminium ion is thought to have a lower LUMO energy and thus higher reactivity when compared to the aldehyde used (cf. e.g. Melchiorre, P, et al., *Angew. Chem. Int. Ed.* (2008) 6138-6171). The theoretic model of the reaction mechanism of the formation of imines is well known in the art. As also further explained below, the amine is thereby thought to act as a catalyst.

In the process of the invention the secondary amine may be used in any desired amount relative to the amounts of aldehyde 2 and α-carbonyl oxime compound 1. The amine quantity is not a critical feature of the process and can vary over a wide range. In some embodiments the secondary amine is used in an amount that is about equal or less than the amount of aldehyde used. In some embodiments the secondary amine is used in a catalytic amount. Unless otherwise noted, the term "catalytic amount," as used herein, includes that amount of the secondary amine that is sufficient for a reaction of the process of the invention to occur. Accordingly, the quantity that constitutes a catalytic amount is any quantity that serves to allow or to increase the rate of reaction, with larger quantities typically providing a greater increase. The quantity used in any particular application will be determined in large part by the individual needs of the manufacturing facility. Factors which enter into such a determination include the catalyst cost, recovery costs, desired reaction time, and system capacity. It will be most convenient to use an amount of amine in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the aldehyde, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.005, about 0.02 or about 0.04 equivalents of the α-carbonyl oxime compound 1.

In some embodiments a reaction mixture is formed, thereby allowing the reaction between the α-carbonyl oxime compound 1 and the α,β-unsaturated aldehyde 2 to occur. In forming the reaction mixture any suitable solvent may be used. In some embodiments a non-polar or an aprotic polar solvent is used. The polarity of a molecule, including a solvent molecule, is reflected by its dielectric constant or its dipole moment. Polar molecules are typically further classified into protic and non-protic (or aprotic) molecules. A fluid, e.g. a liquid, that contains to a large extent polar protic molecules may therefore be termed a polar protic fluid. A fluid, e.g. a liquid, that contains to a large extent polar non-protic molecules may be termed a polar non-protic fluid. Protic molecules contain a hydrogen atom which may be an acidic hydrogen when the molecule is dissolved for instance in water or an alcohol. Aprotic molecules do not contain such hydrogen atoms.

Examples of a non-polar solvent include, but are not limited to mineral oil, hexane, heptane, cyclohexane, benzene, toluene, dichloromethane, chloroform, carbon tetrachloride, carbon disulfide, dioxane, diethyl ether, or diisopropylether and a non-polar ionic liquid. Examples of a non-polar ionic liquid include, but are not limited to, 1-ethyl-3-methylimidazolium bis [(trifluoro methyl) sulfonyl]amide bis (triflyl)amide, 1-ethyl-3-methylimidazolium bis[(trifluoromethyl) sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis-(trifluoromethylsulfonyl) imide, trihexyl(tetradecyl)phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris(pentafluoroethyl)trifluorophosphate, trihexyl(tetradecyl)phosphornium, N"-ethyl-N,N,N', N'-tetramethylguanidinium, 1-butyl-1-methyl pyrrolidinium tris(pentafluoroethyl) trifluorophosphate, 1-butyl-1-methyl pyrrolidinium bis(trifluoromethylsulfonyl) imide, 1-butyl-3-methyl imidazolium hexafluorophosphate, 1-ethyl-3-methylimidazolium bis(trifluoromethylsulfonyl)imide and 1-n-butyl-3-methylimidazolium. The polarity of ionic liquids is known to be largely determined by the associated anion. While e.g. halides, pseudohalides, $BF_4^-$, methyl sulphate, $NO_3^-$, or $ClO_4^-$ are polar liquids, hexafluorophosphates, $AsF_6^-$, bis(perfluoroalkyl)imides, and $[C_4F_6SO_3]^-$ are non-polar liquids.

Examples of dipolar aprotic liquids are methyl ethyl ketone, chloroform, tetrahydrofuran, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide. In some embodiments dimethylsulfoxide and dimethylformamide are excluded as solvents. A dipolar aprotic liquid may also be an ionic liquid. Examples of a polar ionic liquid include, but are not limited to, 1-ethyl-3-methylimidazolium dicyanamide, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoroethyl) phosphinate, 1-butyl-3-methylimidazolium tetrakis (3,5-bis (trifluoro methylphenyl)borate, tetrabutylammonium bis(trifluoromethyl)imide, ethyl-3-methylimidazolium trifluoromethanesulfonate, 1-butyl-3-methylimidazolium methylsulfate, 1-n-butyl-3-methylimidazolium ([bmim]) octylsulfate, and 1-n-butyl-3-methylimidazolium tetrafluoroborate.

The reaction mixture is formed by combining the aldehyde 2, the α-carbonyl oxime compound 1 and the secondary amine in the selected solvent. Typically the three compounds, the aldehyde 2, the α-carbonyl oxime compound 1 and the secondary amine are dissolved in the solvent. The three compounds may be added to the solvent successively, in any desired order, or concurrently. In some embodiments the α-carbonyl oxime compound 1 and the aldehyde 2 are added to the solvent first. Subsequently the secondary amine is added, thereby allowing the reaction of the process of the invention to start.

The present inventors have surprisingly found that a polar protic solvent, including water, can be used in the process of the present invention. A protic solvent is a liquid that has, for example, a hydrogen atom bound to an oxygen as in a hydroxyl group or a nitrogen as in an amine group. More generally, any molecular liquid which contains dissociable $H^+$, such as hydrogen fluoride, is called a protic liquid. The molecules of such liquid can donate a $H^+$ (proton). Examples of a polar protic liquid may be, but are not limited to, water, an alcohol such as methanol, ethanol, propanol, isopropanol, an amine such as ethylenediamine, diethylenetriamine, piperidin, pyrrolidin, morpholine, aniline, pyrimidine or a carboxylic acid such as acetic acid. In some embodiments the reaction of the process of the invention is carried out in an aqueous liquid, including an aqueous solution.

The reaction may be allowed to proceed at any desired temperature, such as a temperature in the range from −70° C. to about +70° C., depending on the boiling point of the solvent selected. The temperature may, for instance, be selected in the range from about −20° C. to about +40° C., from about −20° C. to about +30° C., from about −20° C. to about +60° C. or in the range from about 0° C. to about +60° C. In one embodiment the reaction is carried out at ambient temperature, e.g. room temperature, which may be about, +25° C., +23° C. or +18° C.

The reaction may be allowed to proceed until no further increase in the amount of N-hydroxypyrrole is detectable. The reaction may also be allowed to proceed for a predetermined period of time. The reaction time may be selected to be in the range from about 4 to about 56 hours, such as about 8 to about 48 hours, such as about 12 hours, about 18 hours, about 22 hours, about 24 hours, about 30 hours, about 36 hours or about 42 hours.

In order that the invention may be readily understood and put into practical effect, particular embodiments will now be described by way of the following non-limiting examples.

EXEMPLARY EMBODIMENTS OF THE INVENTION

General Information

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography was performed using Merck silica gel 60 with freshly distilled solvents. Columns were typically packed as slurry and equilibrated with the appropriate solvent system prior to use.

Proton nuclear magnetic resonance spectra ($^1$H-NMR) were recorded on Bruker AMX 400 spectrophotometer (CDCl$_3$ as solvent). Chemical shifts for $^1$H NMR spectra are reported as δ in units of parts per million (ppm) downfield from SiMe$_4$ (δ 0.0) and relative to the signal of chloroform-d (δ 7.26, singlet). Multiplicities were given as: s (singlet), d (doublet), t (triplet), dd (doublets of doublet) or m (multiplets). Coupling constants are reported as a J value in Hz. Carbon nuclear magnetic resonance spectra ($^{13}$C-NMR) are reported as δ in units of parts per million (ppm) downfield from SiMe$_4$ (δ 0.0) and relative to the signal of chloroform-d (δ 77.0, triplet).

High resolution mass spectrometry (HRMS) was recorded on Finnigan MAT 95×P spectrometer.

Oxime compounds were synthesized from the corresponding 1,3-dicarbonyl compound and sodium nitrite in acetic acid, as described by May & Lash (May, D A, Jr., & Lash, T D, *J. Org. Chem.* (1992) 57, 4820).

EXAMPLE 1

Figures 4A, 4B:
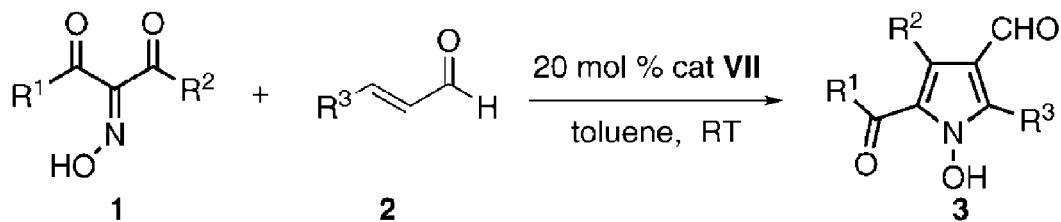
FIG. 4 illustrates a number of examples of the synthesis of N-hydroxypyrroles by the domino Michael addition/aldol condensation reaction. Unless otherwise specified, reactions were carried out using compounds 1 (0.2 mmol, 1.0 equivalents) and 2 (0.5 mmol, 2.5 equivalents) in the presence of amine VII (20 mol %) in toluene (1.0 mL) at room temperature. [a]: Yield of isolated product. [b]: 30 mol % amine was used. Boc=tert-butoxycarbonyl.

Typical Procedure for Pyrrole Synthesis (FIG. 4B, entry 1)

To a solution of oxime compound 1a (0.4 mmol, 1.0 eq) and (E)-hex-2-enal (2a, 1.0 mmol, 2.5 eq) in toluene (2 mL) was added catalyst VII (0.08 mmol, 0.2 eq) at room temperature (23° C.). The resulting mixture was stirred vigorously. After the reaction was completed (monitored by TLC), the mixture was quenched with saturated ammonium chloride, extracted with dichloromethane (3 times), dried over anhydrous Na$_2$SO$_4$ and concentrated under reduced pressure. The product 3a was afforded by flash chromatography over silica gel (EtOAc/Hexane=1:15 to 1:10) in 83% yield.

In the following exemplary data on the reaction of a series of oxime compounds are provided. Following the foregoing protocol products were obtained, isolated and characterized.

Ethyl 4-formyl-1-hydroxy-3-methyl-5-propyl-1H-pyrrole-2-carboxylate (FIG. 4B, entry 1)

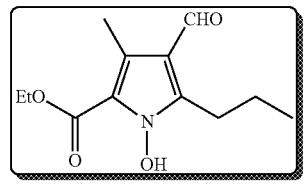

Prepared according to the general procedure to provide the title compound (96% yield).

$^1$H-NMR (400 MHz, CDCl$_3$) δ 12.37 (s, 1H), 9.96 (s, 1H), 4.45 (q, J =7.2 Hz, 2H), 2.96 (t, J=7.2 Hz, 2H), 2.58 (s, 3H), 1.74-1.68 (m, 2H), 1.44 (t, J=7.2 Hz, 3H), 0.99 (t, J=7.2 Hz, 3H).

$^{13}$C-NMR (100 MHz, CDCl$_3$) δ 184.8, 165.5, 137.9, 127.8, 115.1, 112.4, 61.6, 24.7, 21.7, 14.3, 113.7, 10.6.

HRMS (ESI) [M+H]$^+$: calcd for C$_{12}$H$_{18}$NO$_4$, 240.1236, found 240.1232.

Ethyl 4-formyl-1-hydroxy-3,5-dimethyl-1H-pyrrole-2-carboxylate (3b, FIG. 4B, entry 2)

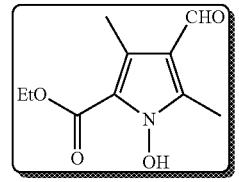

Prepared according to the general procedure described above in 83% yield.

$^1$H-NMR (400 MHz, CDCl$_3$) δ 12.36 (brs, 1H), 9.96 (s, 1H), 4.44 (q, J=7.2 Hz, 2H), 2.56 (s, 3H), 2.53 (s, 3H), 1.44 (t, J=7.2 Hz, 3H).

$^{13}$C-NMR (100 MHz, CDCl$_3$) δ 185.0, 165.4, 133.7, 127.8, 115.3, 112.5, 61.6, 14.3, 10.4, 8.7.

HRMS (ESI) [M+H]⁺: calcd for $C_{10}H_{14}NO_4$, 212.0923, found 212.0924.

Ethyl 5-ethyl-4-formyl-1-hydroxy-3-methyl-1H-pyrrole-2-carboxylate (3c, FIG. 4B, entry 3)

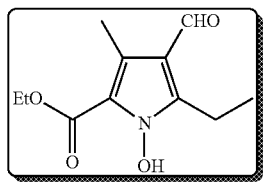

The title compound was prepared according to the general procedure above in 81% yield.

¹H-NMR (400 MHz, CDCl₃) δ 12.32 (brs, 1H), 9.96 (s, 1H), 4.44 (q, J=7.2 Hz, 2H), 3.01 (q, J=7.2 Hz, 2H), 2.56 (s, 3H), 1.44 (t, J=7.2 Hz, 3H), 1.27 (t, J=7.2 Hz, 3H).

¹³C-NMR (100 MHz, CDCl₃) δ 184.8, 165.5, 139.1, 127.9, 114.6, 112.4, 61.6, 16.5, 14.3, 12.7, 10.5.

HRMS (ESI) [M+H]⁺: calcd. for $C_{11}H_{16}O_4$, 226.1079, found 226.1079.

Ethyl 4-formyl-1-hydroxy-3-methyl-5-pentyl-1H-pyrrole-2-carboxylate (3d, FIG. 4B, entry 4)

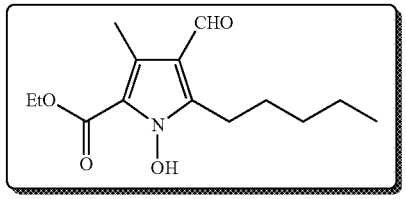

The title compound was prepared according to the typical procedure, as described above in 76% yield.

¹H-NMR (400 MHz, CDCl₃): δ 12.36 (brs, 1H), 9.95 (s, 1H), 4.44 (q, J=7.2 Hz, 2H), 2.97 (t, J=7.2 Hz, 2H), 2.58 (s, 3H), 1.68-1.64 (m, 2H), 1.44 (t, J=7.2 Hz, 3H), 1.36-1.35 (m, 3H), 0.90 (t, J=7.2 Hz, 3H).

¹³C-NMR (100 MHz, CDCl₃): δ 184.8, 165.5, 138.2, 127.8, 115.0, 112.4, 61.6, 31.4, 28.0, 22.9, 22.4, 14.3, 13.9, 10.6.

HRMS (ESI) [M+H]⁺: calcd. for $C_{14}H_{22}NO_4$, 268.1549, found 268.1549.

Ethyl 4-formyl-1-hydroxy-3-methyl-5-phenethyl-1H-pyrrole-2-carboxylate (3e, FIG. 4B, entry 5)

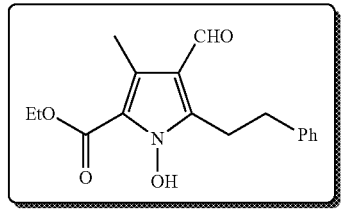

The title compound was prepared according to the general procedure as described above in 82% yield.

¹H-NMR (400 MHz, CDCl₃): δ 12.36 (brs, 1H), 9.96 (s, 1H), 4.44 (q, J=7.2 Hz, 2H), 2.56 (s, 3H), 2.53 (s, 3H), 1.44 (t, J=7.2 Hz, 3H).

¹³C-NMR (100 MHz, CDCl₃): δ 185.0, 165.4, 133.7, 127.8, 115.3, 112.5, 61.6, 14.3, 10.4, 8.7.

HRMS (ESI) [M+H]⁺: calcd. for $C_{10}H_{14}NO_4$, 212.0923, found 212.0924.

Ethyl 5-(3-(benzyloxy)propyl)-4-formyl-1-hydroxy-3-methyl-1H-pyrrole-2-carboxylate (3f, FIG. 4B, entry 6)

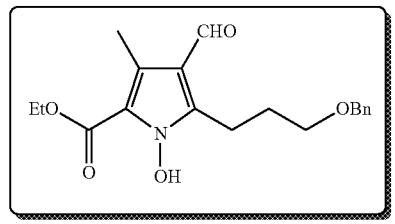

The title compound was prepared according to the typical procedure, as described above in 78% yield.

¹H-NMR (400 MHz, CDCl₃): δ 12.36 (s, 1H), 9.97 (s, 1H), 7.36-7.29 (m, 5H), 4.51 (s, 2H), 4.44 (q, J=7.2 Hz, 2H), 3.54 (t, J=7.2 Hz, 3H), 3.11 (t, J=7.2 Hz, 3H), 2.57 (s, 3H), 2.04-1.97 (m, 2H), 1.45 (t, J=7.2 Hz, 3H).

¹³C-NMR (100 MHz, CDCl₃): δ 184.9, 165.4, 138.4, 137.4, 128.3, 127.8, 127.7, 127.5, 115.2, 112.6, 72.9, 69.3, 61.6, 28.1, 19.9, 14.3, 10.6.

Methyl 4-formyl-1-hydroxy-3,5-dimethyl-1H-pyrrole-2-carboxylate (3g, FIG. 4B, entry 7)

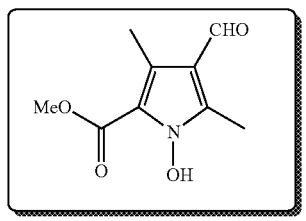

The title compound was prepared according to the typical procedure, as described above in 73% yield.

¹H-NMR (400 MHz, CDCl₃): δ 12.27 (s, 1H), 9.98 (s, 1H), 3.98 (s, 3H), 2.56 (s, 3H), 2.55 (s, 3H).

¹³C-NMR (100 MHz, CDCl₃): δ 184.9, 165.8, 137.8, 128.0, 115.4, 112.4, 52.2, 10.4, 8.8.

HRMS (ESI) [M+H]$^+$: calcd. for $C_9H_{12}NO_4$, 198.0766, found 198.0764.

tert-Butyl 4-formyl-1-hydroxy-3,5-dimethyl-1H-pyrrole-2-carboxylate (3h, FIG. 4B, entry 8)

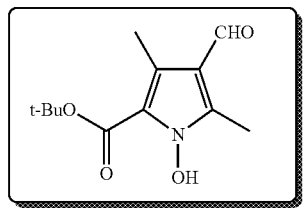

The title compound was prepared according to the typical procedure, as described above in 72% yield.
$^1$H-NMR (400 MHz, CDCl$_3$): δ 12.62 (s, 1H), 9.95 (s, 1H), 2.522 (s, 3H), 2.518 (s, 3H), 1.63 (s, 9H).
$^{13}$C-NMR (100 MHz, CDCl$_3$): δ 185.0, 165.1, 133.1, 127.2, 115.0, 113.2, 84.1, 28.4, 10.4, 8.7.
HRMS (ESI) [M+H]$^+$: calcd. for $C_{12}H_{18}NO_4$, 240.1236, found 240.1238.

Benzyl 4-formyl-1-hydroxy-3,5-dimethyl-1H-pyrrole-2-carboxylate (3i, FIG. 4B, entry 9)

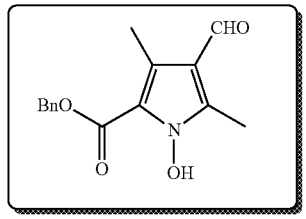

The title compound was prepared according to the typical procedure, as described above in 75% yield.
$^1$H-NMR (400 MHz, CDCl$_3$): δ 12.22 (brs, 1H), 9.96 (s, 1H), 7.44-7.41 (m, 5H), 5.42 (s, 2H), 2.56 (s, 3H), 2.54 (s, 3H).
$^{13}$C-NMR (100 MHz, CDCl$_3$): δ 184.9, 165.1, 135.0, 133.9, 128.8, 128.7, 128.2, 115.4, 112.4, 67.1, 10.5, 8.8.
HRMS (ESI) [M+H]$^+$: calcd. for $C_{15}H_{16}NO_4$, 274.1079, found 274.1079.

Methyl 3-ethyl-4-formyl-1-hydroxy-5-methyl-1H-pyrrole-2-carboxylate (3j, FIG. 4B, entry 10)

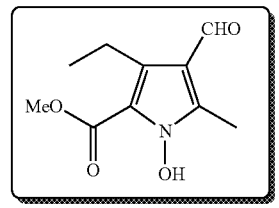

The title compound was prepared according to the typical procedure, as described above in 77% yield.
$^1$H-NMR (400 MHz, CDCl$_3$): δ 12.26 (brs, 1H), 9.93 (s, 1H), 3.96 (s, 3H), 3.00 (q, J=10.0 Hz, 2H), 2.51 (s, 3H), 1.18 (t, J=10.0 Hz, 3H).
$^{13}$C-NMR (100 MHz, CDCl$_3$) δ 184.7, 165.6, 134.8, 133.8, 114.4, 111.5, 52.3, 17.9, 16.4, 8.8.
HRMS (ESI) [M+H]$^+$: calcd. for $C_{10}H_{14}NO_4$, 212.0923, found 212.0927.

Methyl 3,5-diethyl-4-formyl-1-hydroxy-1H-pyrrole-2-carboxylate (3k, FIG. 4B, entry 11)

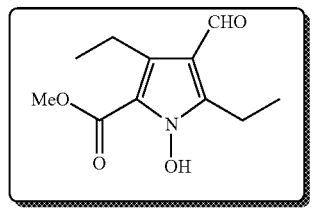

The title compound was prepared according to the typical procedure, as described above in 67% yield.
$^1$H-NMR (400 MHz, CDCl$_3$): δ 12.29 (s, 1H), 9.96 (s, 1H), 3.98 (s, 3H), 3.06-2.98 (m, 4H), 1.26 (t, J=7.6 Hz, 3H), 1.21 (t, J=7.6 Hz, 3H).
$^{13}$C-NMR (100 MHz, CDCl$_3$): δ 184.5, 165.7, 139.2, 134.9, 113.7, 111.5, 52.3, 18.0, 16.7, 16.3, 12.6.
HRMS (ESI) [M+H]$^+$: calcd. for $C_{11}H_{16}NO_4$, 226.1079, found 226.1077.

Methyl 3-ethyl-4-formyl-5-propyl-1H-pyrrole-2-carboxylate (3l, FIG. 4B, entry 12)

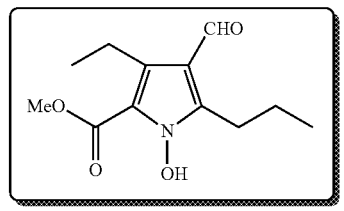

The title compound was prepared according to the typical procedure, as described above in 79% yield.
$^1$H-NMR (400 MHz, CDCl$_3$): δ 12.29 (s, 1H), 9.95 (s, 1H), 3.99 (s, 3H), 3.07-2.95 (m, 4H), 1.73-1.66 (m, 2H), 1.21 (t, J=7.6 Hz, 3H), 0.99 (t, J=7.6 Hz, 3H).
$^{13}$C-NMR (100 MHz, CDCl$_3$): δ 184.60, 165.72, 138.10, 134.80, 114.20, 111.52, 52.29, 24.81, 21.64, 18.03, 16.26, 13.77.

HRMS (ESI) [M+H]⁺: calcd. for $C_{12}H_{18}NO_4$, 240.1236, found 240.1241.

Methyl 3-ethyl-4-formyl-1-hydroxy-5-pentyl-1H-pyrrole-2-carboxylate (3m, FIG. 4B, entry 13)

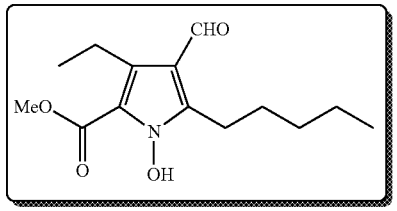

The title compound was prepared according to the typical procedure, as described above in 60% yield.

¹H-NMR (400 MHz, CDCl₃): δ 12.29 (s, 1H), 9.95 (s, 1H), 3.98 (s, 3H), 3.06-2.95 (m, 4H), 1.68-1.65 (m, 2H), 1.37-1.35 (m, 4H), 1.20 (t, J=7.6 Hz, 3H), 0.90 (t, J=6.8 Hz, 3H).

¹³C-NMR (100 MHz, CDCl₃): δ 184.6, 165.7, 138.4, 134.8, 114.1, 111.5, 52.3, 31.4, 27.9, 23.0, 22.4, 18.0, 16.3, 13.9.

HRMS (ESI) [M+H]⁺: calcd. for $C_{14}H_{22}NO_4$, 268.1549, found 268.1546.

5-Acetyl-1-hydroxy-2,4-dimethyl-1H-pyrrole-3-carbaldehyde (3n, FIG. 4B, entry 14)

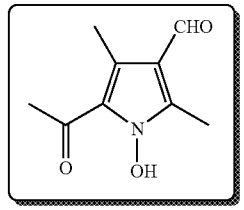

The title compound was prepared according to the typical procedure, as described above in 79% yield.

¹H-NMR (400 MHz, CDCl₃): δ 14.18 (s, 1H), 9.99 (s, 1H), 2.64 (s, 3H), 2.54 (s, 3H), 2.51 (s, 3H).

¹³C-NMR (100 MHz, CDCl₃): δ 192.4, 184.9, 134.6, 129.0, 121.7, 115.8, 28.4, 11.5, 8.5.

HRMS (ESI) [M+H]⁺: calcd. for $C_9H_{12}NO_3$, 182.0817, found 1182.0814.

5-Acetyl-1-hydroxy-2-ethyl-4-methyl-1H-pyrrole-3-carbaldehyde (3o, FIG. 4B, entry 15)

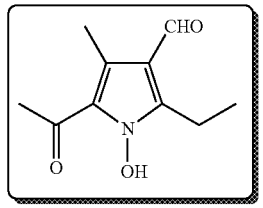

The title compound was prepared according to the typical procedure, as described above in 81% yield.

¹H-NMR (400 MHz, CDCl₃): δ 14.15 (s, 1H), 10.00 (s, 1H), 2.98 (q, J=7.6 Hz, 2H), 2.65 (s, 3H), 2.54 (s, 3H), 1.24 (t, J=7.6 Hz, 3H).

¹³C-NMR (100 MHz, CDCl₃): δ 192.5, 184.7, 139.9, 129.1, 121.6, 115.1, 28.5, 16.2, 12.36, 11.6.

HRMS (ESI) [M+H]⁺: calcd. for $C_{10}H_{14}NO_3$, 196.0974, found 196.0969.

5-Acetyl-1-hydroxy-4-methyl-2-propyl-1H-pyrrole-3-carbaldehyde (3p, FIG. 4B, entry 16)

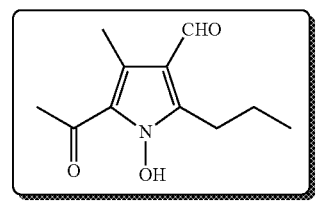

The title compound was prepared according to the typical procedure, as described above in 83% yield.

¹H-NMR (400 MHz, CDCl₃): δ 14.15 (s, 1H), 9.98 (s, 1H), 2.94 (t, J=7.6 Hz, 2 H), 2.65 (s, 3H), 2.54 (s, 3H), 1.72-1.66 (m, 2H), 0.98 (t, J=7.2 Hz, 3H).

¹³C-NMR (100 MHz, CDCl₃): δ 192.5, 184.8, 138.8, 129.0, 121.7, 115.6, 28.5, 24.4, 21.4, 13.8, 11.6.

HRMS (ESI) [M+H]⁺: calcd. for $C_{11}H_{16}NO_3$, 210.1130, found 210.1133.

5-Acetyl-1-hydroxy-4-methyl-2-pentyl-1H-pyrrole-3-carbaldehyde (3q, FIG. 4B, entry 17)

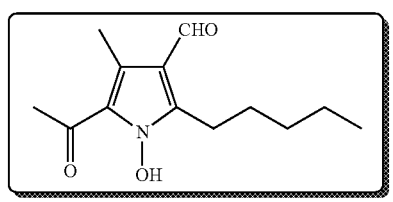

The title compound was prepared according to the typical procedure, as described above in 77% yield.

¹H-NMR (400 MHz, CDCl₃): δ 14.15 (s, 1H), 9.99 (s, 1H), 2.95 (t, J=7.6 Hz, 2H), 2.65 (s, 3H), 2.54 (s, 3H), 1.67-1.63 (m, 2H), 1.35-1.34 (m, 4H), 0.98 (t, J=7.2 Hz, 3H).

¹³C-NMR (100 MHz, CDCl₃): δ 192.5, 184.7, 139.0, 129.0, 121.7, 115.5, 31.4, 28.5, 27.7, 22.5, 22.3, 13.9, 11.6.

HRMS (ESI) [M+H]+: calcd. for C₁₃H₂₀NO₃, 238.1443, found 238.1439.

5-Acetyl-1-hydroxy-4-methyl-2-phenethyl-1H-pyrrole-3-carbaldehyde (3r, FIG. 4B, entry 18)

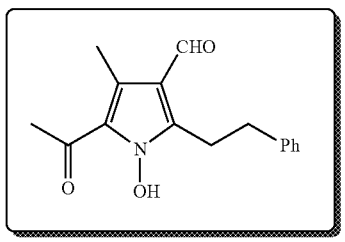

The title compound was prepared according to the typical procedure, as described above in 82% yield.

¹H-NMR (400 MHz, CDCl₃): δ 14.21 (s, 1H), 9.89 (s, 1H), 7.32-7.23 (m, 5H), 3.29-3.25 (m, 2H), 2.96 (t, J=8.0 Hz, 2H), 2.65 (s, 3H), 2.56 (s, 3H).

¹³C-NMR (100 MHz, CDCl₃): δ 192.6, 184.7, 140.4, 137.5, 128.9, 128.5, 128.5, 126.4, 121.7, 115.7, 33.8, 28.5, 25.0, 11.6.

HRMS (ESI) [M+H]+: calcd. for C₁₆H₁₈NO₃, 272.1287, found 272.1287.

5-Acetyl-1-hydroxy-2-(3-(benzyloxy)propyl)-4-methyl-1H-pyrrole-3-carbaldehyde (3s, FIG. 4B, entry 19)

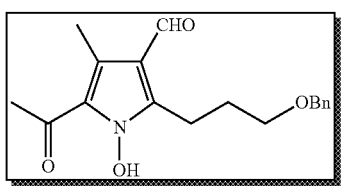

The title compound was prepared according to the general procedure as described above in 73% yield.

¹H-NMR (400 MHz, CDCl₃): δ 14.15 (s, 1H), 10.00 (s, 1H), 7.37-7.28 (m, 5H), 4.50 (s, 2H), 3.54 (t, J=6.0 Hz, 2H), 3.10 (t, J=7.2 Hz, 2H), 2.64 (s, 3H), 2.53 (s, 3H), 2.04-1.97 (m, 2H).

¹³C-NMR (100 MHz, CDCl₃): δ 192.5, 184.9, 138.4, 138.3, 128.9, 128.3, 127.7, 127.5, 121.8, 115.7, 72.9, 69.3, 28.5, 27.8, 19.7, 11.6.

tert-Butyl 2-(5-acetyl-3-formyl-1-hydroxy-4-methyl-1H-pyrrol-2-yl) ethyl carbamate (3t, FIG. 4B, entry 20)

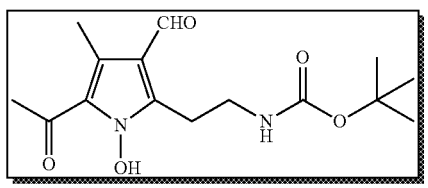

¹H-NMR (400 MHz, CDCl₃): δ 14.21 (s, 1H), 9.99 (s, 1H), 7.37-7.28 (m, 5H), 4.87 (brs, 1H), 3.45 (t, J=6.0 Hz, 2H), 3.21 (t, J=6.4 Hz, 2H), 2.65 (s, 3H), 2.56 (s, 3H), 1.41 (s, 9H).

¹³C-NMR (100 MHz, CDCl₃): δ 192.6, 185.0, 155.9, 135.3, 129.0, 121.8, 116.3, 79.3, 38.9, 28.5, 28.3, 23.4, 11.4.

HRMS (ESI) [M+Na]: calcd. for C₁₅H₂₂N₂O₅Na, 333.1426, found 333.1429.

5-Benzoyl-1-hydroxy-2-methyl-4-phenyl-1H-pyrrole-3-carbaldehyde (3u, FIG. 4B, entry 21)

To a solution of oxime compound (2-(hydroxyimino)-1,3-diphenylpropane-1,3-dione, 1 g) (0.4 mmol, 1.0 eq) and (E)-but-2-enal (2b, 1.0 mmol, 2.5 eq) in toluene (2 mL) was added catalyst VII (0.12 mmol, 0.3 eq) at room temperature. The resulting mixture was stirred vigorously. After the reaction was completed (monitored by TLC), the product 3t was afforded by flash chromatography over silica gel (EtOAc/Hexane=1:15 to 1:10) in 58% yield.

¹H-NMR (400 MHz, CDCl₃): δ 13.79 (s, 1H), 9.64 (s, 1H), 7.33-7.23 (m, 3H), 7.15-6.99 (m, 7H), 2.72 (s, 3H).

¹³C-NMR (100 MHz, CDCl₃): δ 190.3, 187.2, 136.3, 135.4, 134.6, 131.8, 131.1, 130.8, 128.8, 127.8, 127.8, 127.6, 120.2, 115.8, 9.6.

HRMS (ESI) [M+H]+: calcd. for $C_{19}H_{16}NO_3$, 306.1130, found 306.1127.

5-Benzoyl-1-hydroxy-2,4-dimethyl-1H-pyrrole-3-carbaldehyde (5a, FIG. 5B)

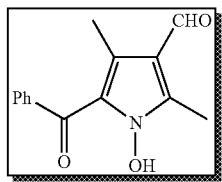

The title compound was prepared according to the typical procedure, as described above in 76% yield.

$^1$H-NMR (400 MHz, CDCl$_3$): δ 13.30 (brs, 1H), 9.98 (s, 1H), 7.67-7.60 (m, 3H), 7.53-7.50 (m, 2H), 2.60 (s, 3H), 2.10 (s, 3H).
$^{13}$C-NMR (100 MHz, CDCl$_3$): δ 190.0, 184.9, 138.0, 136.1, 132.5, 129.9, 128.6, 128.5, 122.1, 116.2, 12.0, 8.8.
HRMS (ESI) [M+H]+: calcd. for $C_{14}H_{14}NO_3$, 244.0974, found 244.0977.

5-Acetyl-1-hydroxy-4-phenyl-2-propyl-1H-pyrrole-3-carbaldehyde (6b, FIG. 5B)

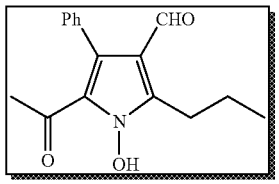

The title compound was isolated according to the typical procedure, as described above in 13% yield.

$^1$H-NMR (400 MHz, CDCl$_3$): δ 14.20 (brs, 1H), 9.44 (s, 1H), 7.49-7.48 (m, 3H), 7.402-7.395 (m, 2H), 3.07 (t, J=7.6 Hz, 2H), 1.97 (s, 3H), 1.79-1.74 (m, 2H), 1.04 (t, J=7.6 Hz, 2H).
$^{13}$C-NMR (100 MHz, CDCl$_3$): δ 193.3, 186.4, 1137.2, 134.8, 131.6, 130.5, 128.9, 128.5, 120.3, 116.4, 27.5, 25.1, 21.0, 14.0.

5-Benzoyl-1-hydroxy-4-methyl-2-propyl-1-hydroxy-pyrrole-3-carbaldehyde (5b, FIG. 5B)

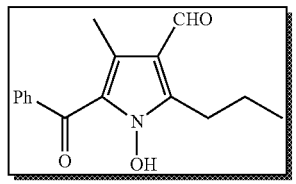

The title compound was prepared according to the typical procedure, as described above in 62% yield.

$^1$H-NMR (400 MHz, CDCl$_3$): δ 13.28 (brs, 1H), 9.97 (s, 1H), 7.68-7.60 (m, 3H), 7.54-7.50 (m, 2H), 3.54 (t, J=7.6 Hz, 2H), 2.11 (s, 3H), 1.80-1.74 (m, 2H), 1.04 (t, J=7.6 Hz, 2H).

$^{13}$C-NMR (100 MHz, CDCl$_3$): δ 190.1, 184.8, 140.2, 138.0, 132.5, 129.9, 128.6, 128.6, 122.0, 116.0, 24.7, 21.6, 13.9, 12.2.
HRMS (ESI) [M+H]+: calcd. for $C_{16}H_{18}NO_3$, 272.1287, found 272.1286.

5-Acetyl-1-hydroxy-2-pentyl-4-phenyl-1H-pyrrole-3-carbaldehyde (6c, FIG. 5B)

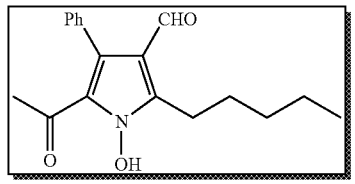

The title compound was isolated according to the typical procedure, as described above in 16% yield.

$^1$H-NMR (400 MHz, CDCl$_3$): δ 14.20 (s, 1H), 9.45 (s, 1H), 7.49-7.48 (m, 3H), 7.40-7.39 (m, 2H), 3.08 (t, J=8.0 Hz, 2H), 1.97 (s, 3H), 1.74-1.70 (m, 2H), 1.41-1.39 (m, 4H), 0.93 (t, J=6.8 Hz, 3H).
$^{13}$C-NMR (100 MHz, CDCl$_3$): δ 193.3, 186.4, 137.4, 134.8, 131.6, 130.5, 128.8, 128.5, 120.3, 116.3, 31.6, 27.5, 27.2, 23.2, 22.4, 14.0.

5-Benzoyl-1-hydroxy-4-methyl-2-pentyl-1H-pyrrole-3-carbaldehyde (5c, FIG. 5B)

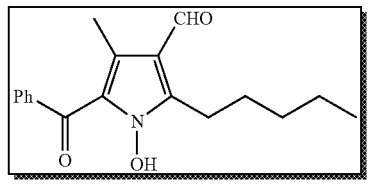

The title compound was prepared according to the typical procedure, as described above in 60% yield.

$^1$H-NMR (400 MHz, CDCl$_3$): δ 13.29 (s, 1H), 9.97 (s, 1H), 7.68-7.66 (m, 2H), 7.62-7.60 (m, 1H), 7.54-7.50 (m, 2H), 3.03 (t, J=8.0 Hz, 2H), 2.11 (s, 3H), 1.75-1.71 (m, 2H), 1.42-1.39 (m, 4H), 0.93 (t, J=6.8 Hz, 3H).
$^{13}$C-NMR (100 MHz, CDCl$_3$): δ 190.1, 184.8, 140.5, 138.0, 132.5, 130.0, 128.6, 128.6, 122.0, 115.9, 31.5, 27.9, 22.9, 22.4, 14.0, 12.2.
HRMS (ESI) [M+H]+: calcd. for $C_{18}H_{22}NO_3$, 300.1600, found 300.1598.

The above reaction of the process of the invention is a catalytic synthesis of multisubstituted N-hydroxypyrroles by a domino reaction of α-carbonyl oxime compounds and,—unsaturated aldehydes in the presence of secondary amine catalysts through the iminium activation strategy. This approach differs from previously reported strategies, as oximes were employed as N-selective nucleophiles in the Michael addition step instead of the more commonly used O-selective nucleophiles in organocatalysis.

Figures 3A, 3B:
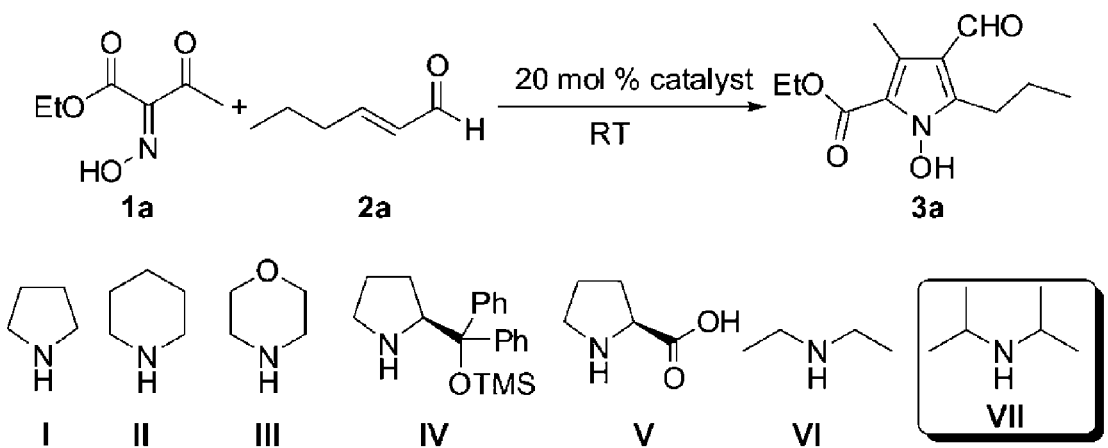
FIG. 3A depicts a reaction scheme on the screening of secondary amines and solvents for the domino reaction of the process of the invention.
FIG. 3B depicts data of exemplary reaction conditions and obtained yields. Reactions were carried out using compounds 1a (0.2 mmol, 1.0 equivalents) and 2a (0.5 mmol, 2.5 equivalents) with the respective secondary amine (20 mol %) as a catalyst (I-VII) in the indicated solvent (1.0 mL) at room temperature. [a]: Yield of isolated product.

Amine catalysts perform efficient iminium activation by lowering the LUMO of α,β-unsaturated aldehydes (Enders, D, et al., Angew. Chem. Int. Ed. (2007) 46, 1570; Ramón, D J, & Yus, M, Angew. Chem. Int. Ed. (2005) 44, 1602). The use of IV as a catalyst for a domino reaction involving sequential Michael addition and intramolecular aldol condensation is also illustrated in FIG. 3. This FIG. depicts ethyl 2-(hydroxy-imino)-3-oxobutanoate (1a) and (E)-hex-2-enal (2a) as reactants in the reaction. After optimizing the reaction conditions for compound IV as a catalyst by changing the amount of the aldehyde and studying solvent effects, the yield could be improved to 82% (FIG. 3B, entry 4). The use of further secondary amine catalysts (I-VII) is also illustrated in FIG. 3.

The results were influenced by both amine catalysts and solvents. Surprisingly, no product was obtained when DMSO or DMF were used as solvent. Further examples show the use of diisopropylamine (VII) as a catalyst, selected due to its low cost, ready availability, and high catalytic efficiency in the reaction (FIG. 3B, entry 7). After the optimal conditions had been established with catalyst VII, the generality of the domino process was investigated (FIG. 4). Good yields could be achieved with many substrates (FIG. 4B, entries 1-19) and several types of moiety $R^1$, such as Me, MeO, EtO, tBuO, and BnO, did not significantly affect the reaction (FIG. 4, entries 1-9). If $R^2$ was changed from methyl to ethyl, the yields were almost the same even when different aldehydes were used (FIG. 4B, entries 10-13). When a less reactive substrate was used, a higher catalytic loading and longer reaction time were required to obtain pyrrole 3u in 58% yield (entry 21). The above reaction proceeded well with a variety of different functional groups $R^3$, such as phenylethyl, benzoxypropyl, and 2-(tert-butoxycarbonylamino) ethyl, attached to the α,β-unsaturated aldehydes (FIG. 4B, entries 5, 6, 18-20). However, the reaction did not proceed when the α,β-unsaturated aldehydes possessed beta aromatic substituents, such as phenyl. This domino reaction is expected to find potential use in synthetic chemistry laboratories and in industry, despite its limitations, since $R^3$ bearing many different functionalities can be tolerated.

When oxime compound 4 was subjected to the above reaction conditions, the two theoretically predicted pyrroles (5 and 6, FIG. 5A) were isolated (FIG. 5B, entries 2 and 3). Interestingly, the use of different substituted aldehydes could influence the results significantly. For example, when $R^3$ was a methyl group, only one product 5a was isolated. Hence, the reaction was investigate further by changing other conditions in order to achieve higher regioselectivity. Although changing the solvent did not improve the results, changing the catalyst to IV or V (FIG. 5B, entries 5-7) surprisingly led to the formation of only one major product. The excellent regioselectivity may be attributed to the bulky group in catalyst IV and hydrogen bonding in catalyst V.

Transforming product 3a into 1H-pyrrole under mild conditions with good yield illustrated the synthetic usefulness of these polyfunctionalized N-hydroxypyrroles. Furthermore, the methyl group can be facilely converted into an aldehyde (FIG. 6, cf. Syper, L, *Tetrahedron Lett.* (1966) 7, 4493; Baciocchi, E, et al., *J. Org. Chem.* (1992) 57, 2486).

Conversion into 1H-pyrrole (ethyl-4-formyl-3-methyl-5-propyl-1H-pyrrole-2-carboxylate)

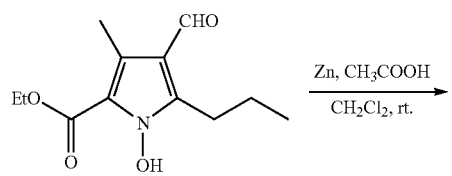

-continued

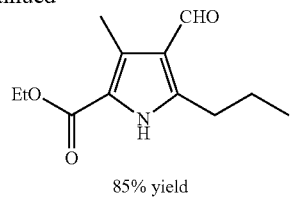

85% yield

To a solution of 3a (48 mg, 0.2 mmol) in dichloromethane (5 mL), added zinc dust (130 mg, 2.0 mmol) and acetic acid (0.2 mL), stirred at room temperature for 4 hours. The reaction was completed (monitored by TLC), the mixture were quenched with water, extracted with dichloromethane three times, dried over anhydrous $Na_2SO_4$, and concentrated under reduced pressure. The product 1H-pyrrole was afforded by flash chromatography over silica gel in 85% yield.

$^1$H-NMR (400 MHz, CDCl$_3$): δ 10.03 (s, 1H), 9.23 (brs, 1H), 4.38 (q, J=7.2 Hz, 2H), 2.92 (t, J=8.0 Hz, 2H), 2.11 (s, 3H), 1.76-1.70 (m, 4H), 1.40 (t, J=7.2 Hz, 3H), 1.00 (t, J=7.2 Hz, 3H).

$^{13}$C-NMR (100 MHz, CDCl$_3$): δ 186.1, 161.8, 144.8, 130.2, 121.3, 118.8, 60.6, 28.6, 22.6, 14.5, 13.8, 10.6.

HRMS (ESI) [M+H]$^+$: calcd. for $C_{12}H_{18}NO_3$, 224.1287, found 224.1285.

Figure 7:
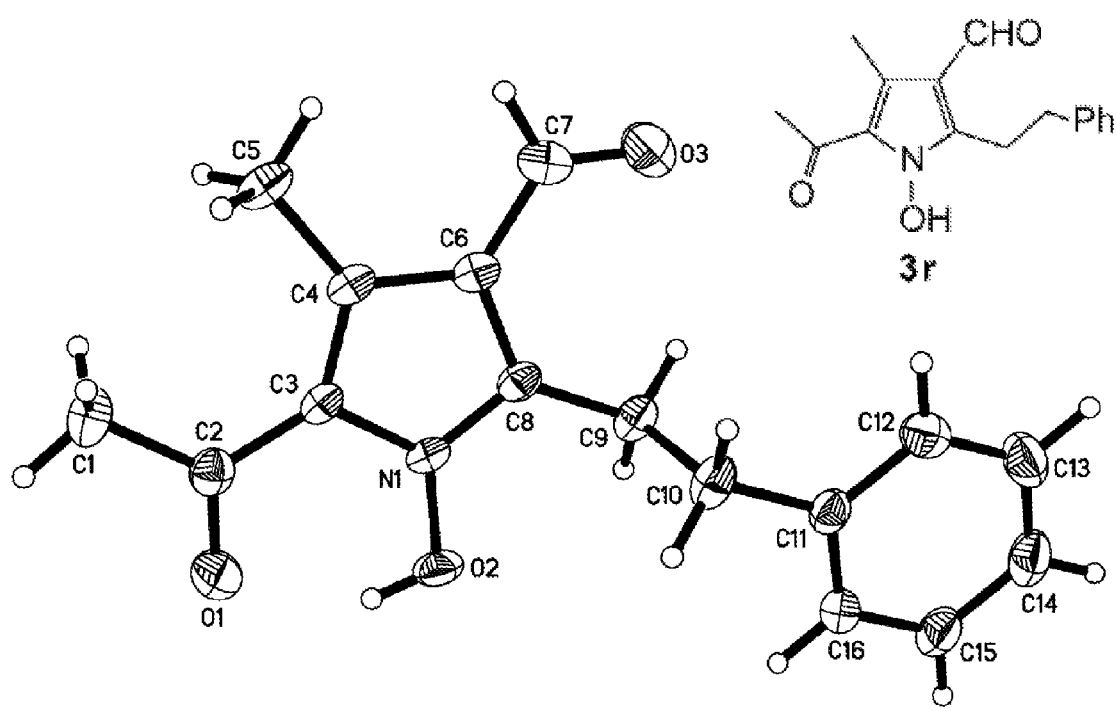
FIG. 7 depicts the molecular structure of compound 3r determined by X-ray diffraction crystallography. The crystal structure has been deposited at the Cambridge Crystallographic Data Centre and allocated the deposition number: CCDC 703858.

X-ray crystallographic analysis of the domino product 3r further confirmed the structure of the product established by NMR spectroscopy (FIG. 7, CCDC 703858 contains the supplementary crystallographic data. These data can be obtained free of charge from The Cambridge Crystallographic Data Centre via www.ccdc.cam.ac.uk/data_request/cif.).

One-pot multicomponent reactions have recently gained considerable and steadily increasing academic, economic, and ecological attention owing to their improved efficiency, reduced waste, and rapid access of structural diversity (Ramón & Yus, 2005, supra). Such reactions carried out in water (Narayan, S, et al., *Angew. Chem. Int. Ed.* (2005) 44, 3275; Hayashi, Y, *Angew. Chem. Int. Ed.* (2006) 45, 8103; Blackmond, D G, et al., Angew. Chem. Int. Ed. (2007) 46, 3798; Wang, F., et al., *Adv. Synth. Catal.* (2008) 350, 1830) would be ideal reactions from a green chemistry perspective. Considering these advantages, these reactions were carried out in water, which lead to N-hydroxypyrroles isolated as major products in moderate yields (FIG. 8).

To a solution of ethyl acetoacetate or acetoacetate or methyl 3-oxopentanoate (0.5 mmol) in acetic acid (0.6 mmol) were added sodium nitrite (0.6 mmol) in water (1 mL) dropwise. After stirring at room temperature for 30 minutes (E)-hex-2-enal 2a (1.25 mmol) was added in one portion, followed by adding catalyst VII (0.1 mmol) in water (1 mL). The resulting mixture was stirred vigorously. After the reaction was completed (monitored by TLC), the mixture were quenched with saturated ammonium chloride extracted with dichloromethane three times, dried over anhydrous $Na_2SO_4$, and concentrated under reduced pressure. The product 3a was afforded by flash chromatography over silica gel in 65% yield. The product 3o was afforded by flash chromatography over silica gel in 52% yield. The product 3k was afforded by flash chromatography over silica gel in 57% yield.

Notably, lower yields were obtained from the one-pot synthesis of pyrrole when compared to a corresponding synthesis using two separate steps with carbonyl compounds, possibly as a result of the significant influence of solvent in these reactions.

Figure 9B:
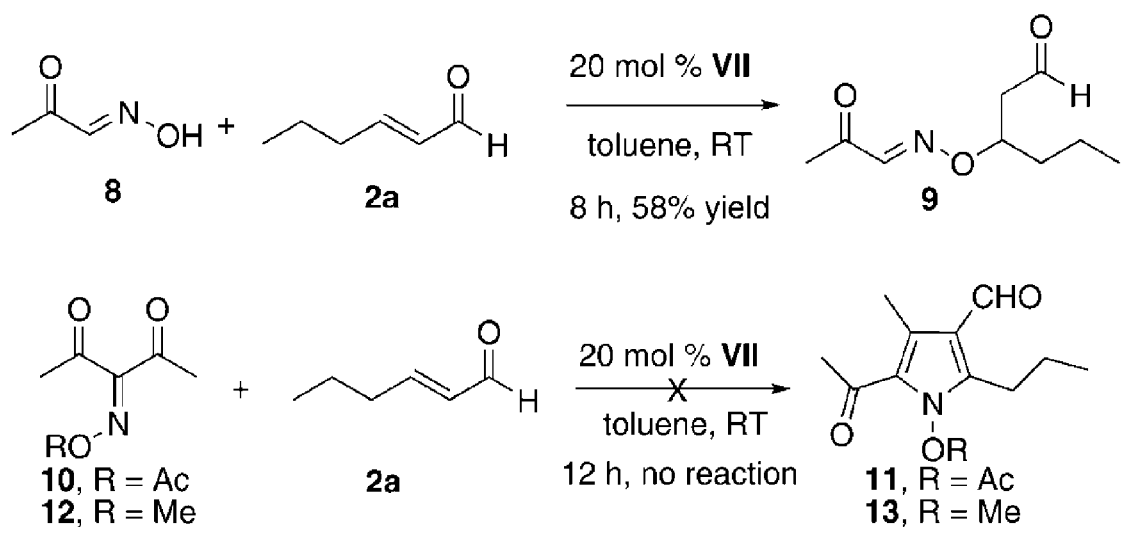
FIG. 9B shows control reactions that were carried out to investigate the O/N-selectivity of the reaction.
Figure 10A:
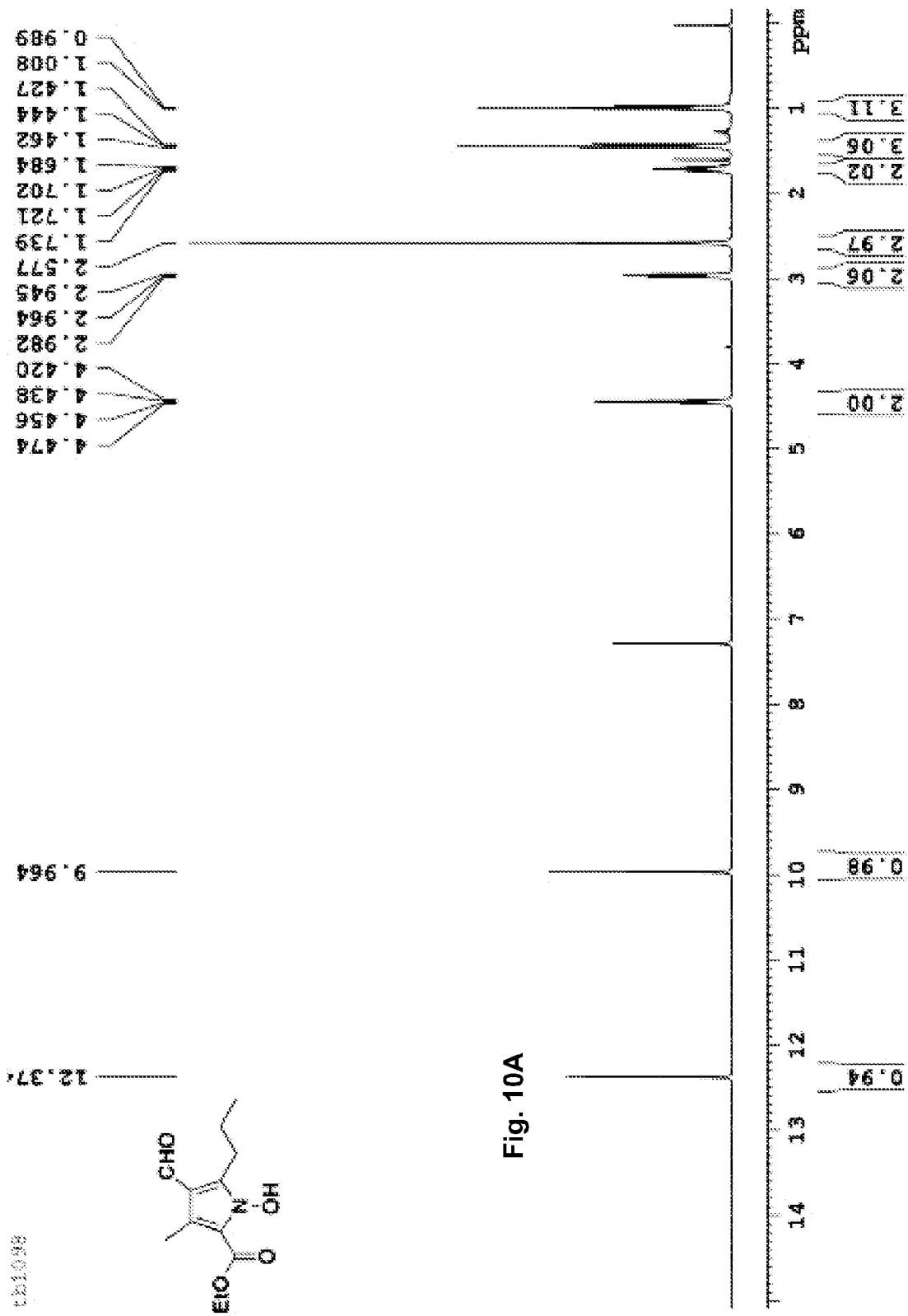
Figure 10B:
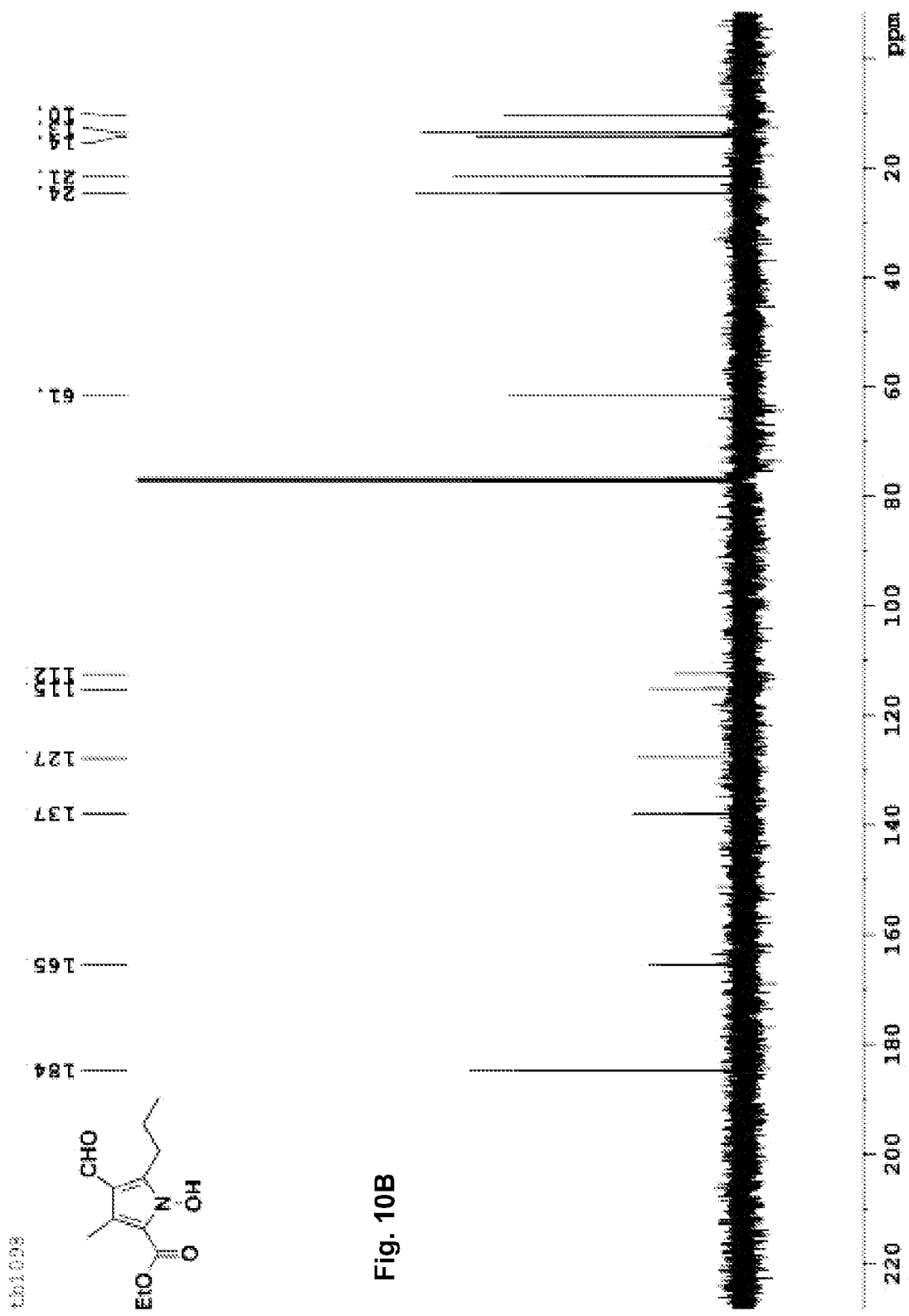
Figure 11A:
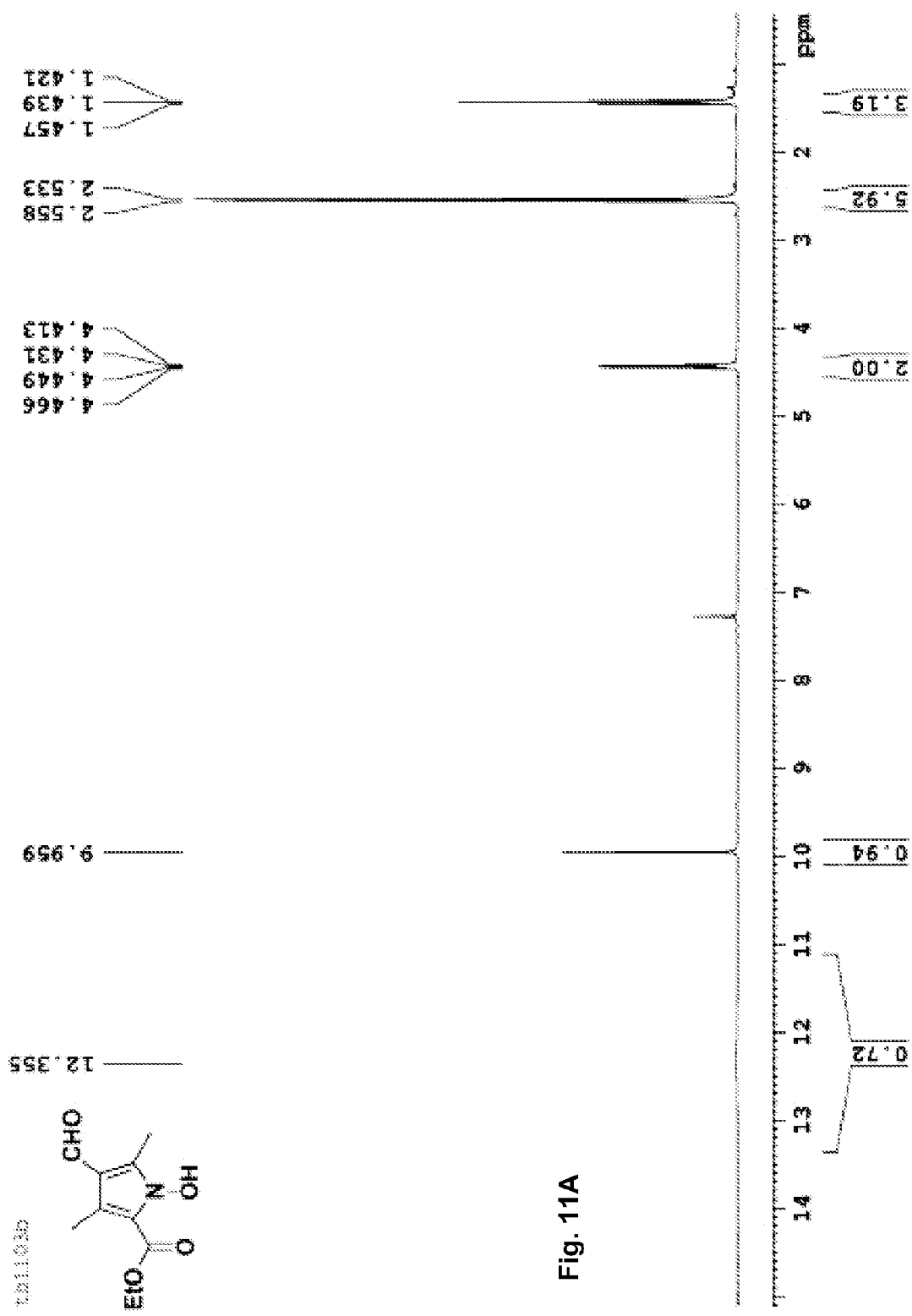
FIG. 11 depicts a $^1$H NMR spectrum (A) and a $^{13}$C NMR spectrum (B) of compound 3b.
Figure 11B:
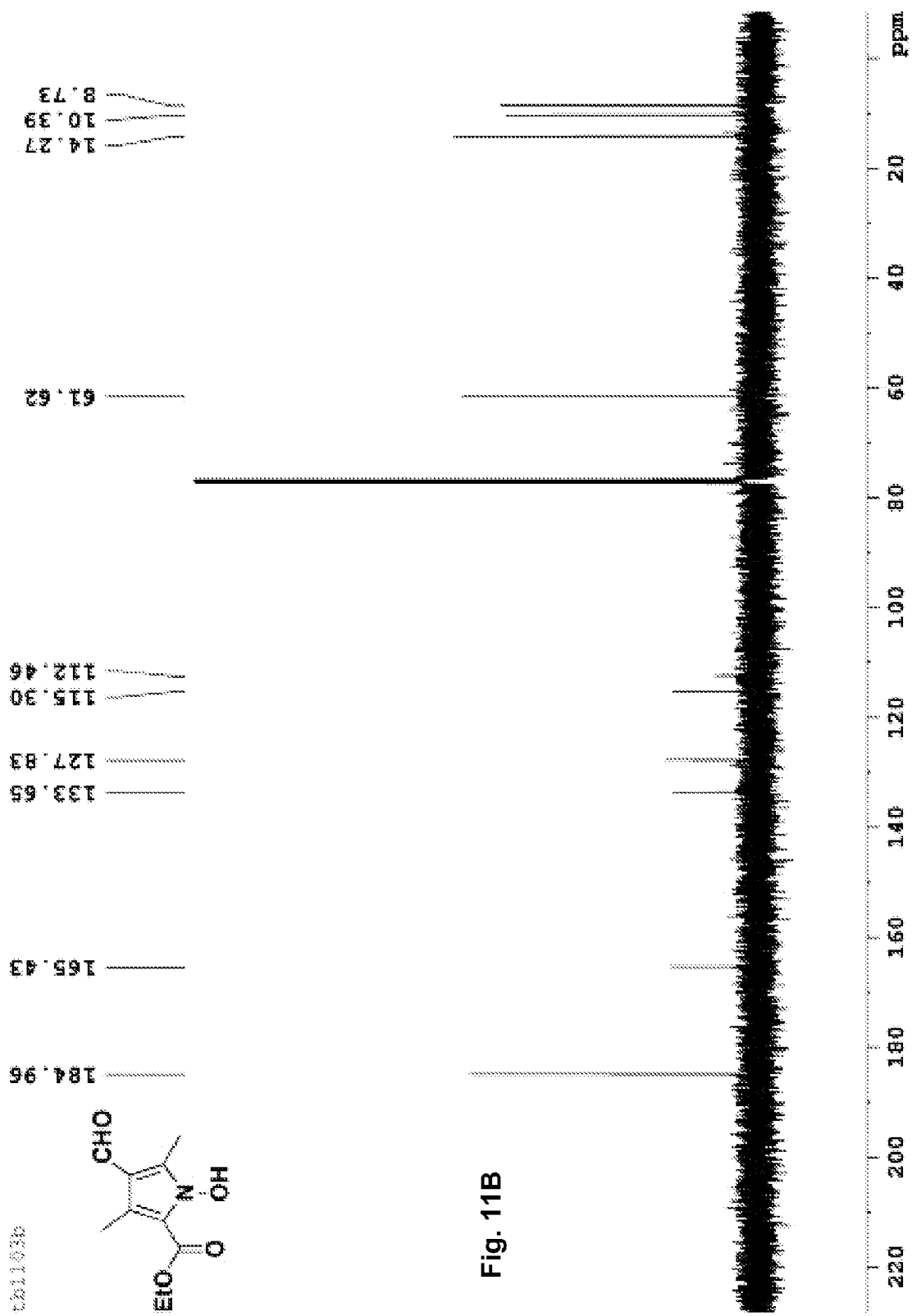
Figure 12A:
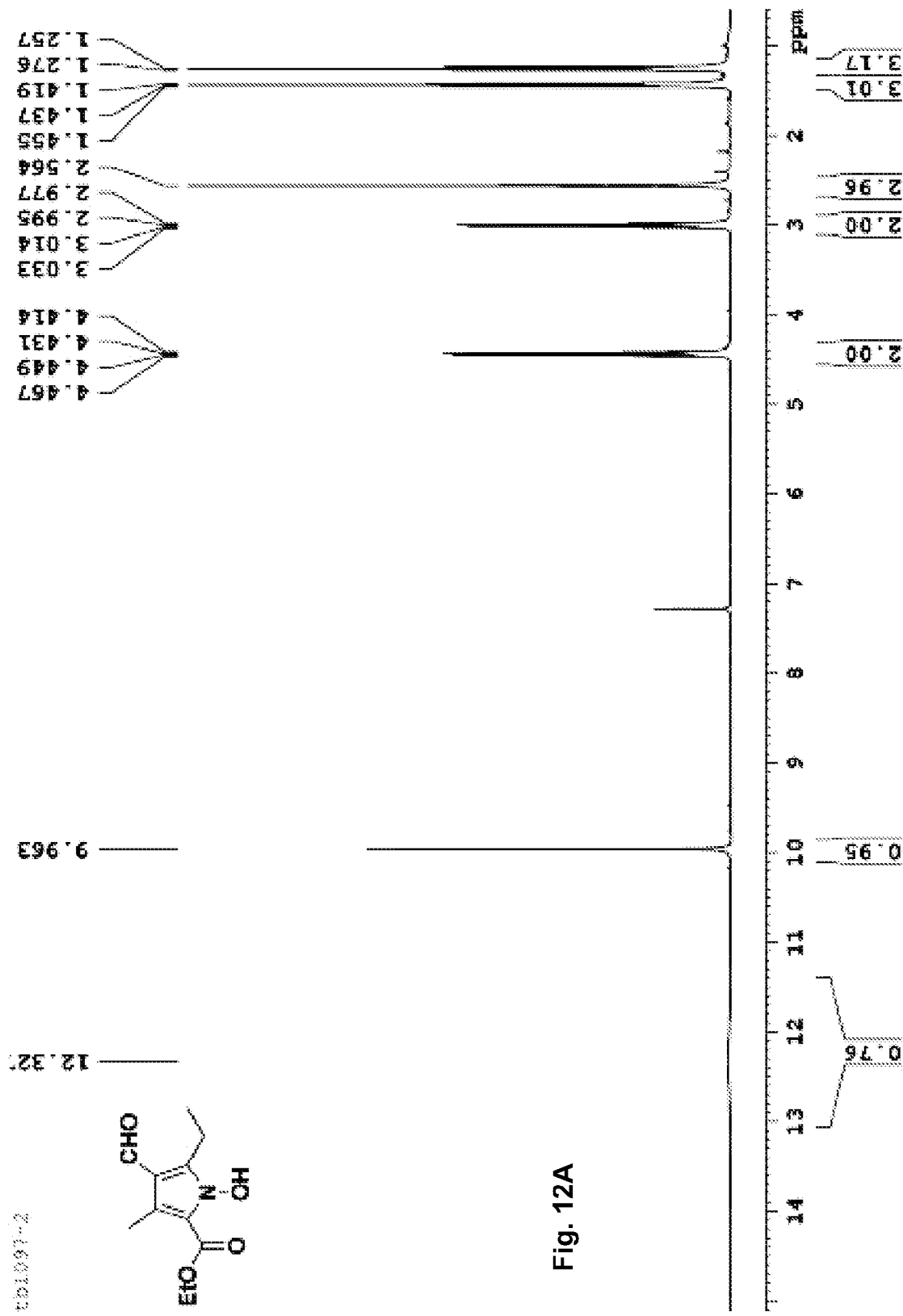
FIG. 12 depicts a $^1$H NMR spectrum (A) and a $^{13}$C NMR spectrum (B) of compound 3c.
Figure 12B:
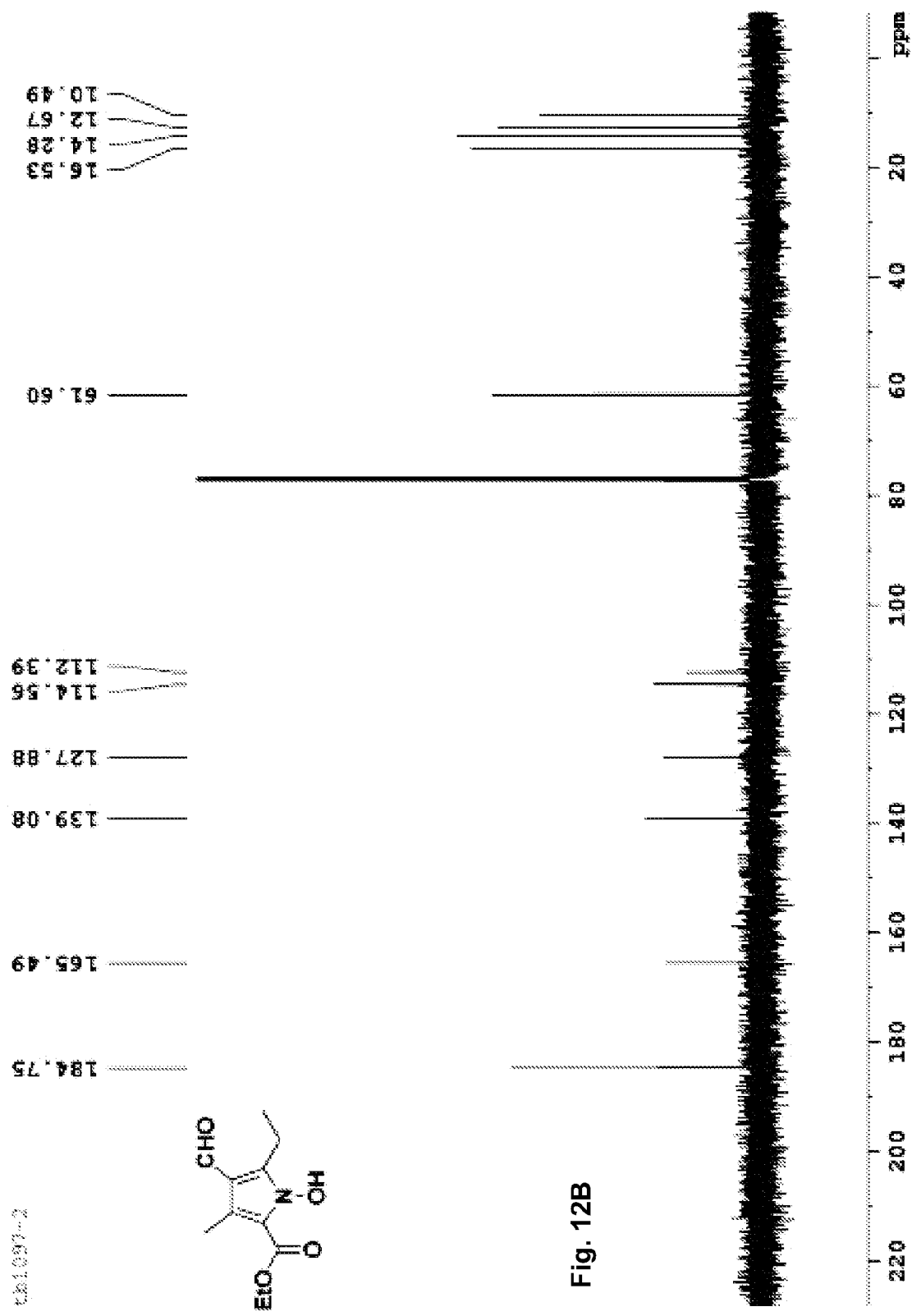
Figure 13A:
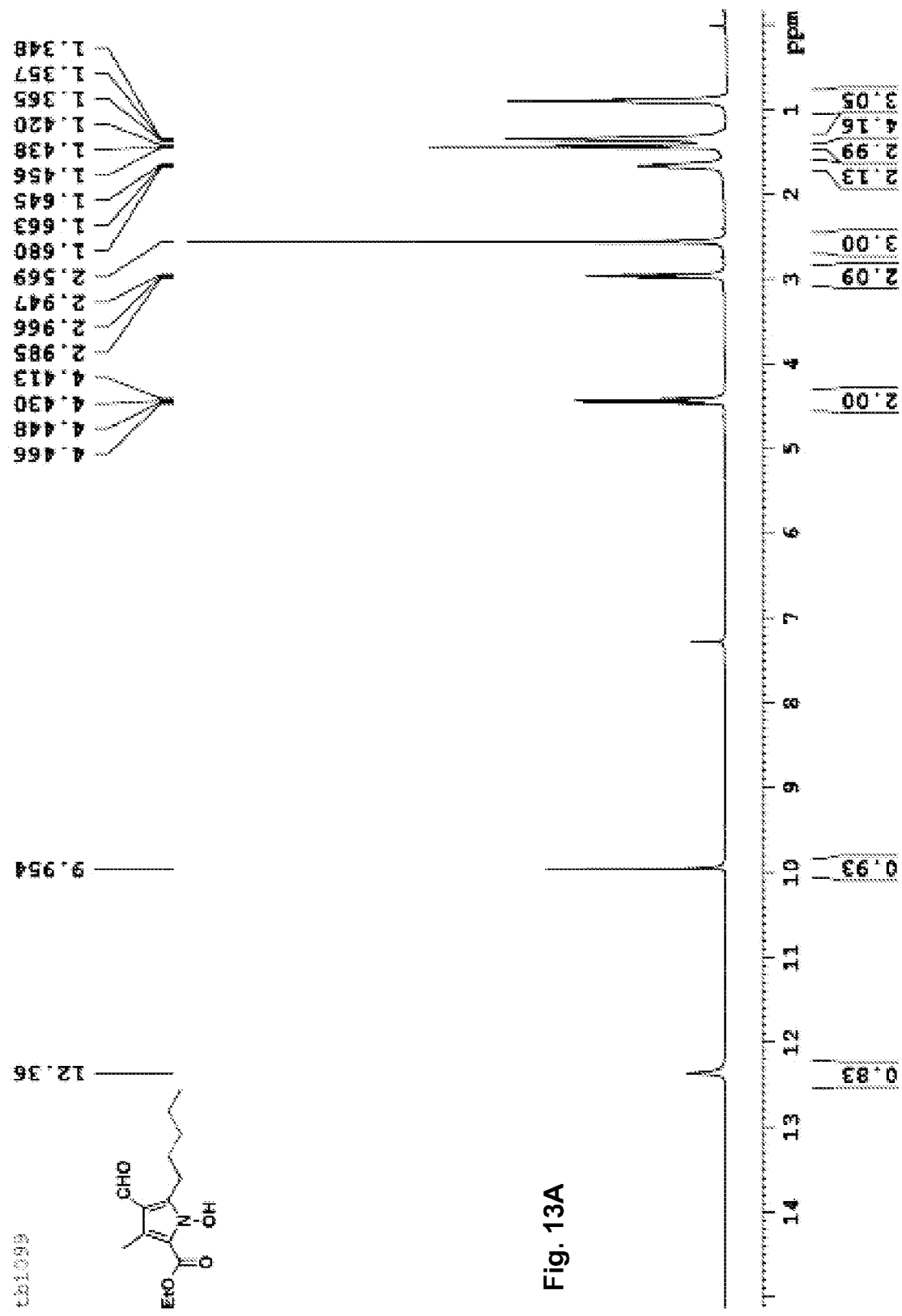
FIG. 13A depicts a $^1$H NMR spectrum and FIG. 13B a $^{13}$C NMR spectrum of compound 3d.
Figure 13B:
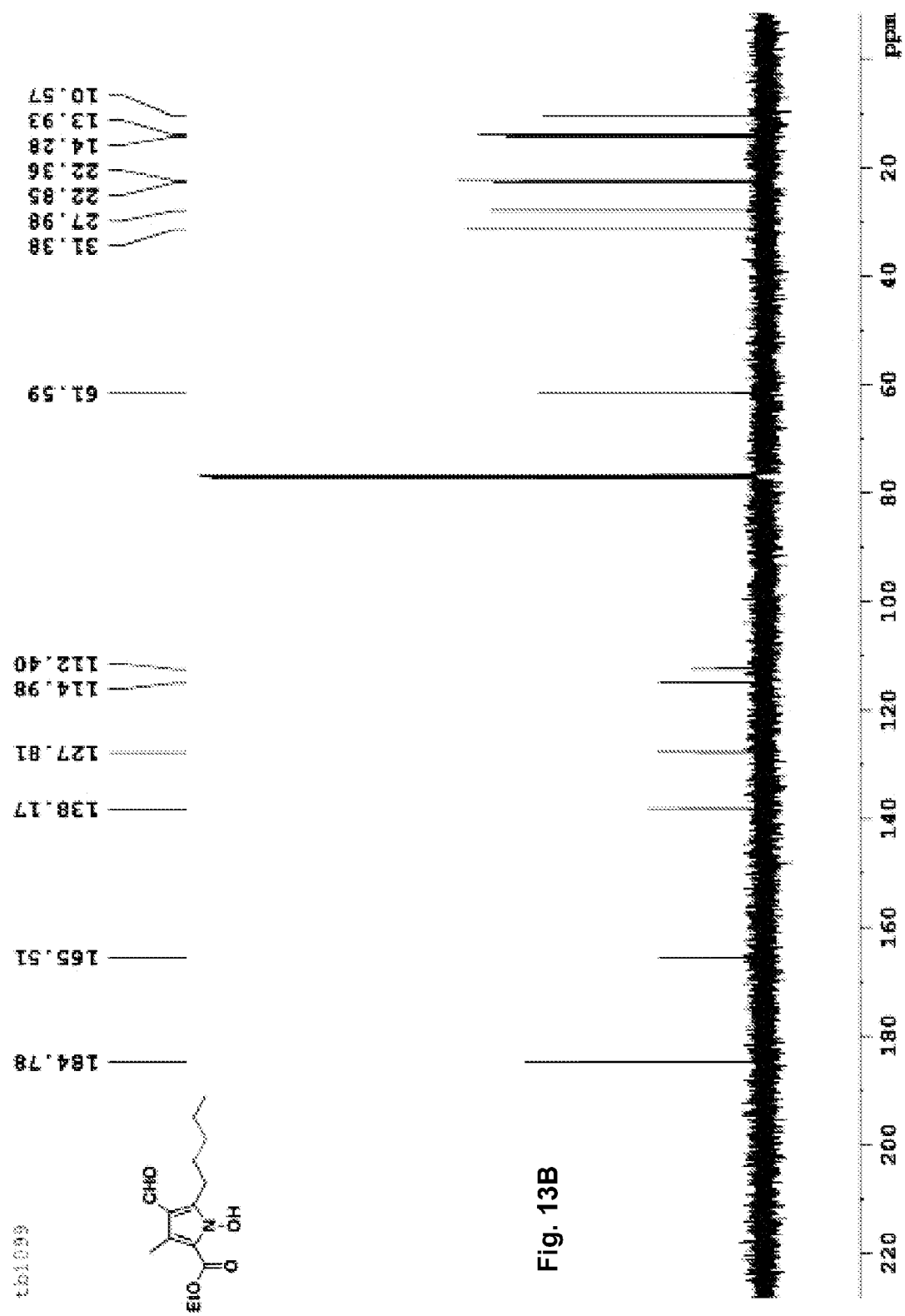
Figure 14A:
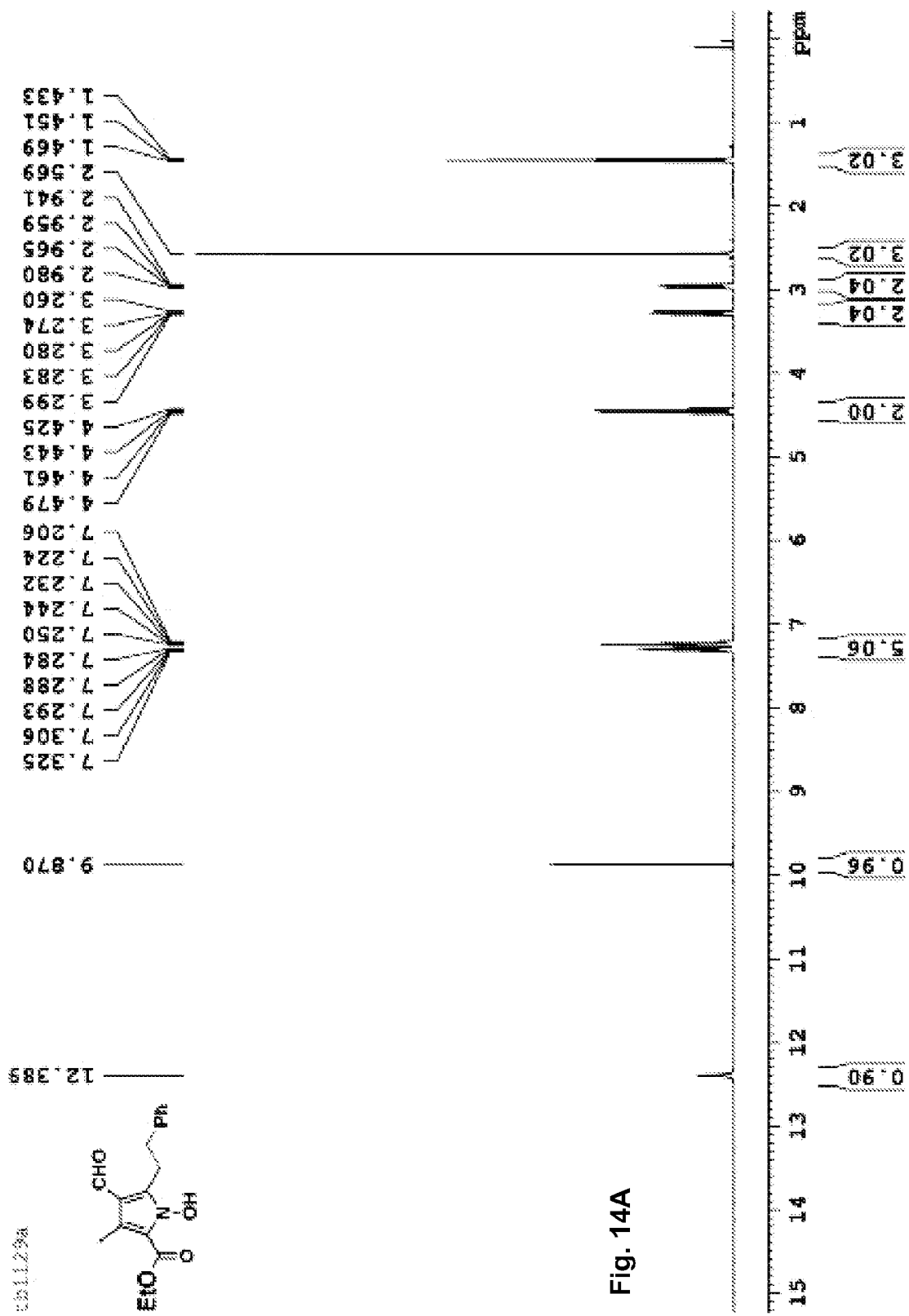
FIG. 14 depicts $^1$H NMR (A) and $^{13}$C NMR (B) spectra of compound 3e.
Figure 14B:
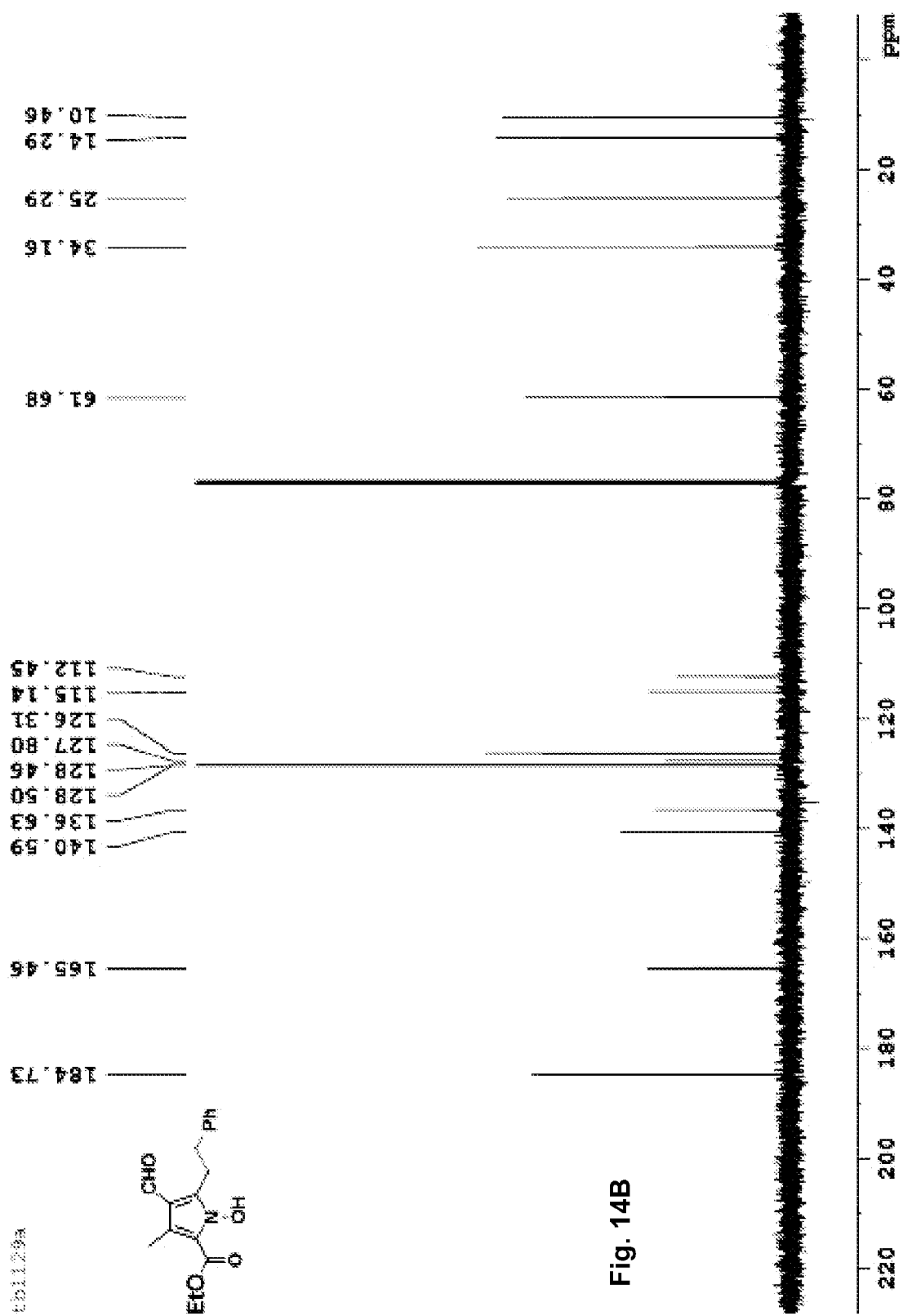
Figure 15A:
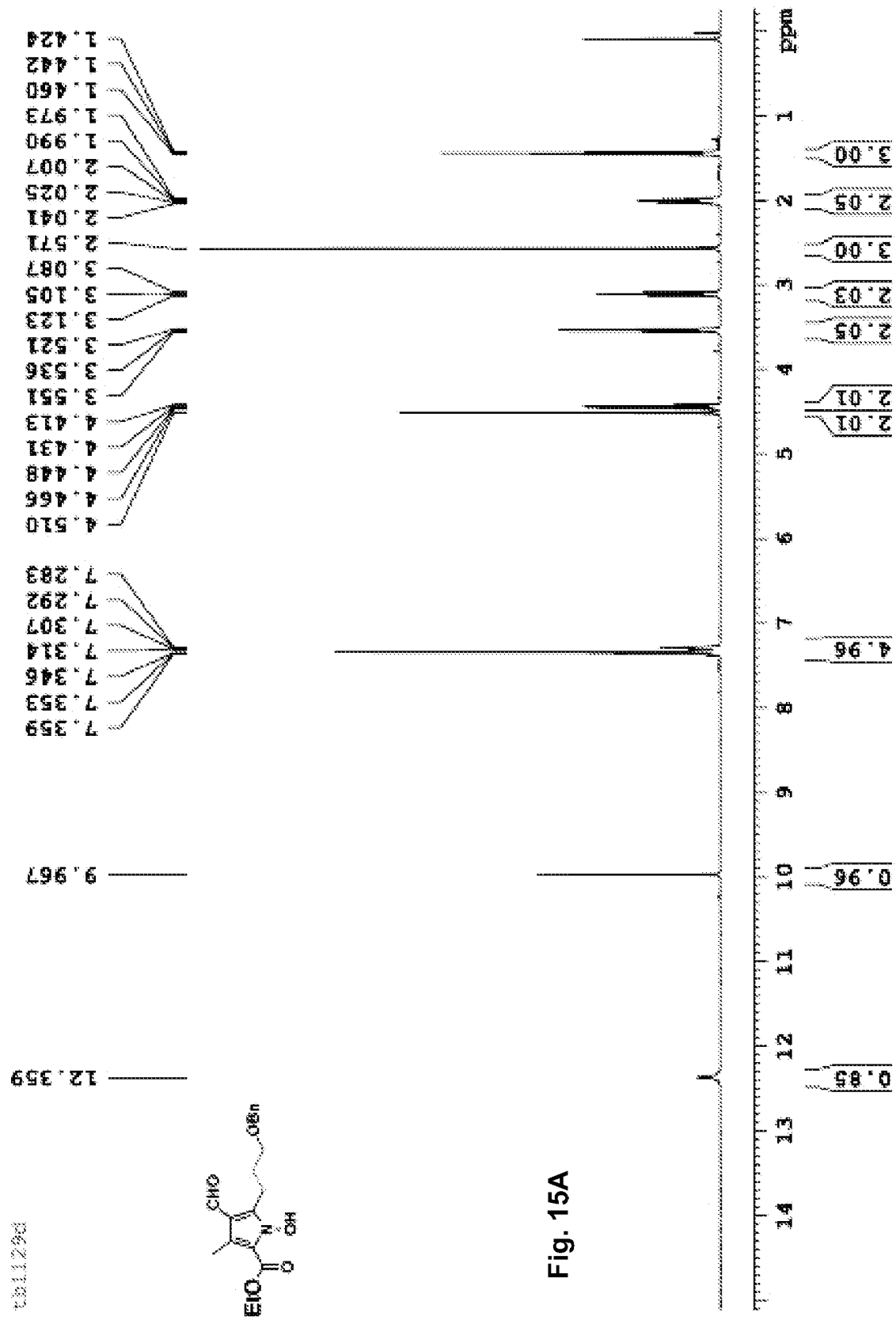
FIG. 15 depicts $^1$H NMR (A) and $^{13}$C NMR (B) spectra of compound 3f.
Figure 15B:
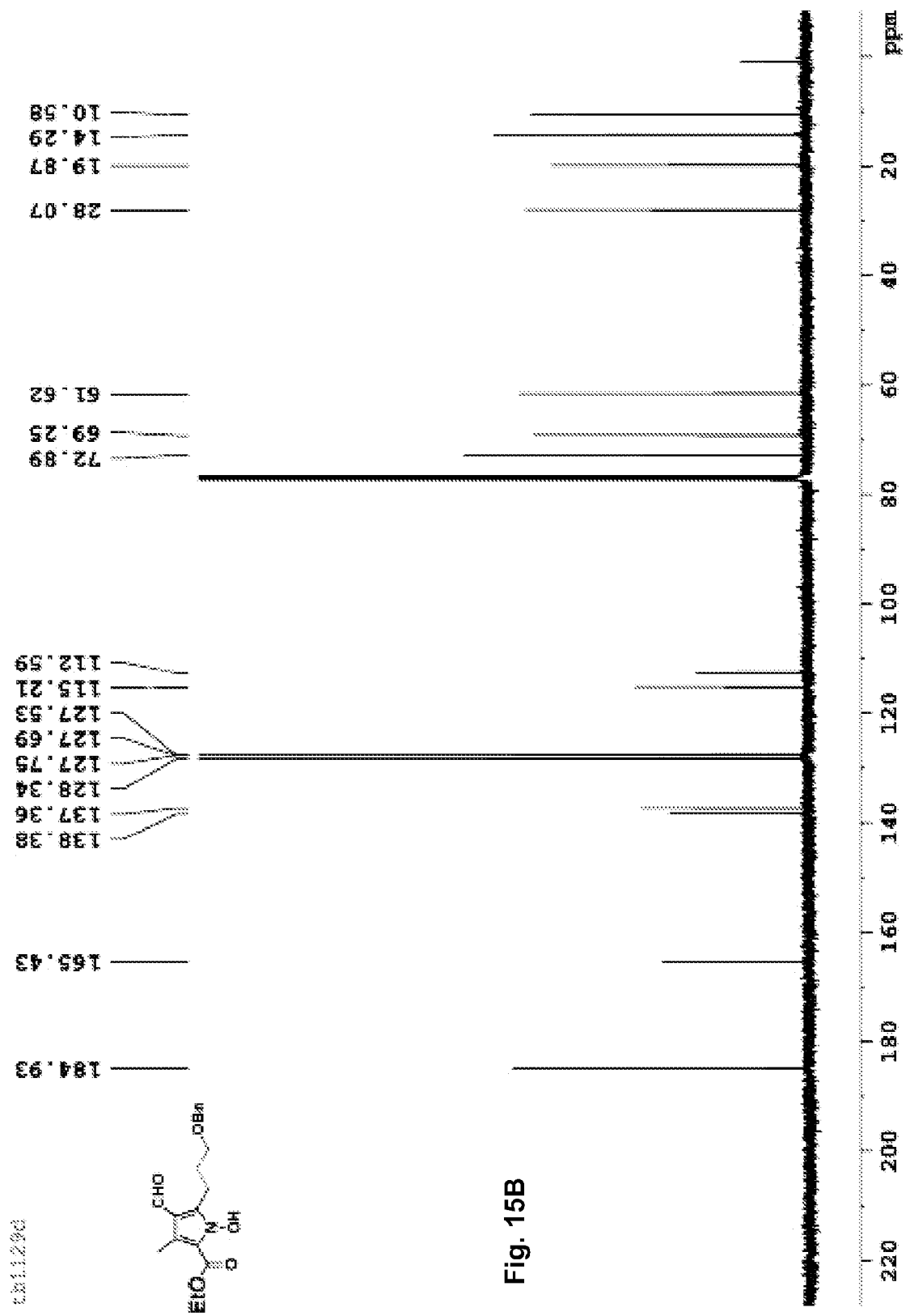
Figure 16A:
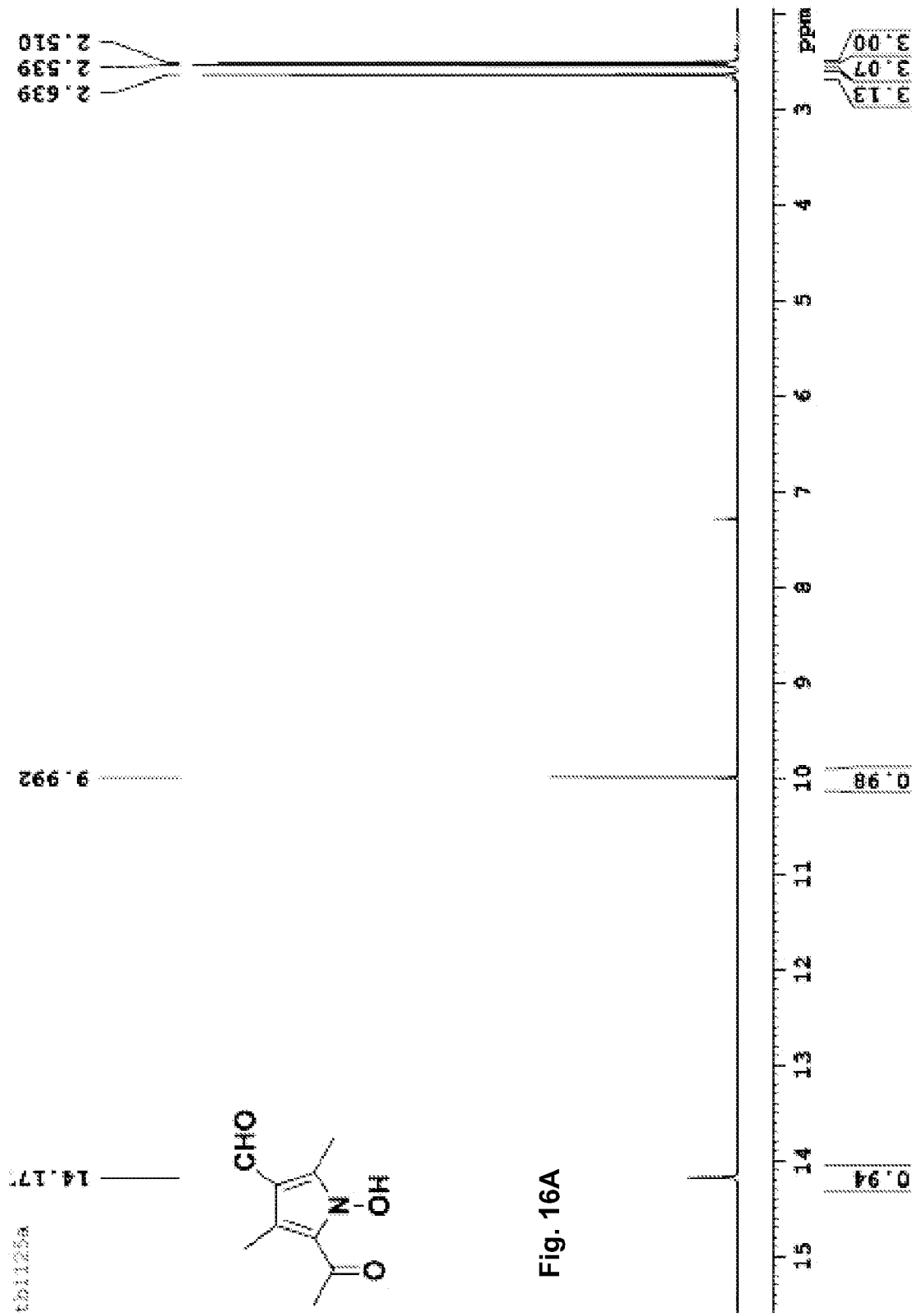
FIG. 16 depicts $^1$H NMR (A) and $^{13}$C NMR (B) spectra of compound 3g.
Figure 16B:
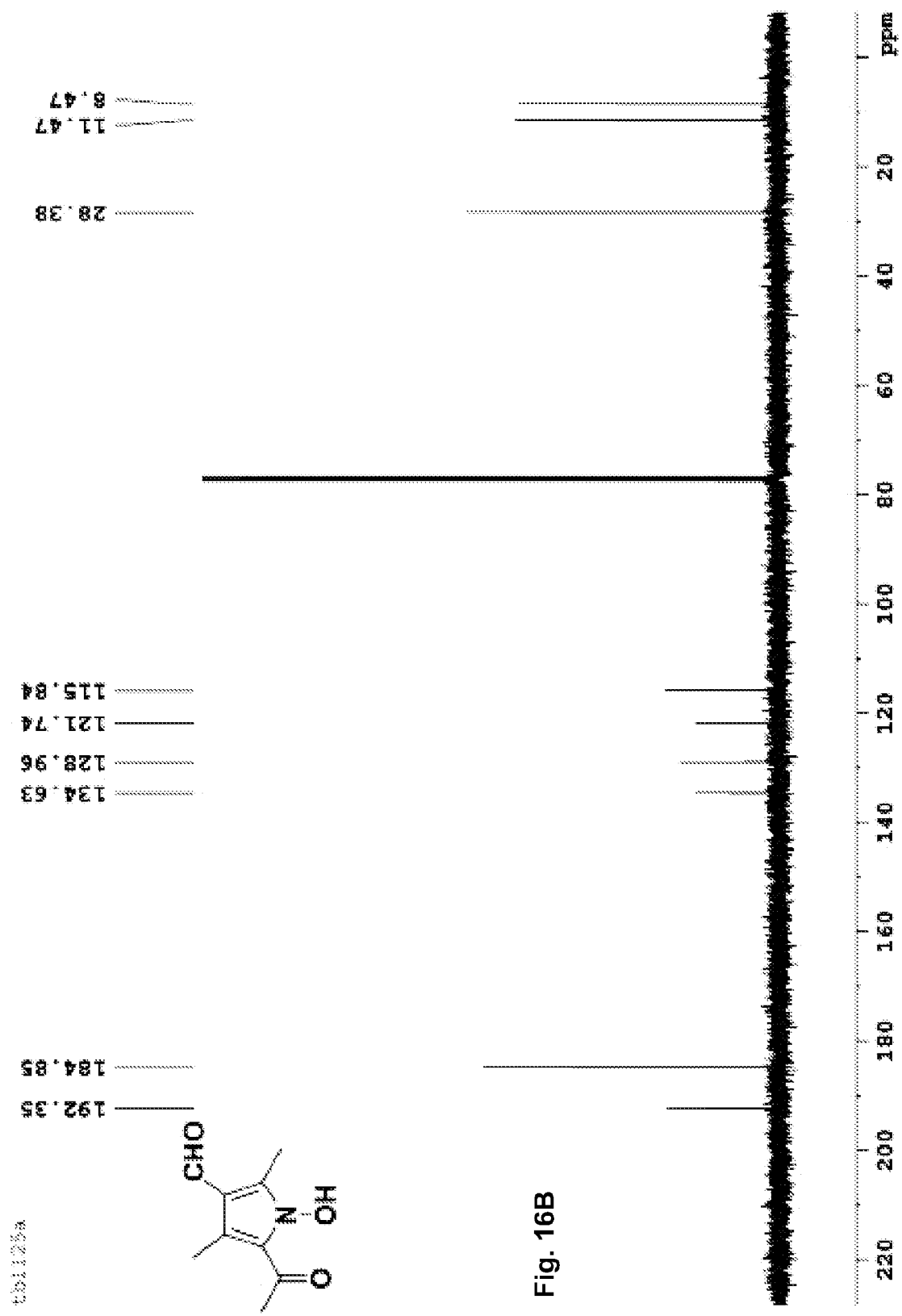
Figure 17A:
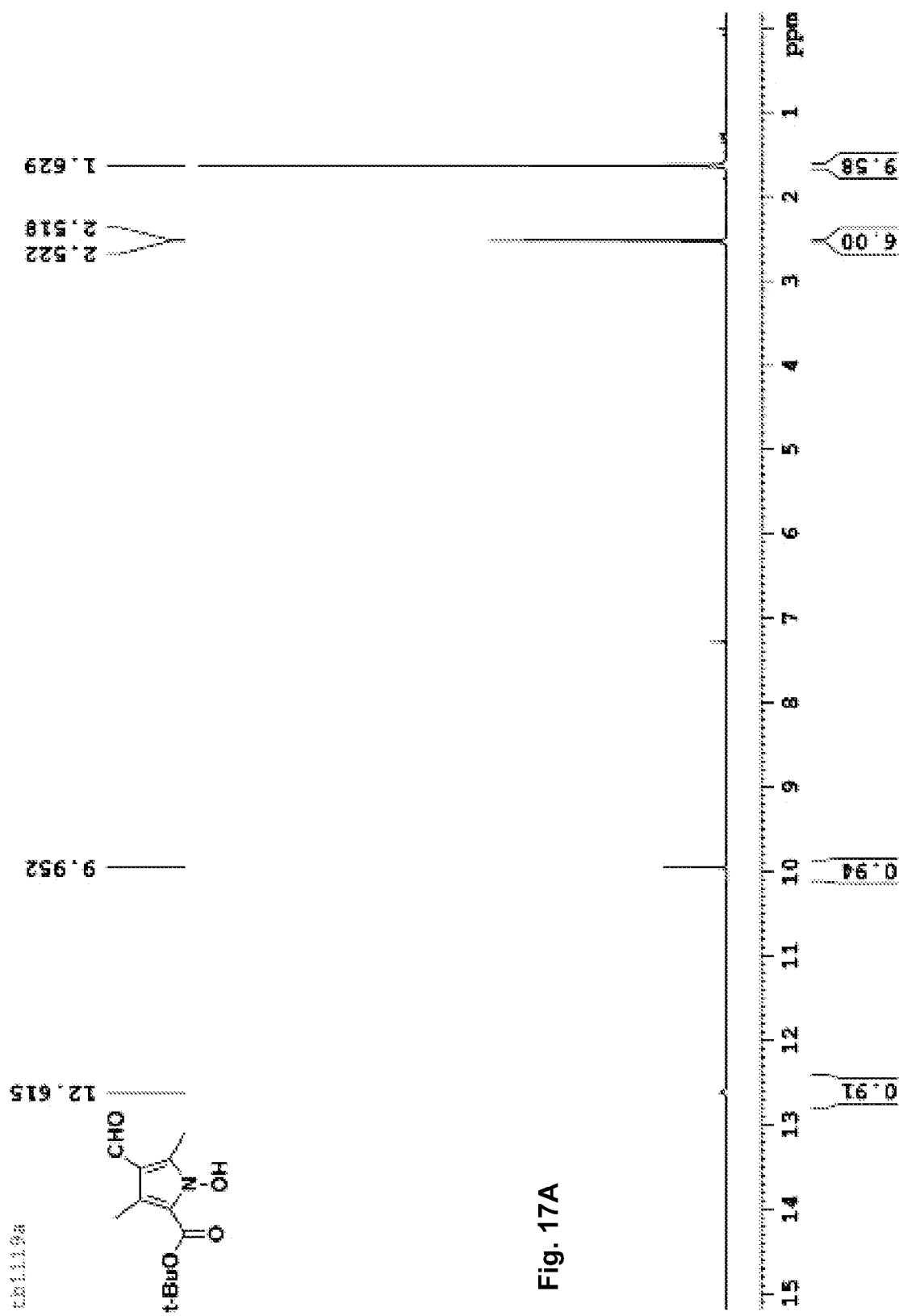
FIG. 17 depicts $^1$H NMR (A) and $^{13}$C NMR (B) spectra of compound 3h.
Figure 17B:
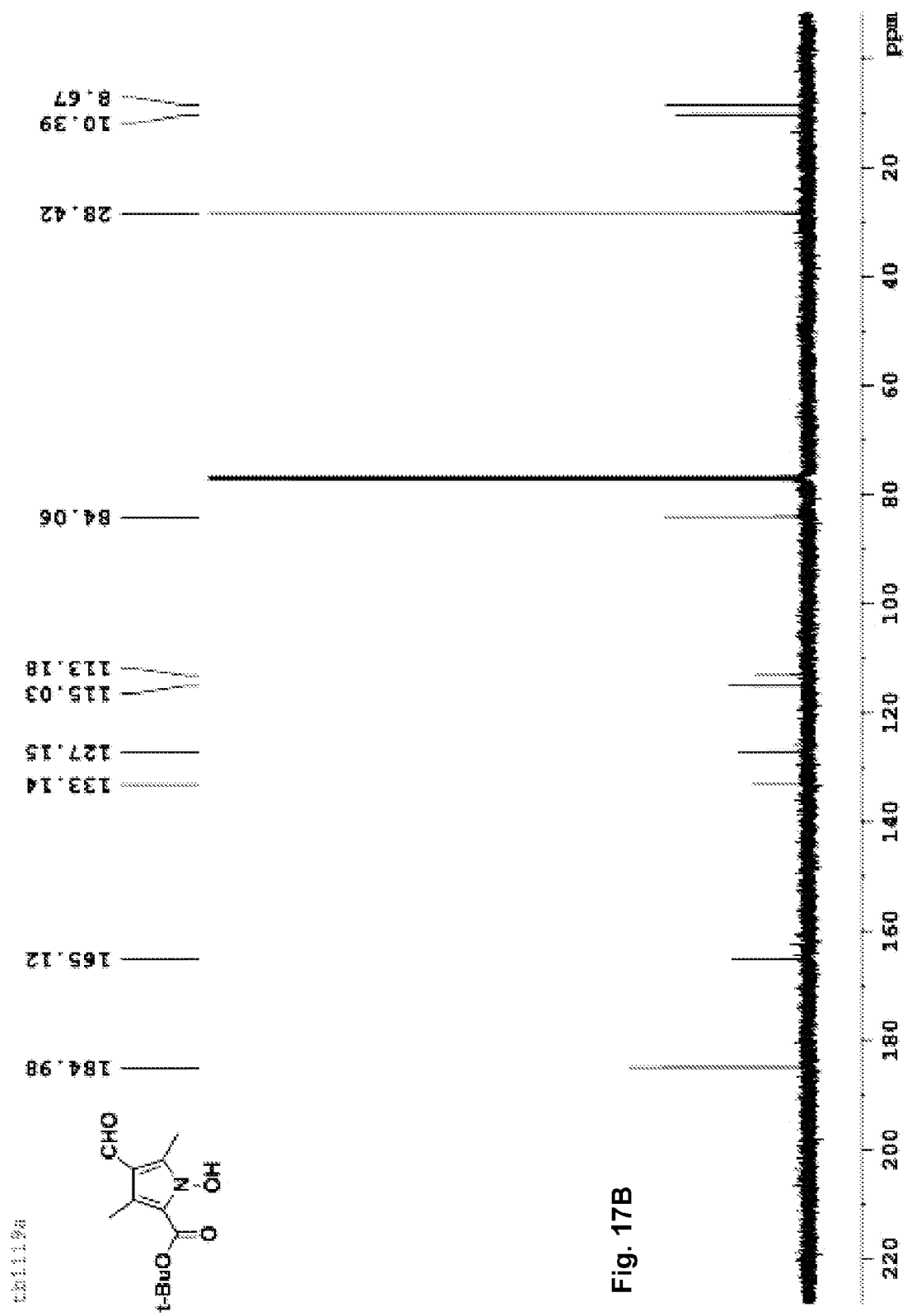
Figure 18A:
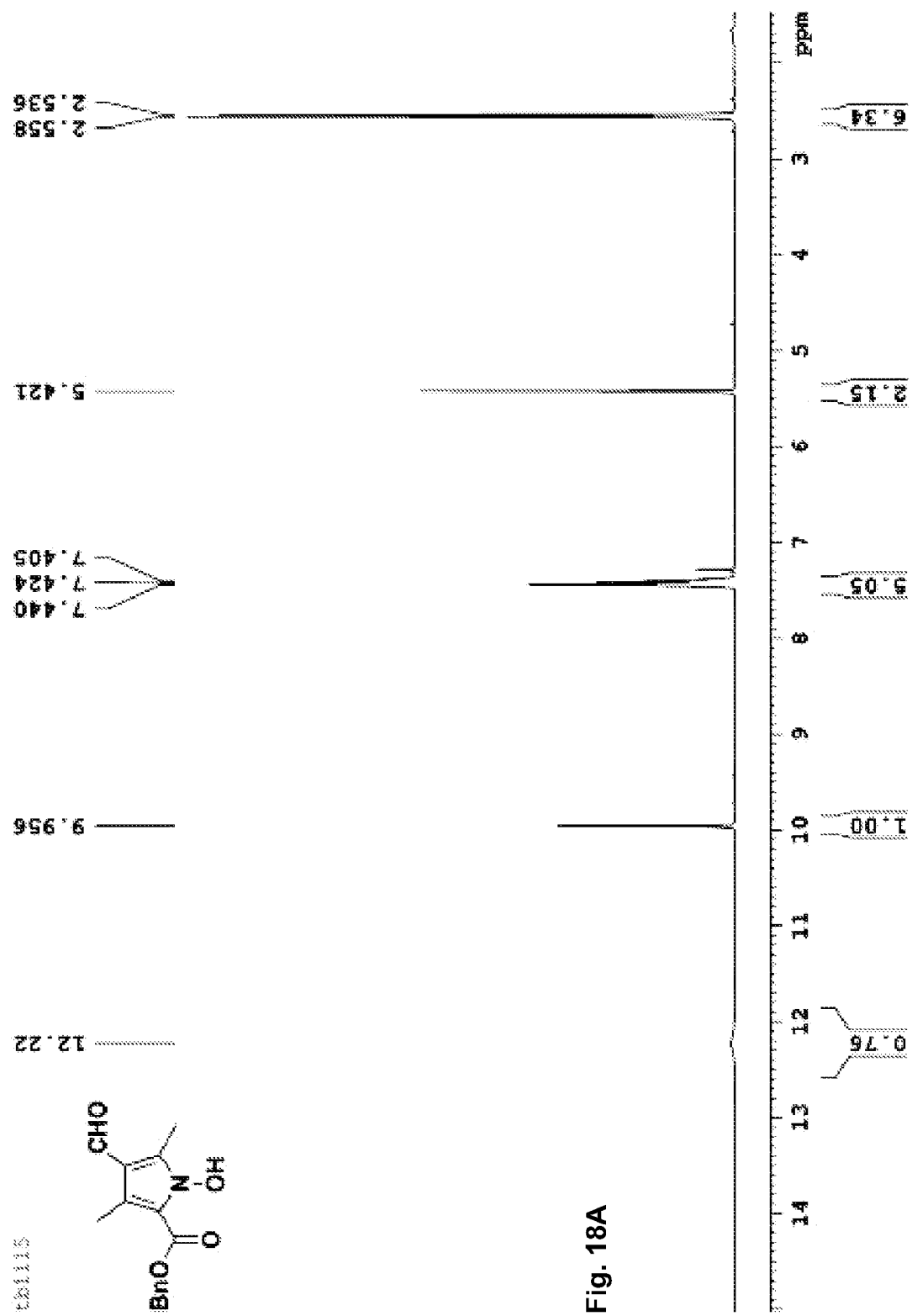
FIG. 18 depicts $^1$H NMR (A) and $^{13}$C NMR (B) spectra of compound 3i.
Figure 18B:
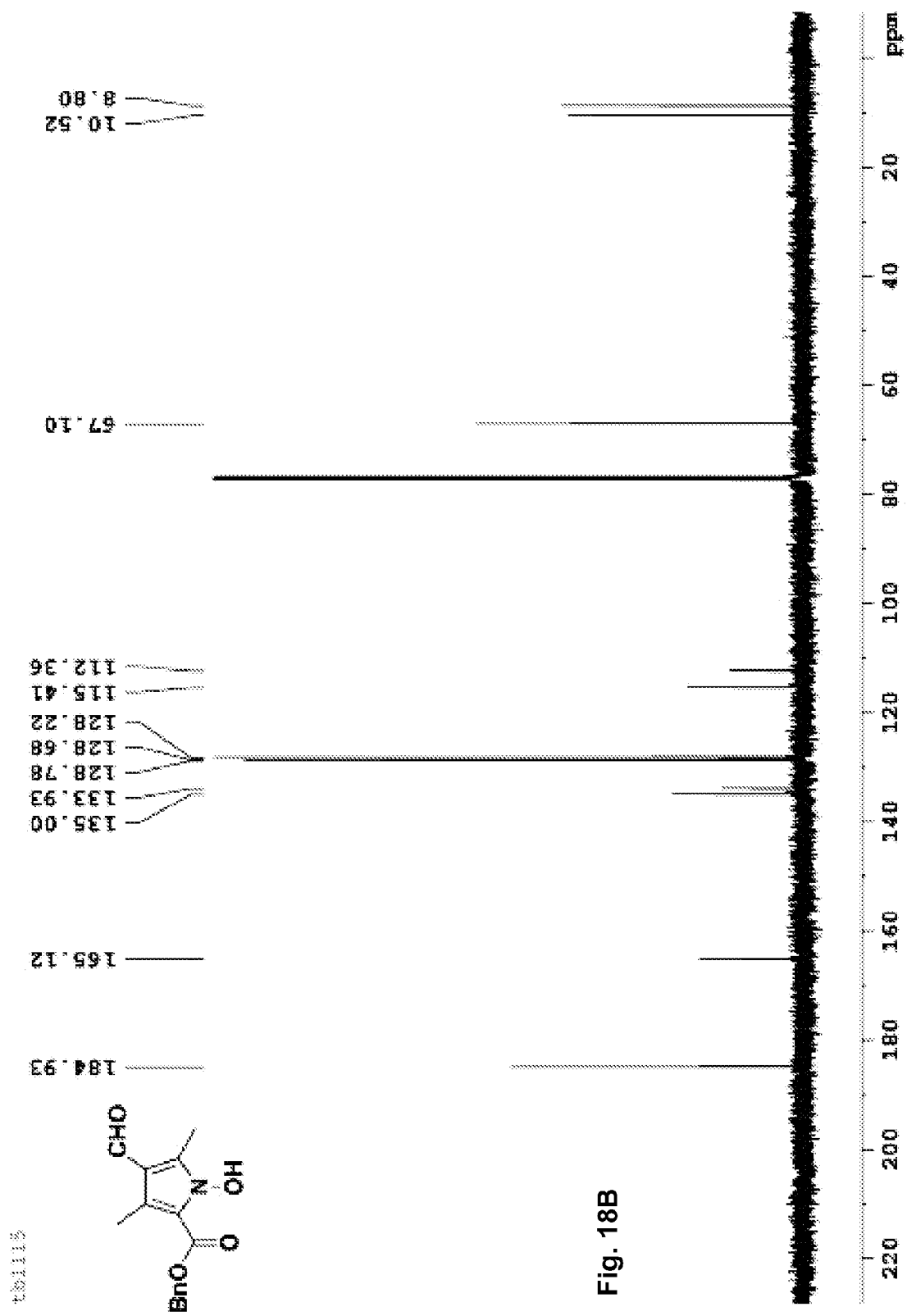
Figure 19A:
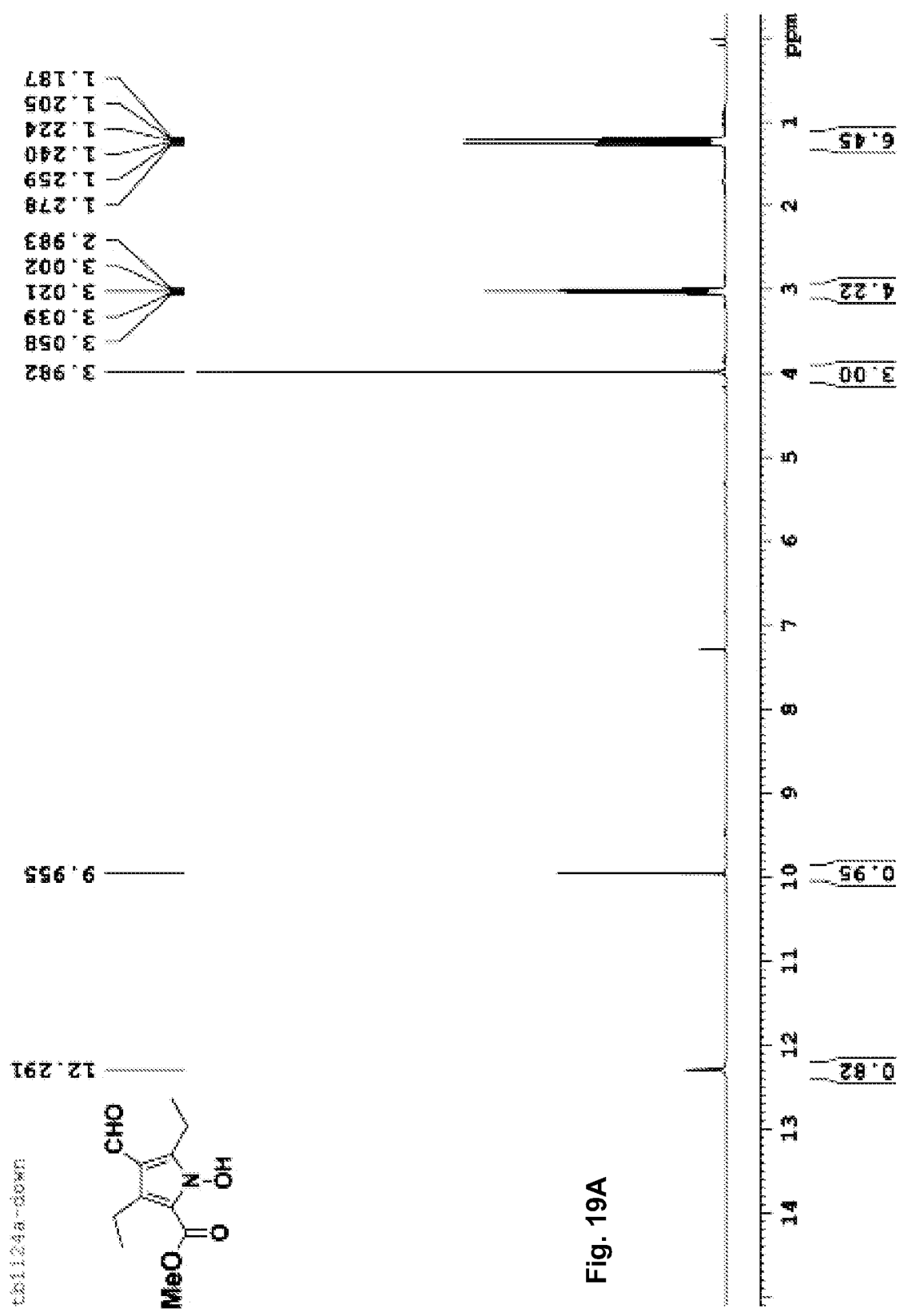
FIG. 19 depicts $^1$H NMR (A) and $^{13}$C NMR (B) spectra of compound 3k.
Figure 19B:
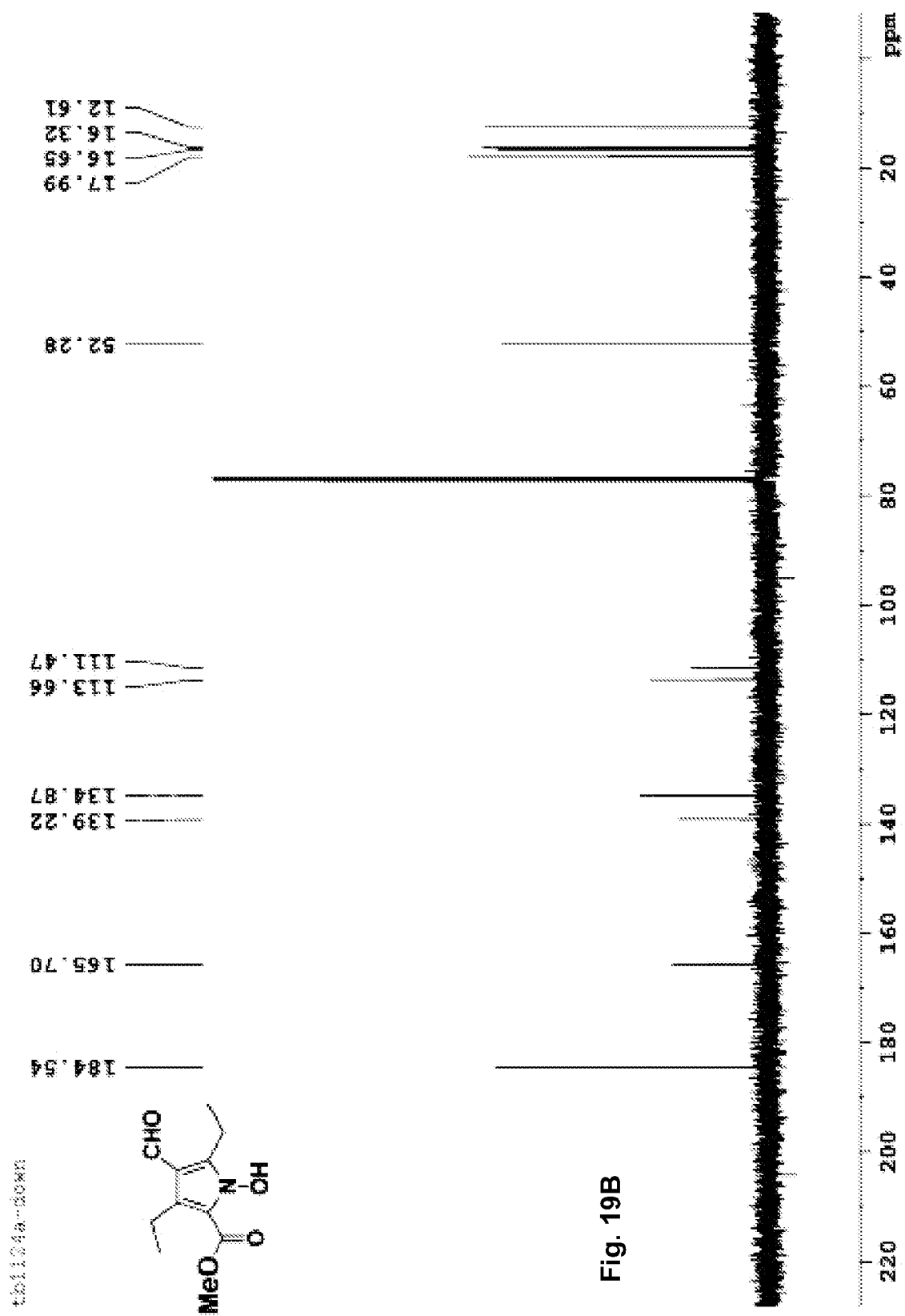
Figure 20A:
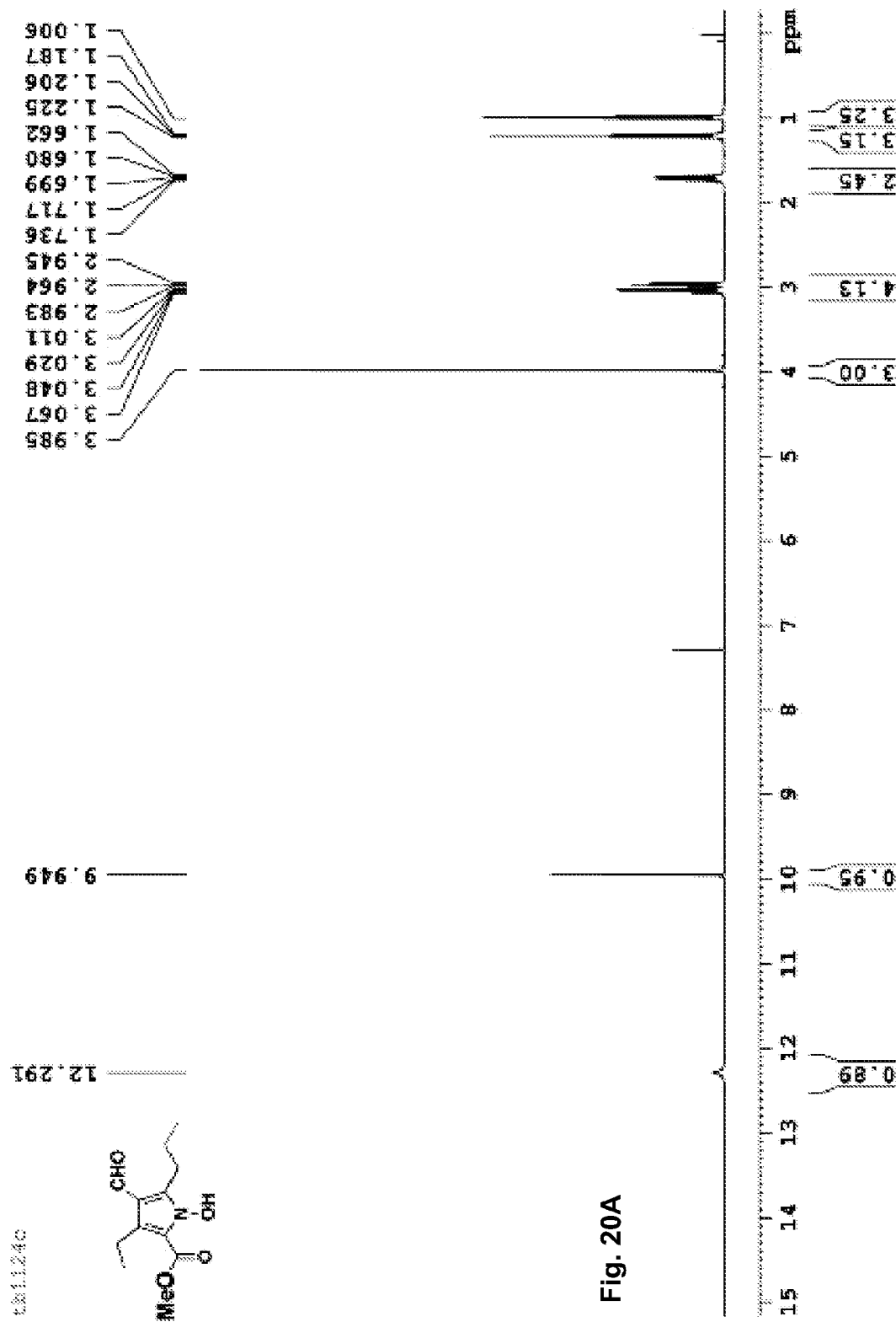
FIG. 20 depicts $^1$H NMR (A) and $^{13}$C NMR (B) spectra of compound 3l.
Figure 20B:
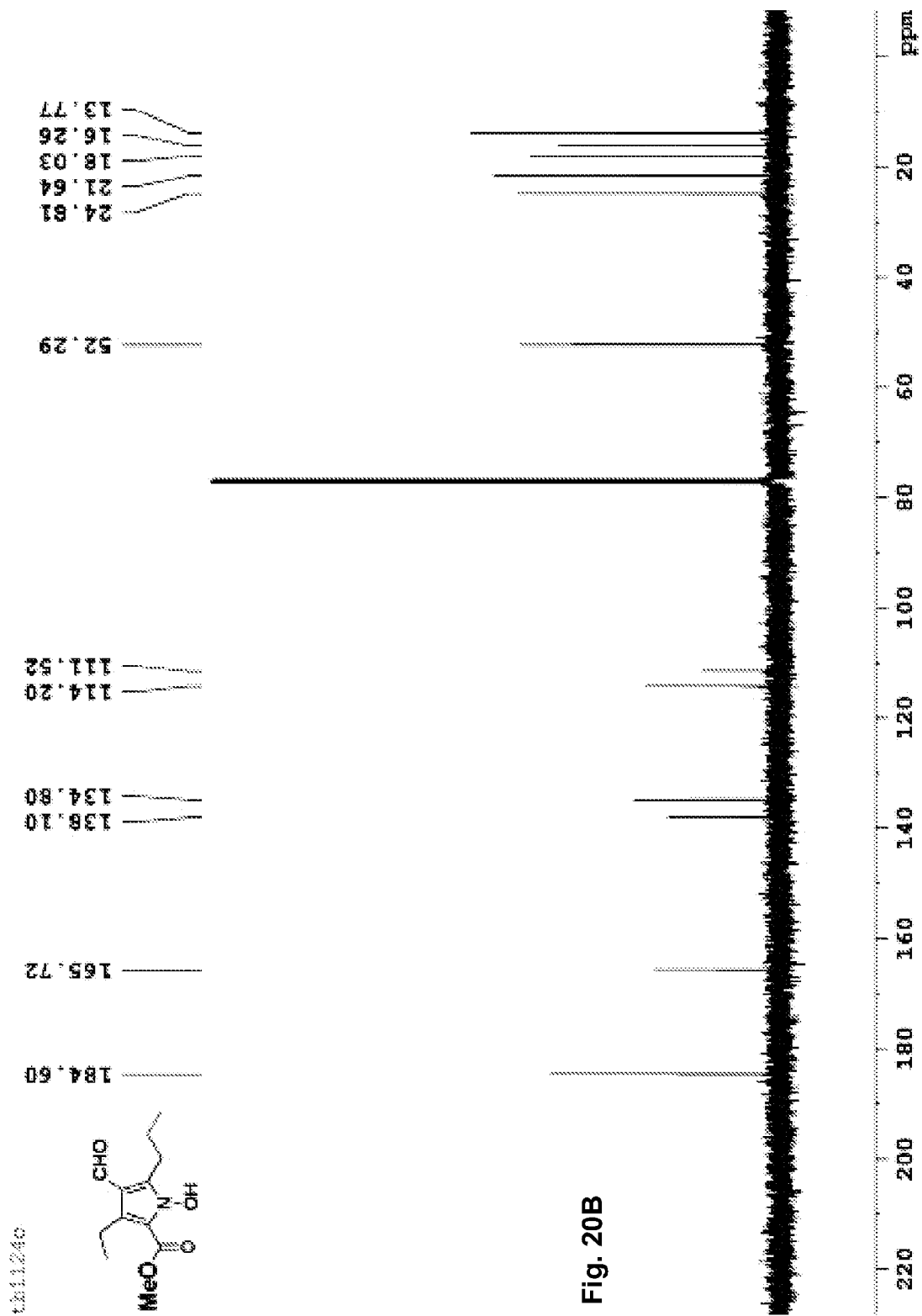
Figure 21A:
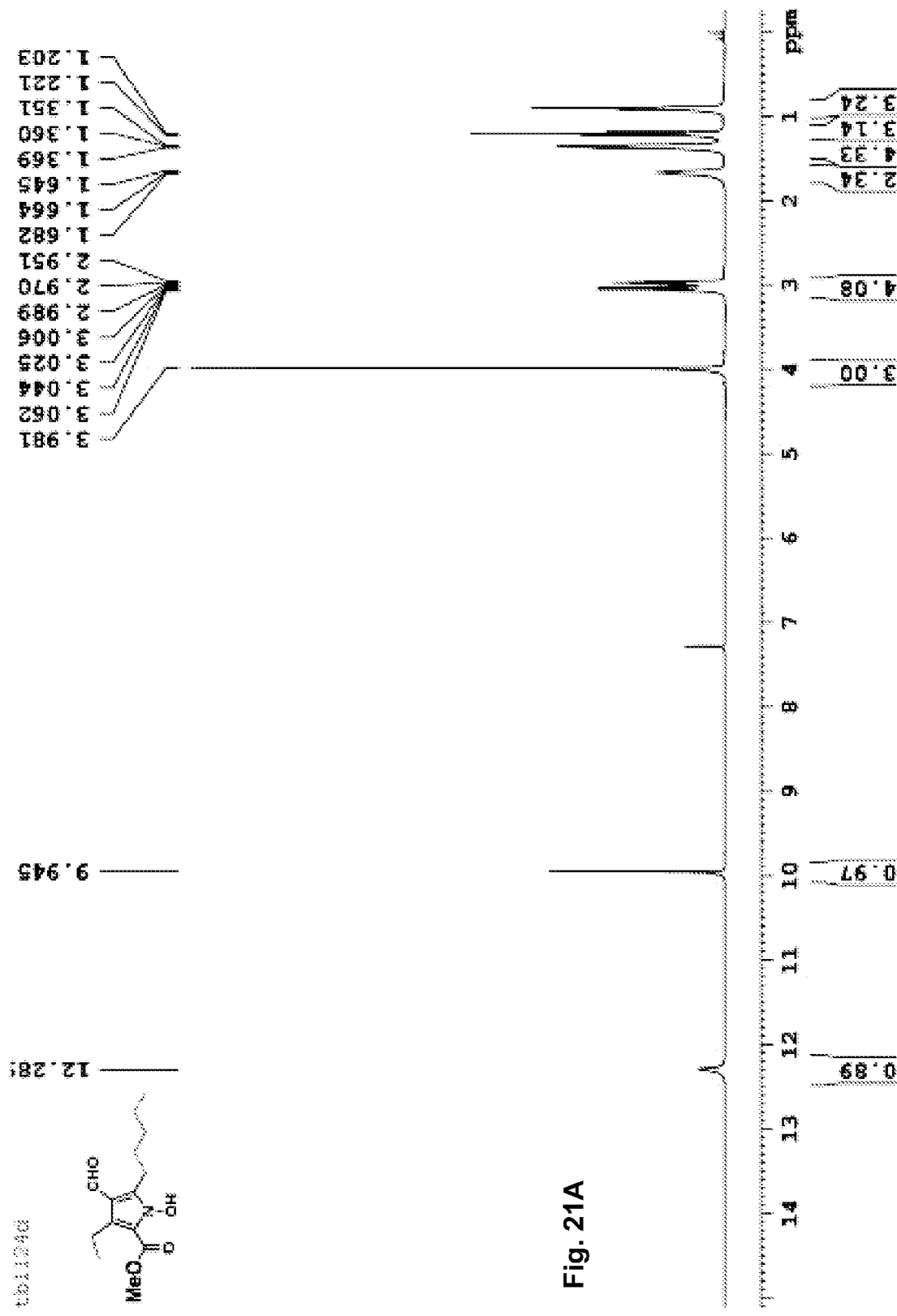
FIG. 21 depicts $^1$H NMR (A) and $^{13}$C NMR (B) spectra of compound 3m.
Figure 21B:
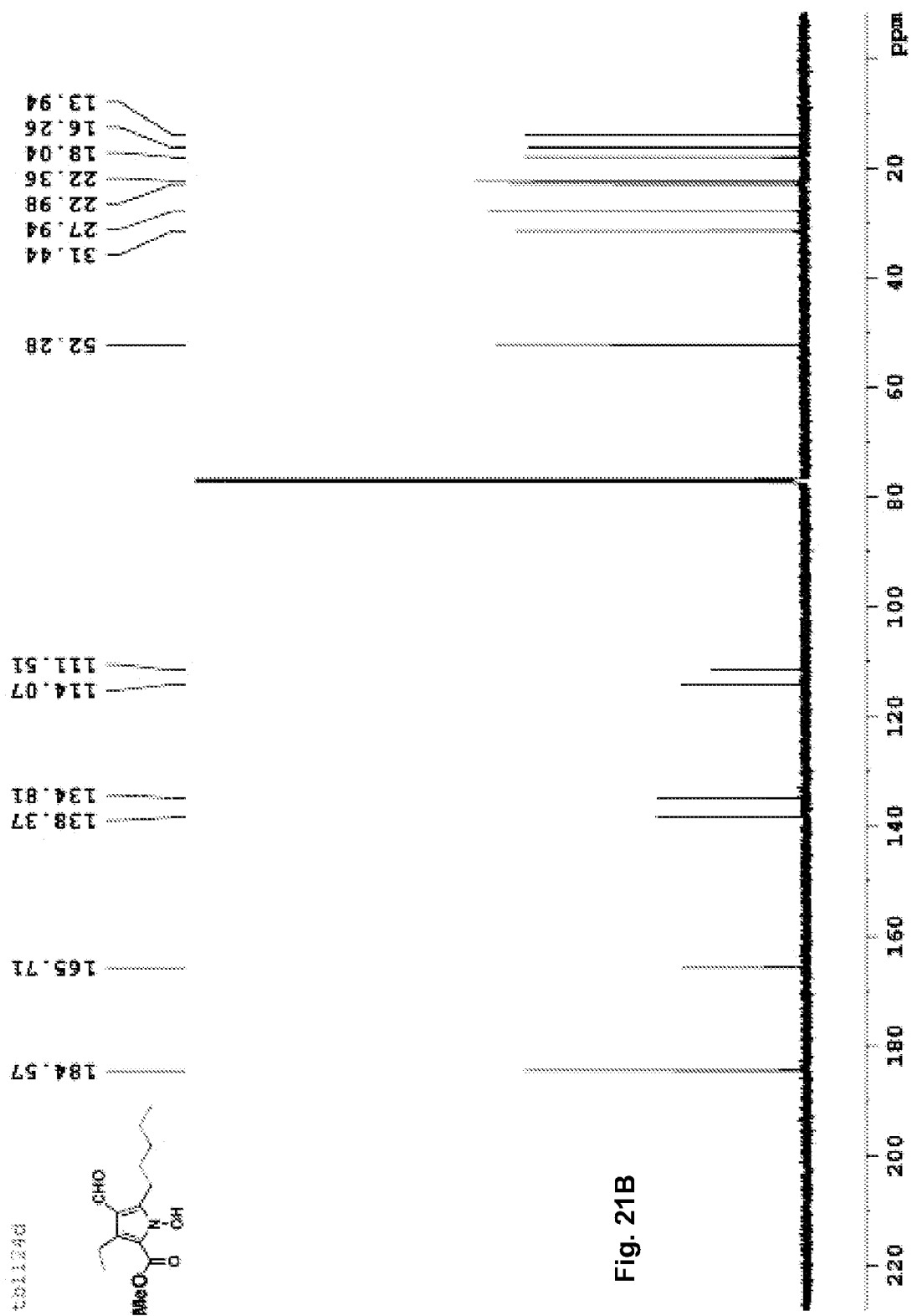
Figure 22A:
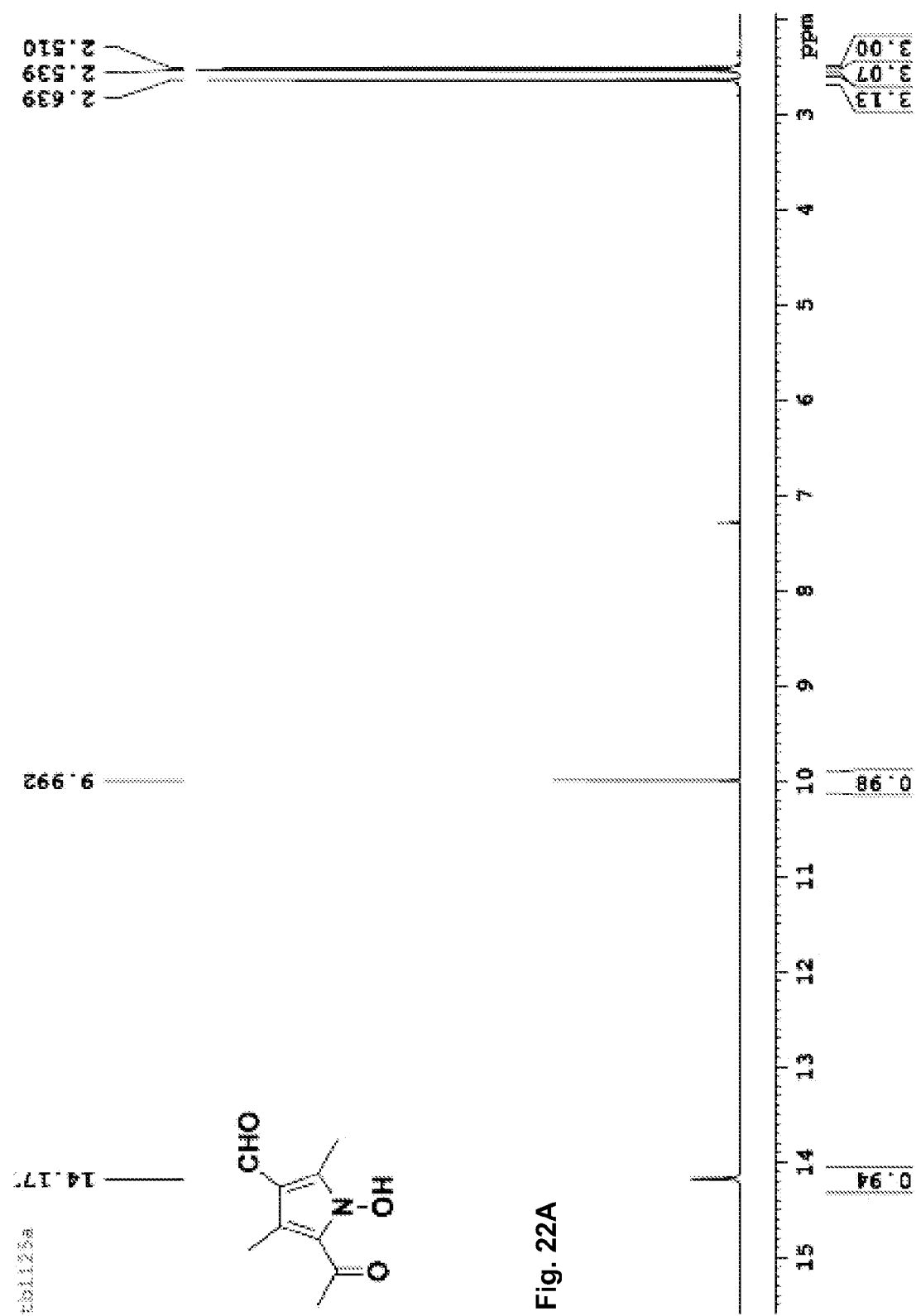
FIG. 22 depicts $^1$H NMR (A) and $^{13}$C NMR (B) spectra of compound 3n.
Figure 22B:
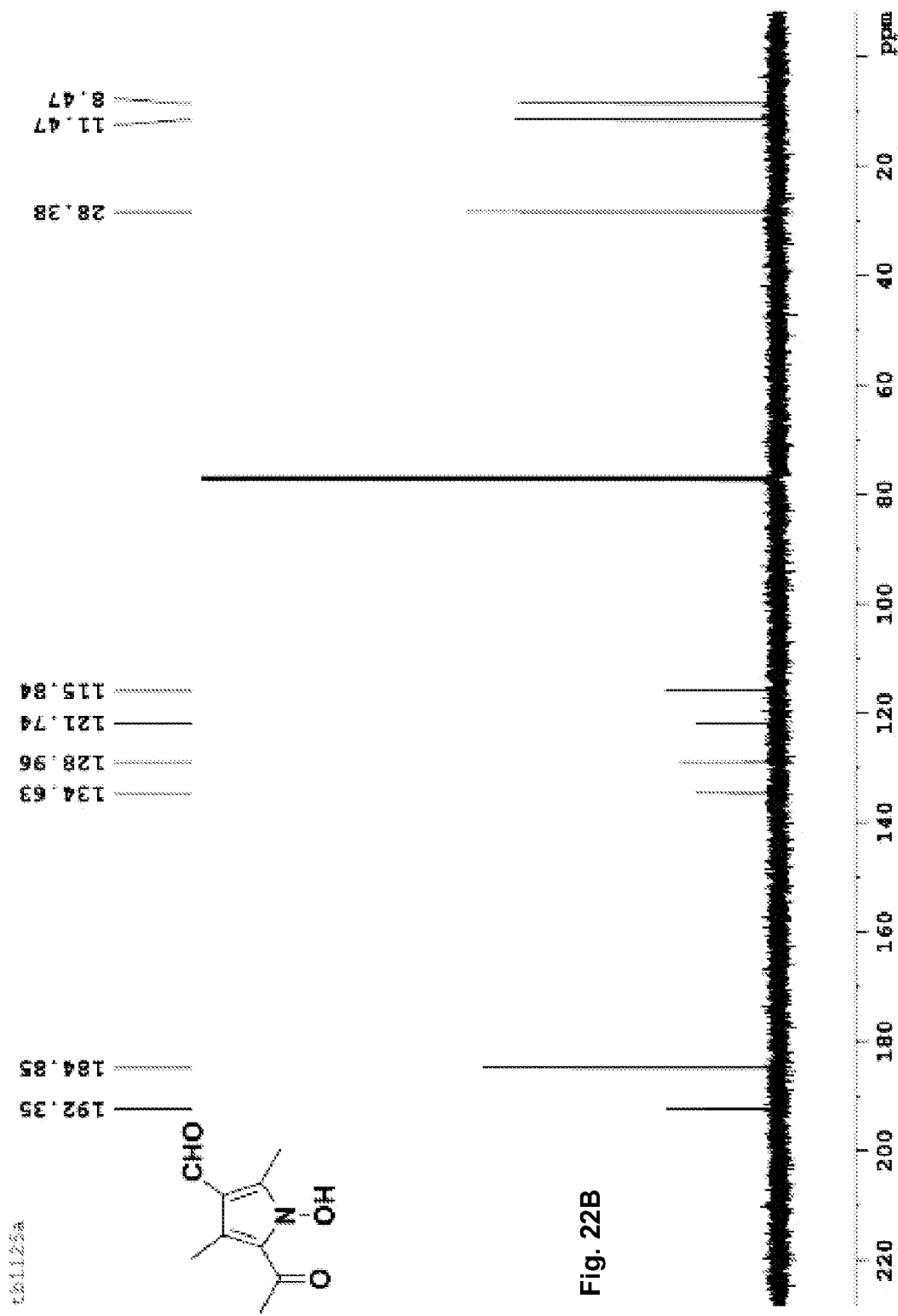
Figure 23A:
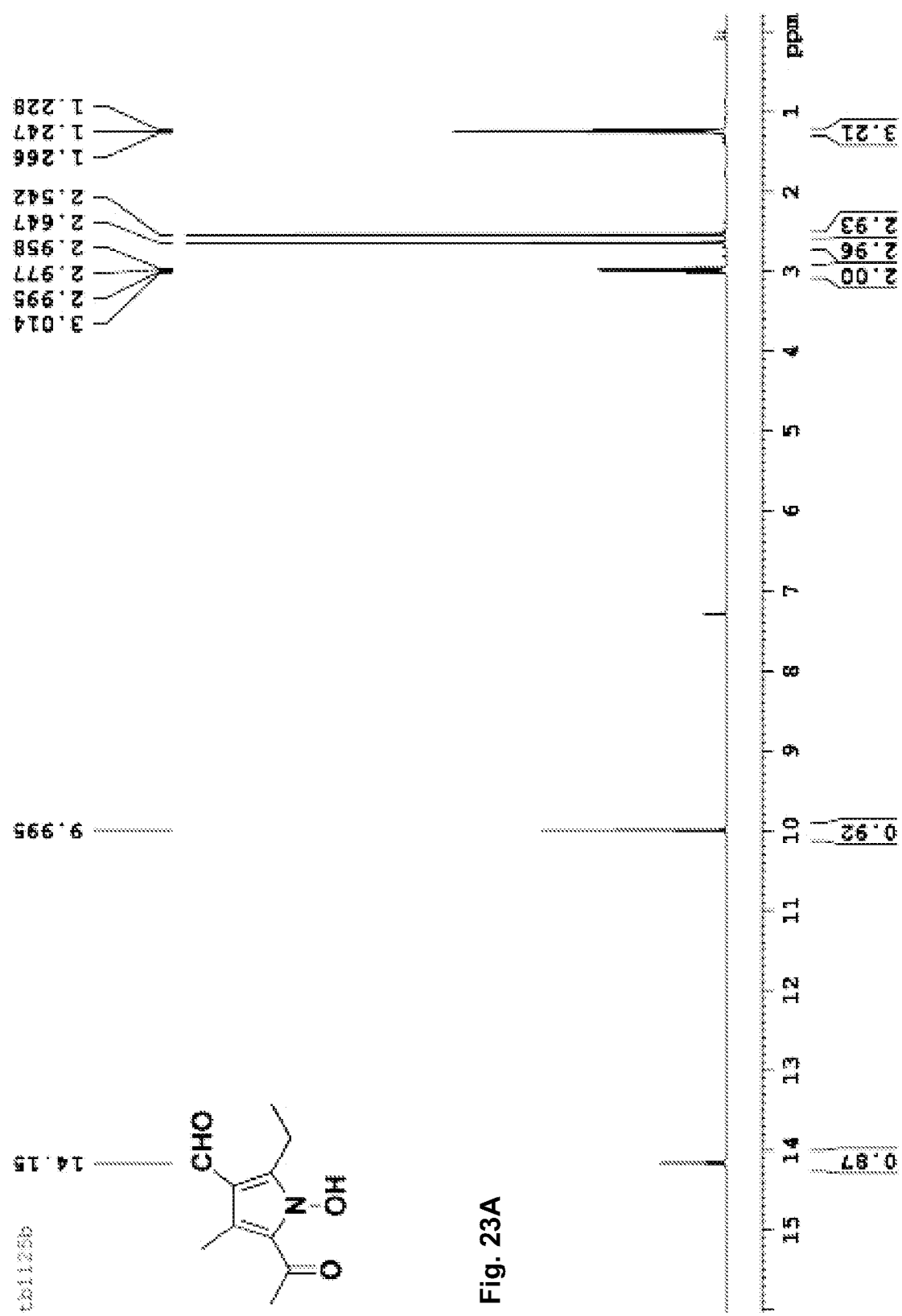
FIG. 23 depicts $^1$H NMR (A) and $^{13}$C NMR (B) spectra of compound 3o.
Figure 23B:
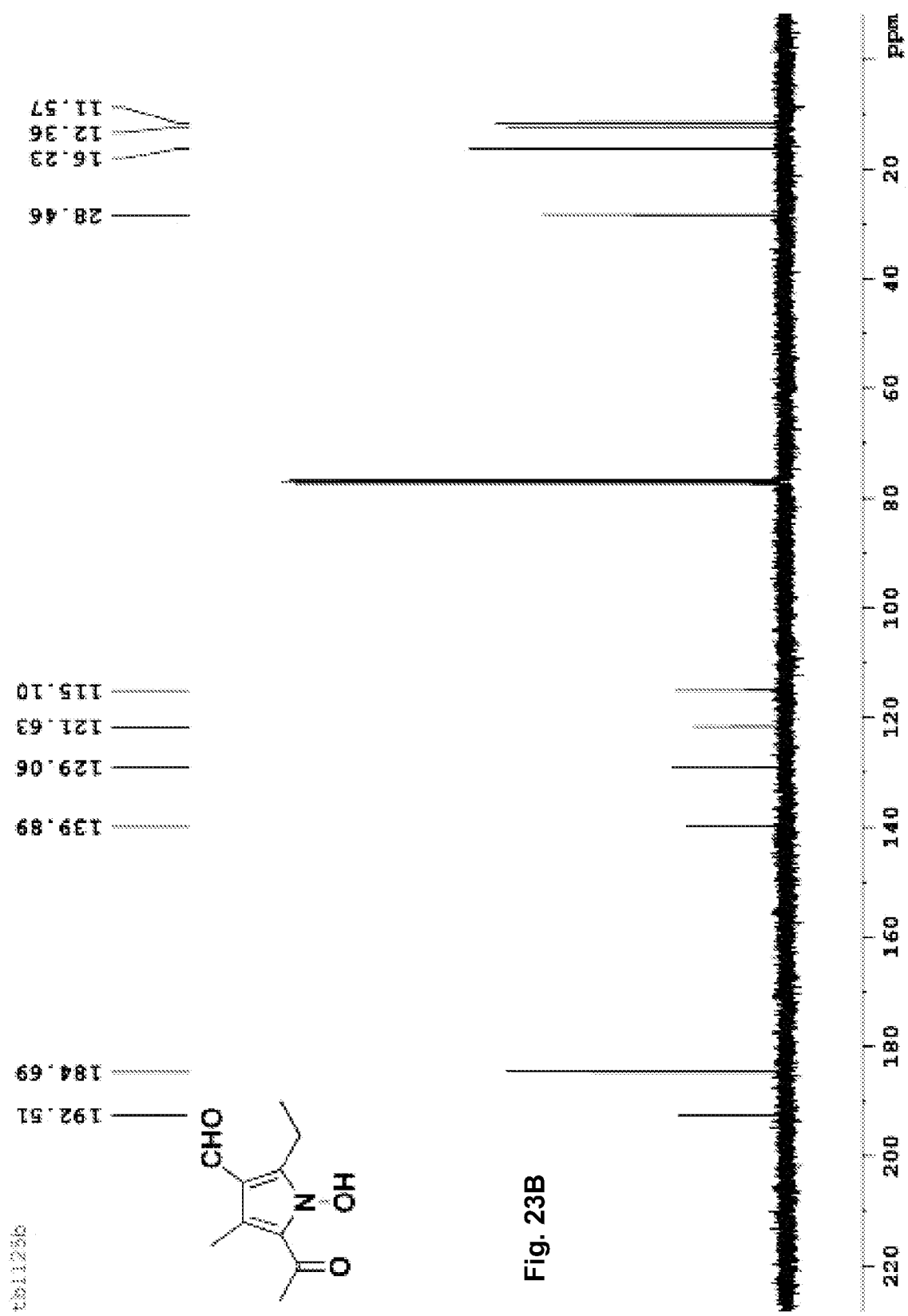
Figure 24A:
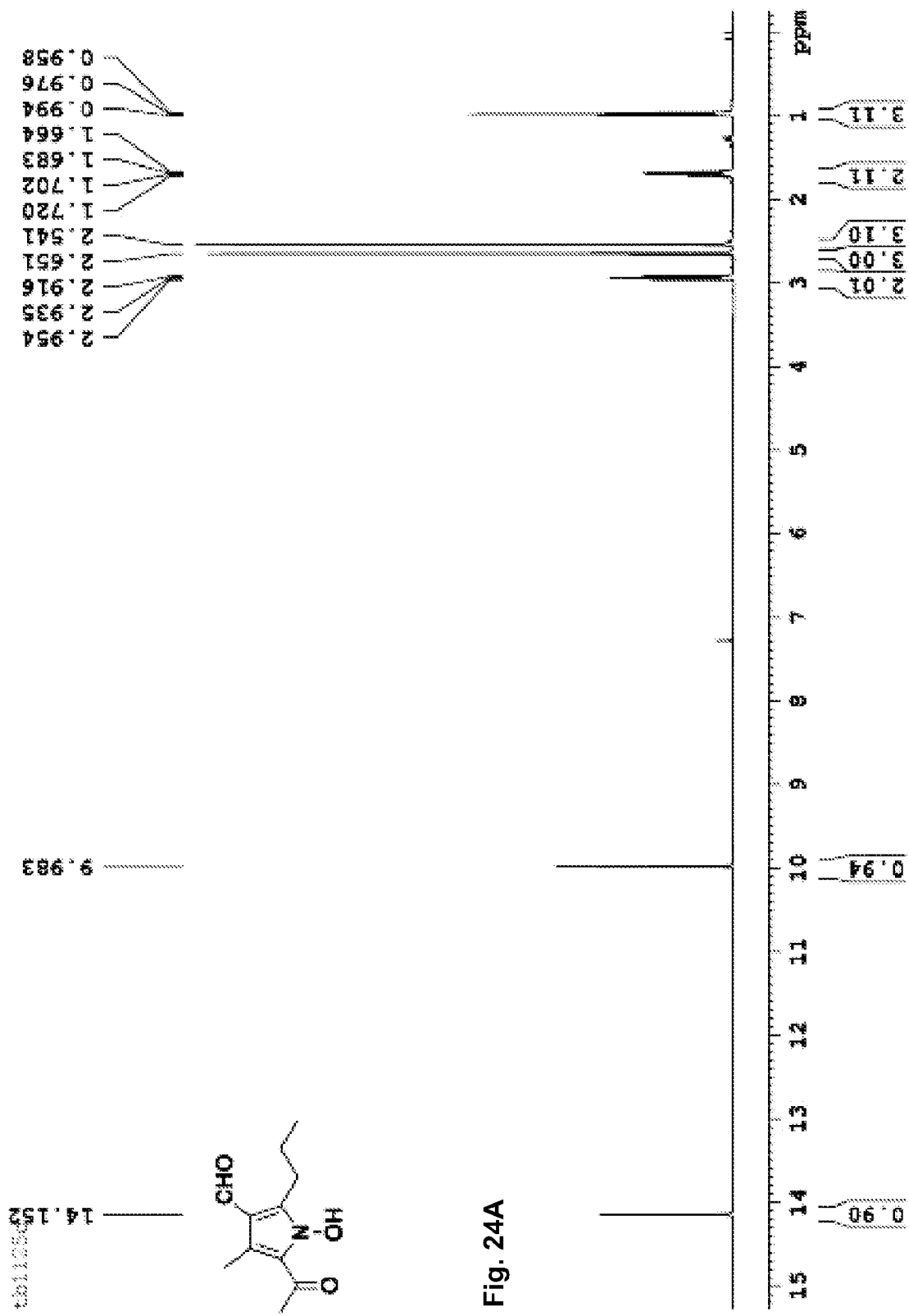
FIG. 24 depicts $^1$H NMR (A) and $^{13}$C NMR (B) spectra of compound 3p.
Figure 24B:
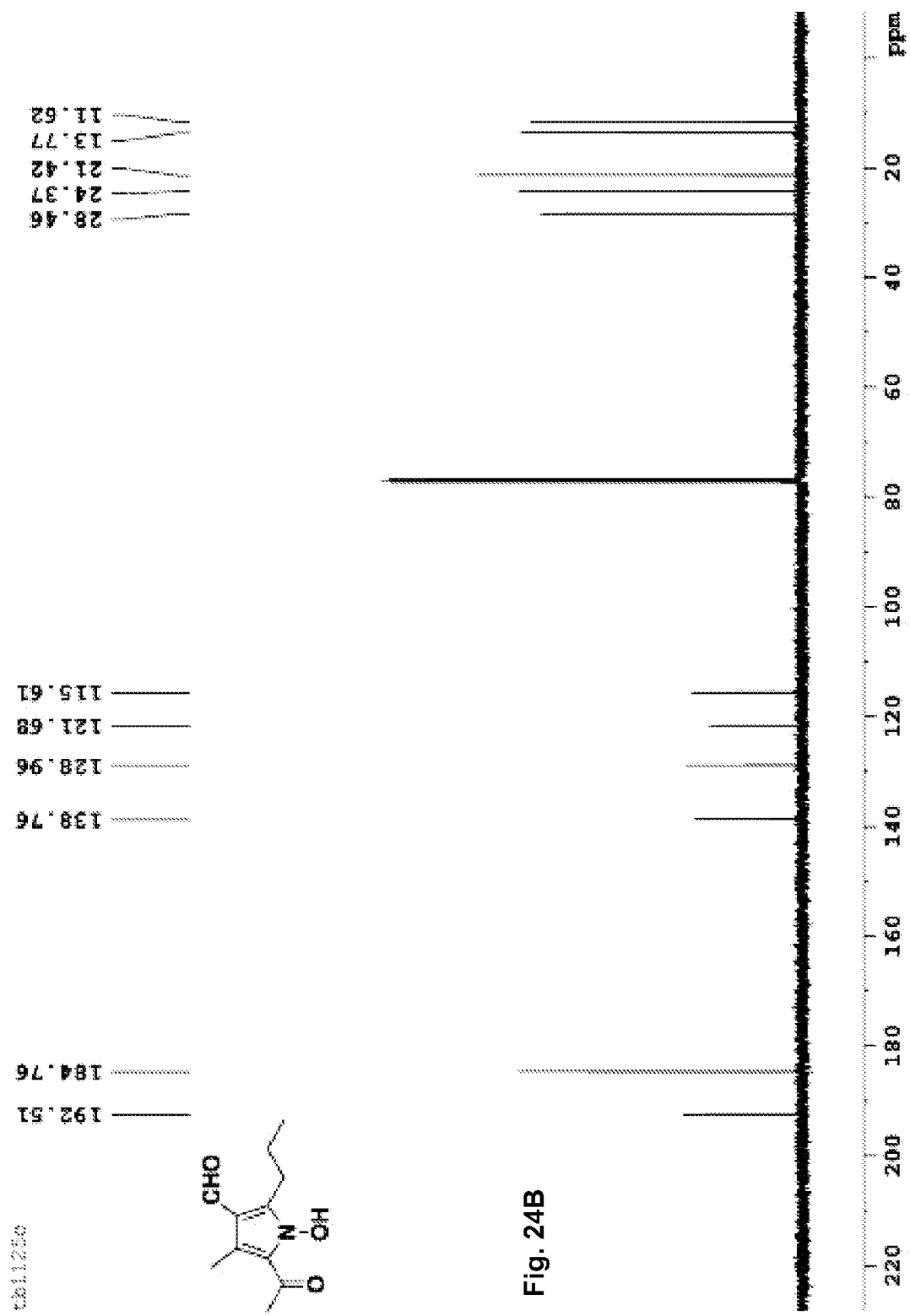
Figure 25A:
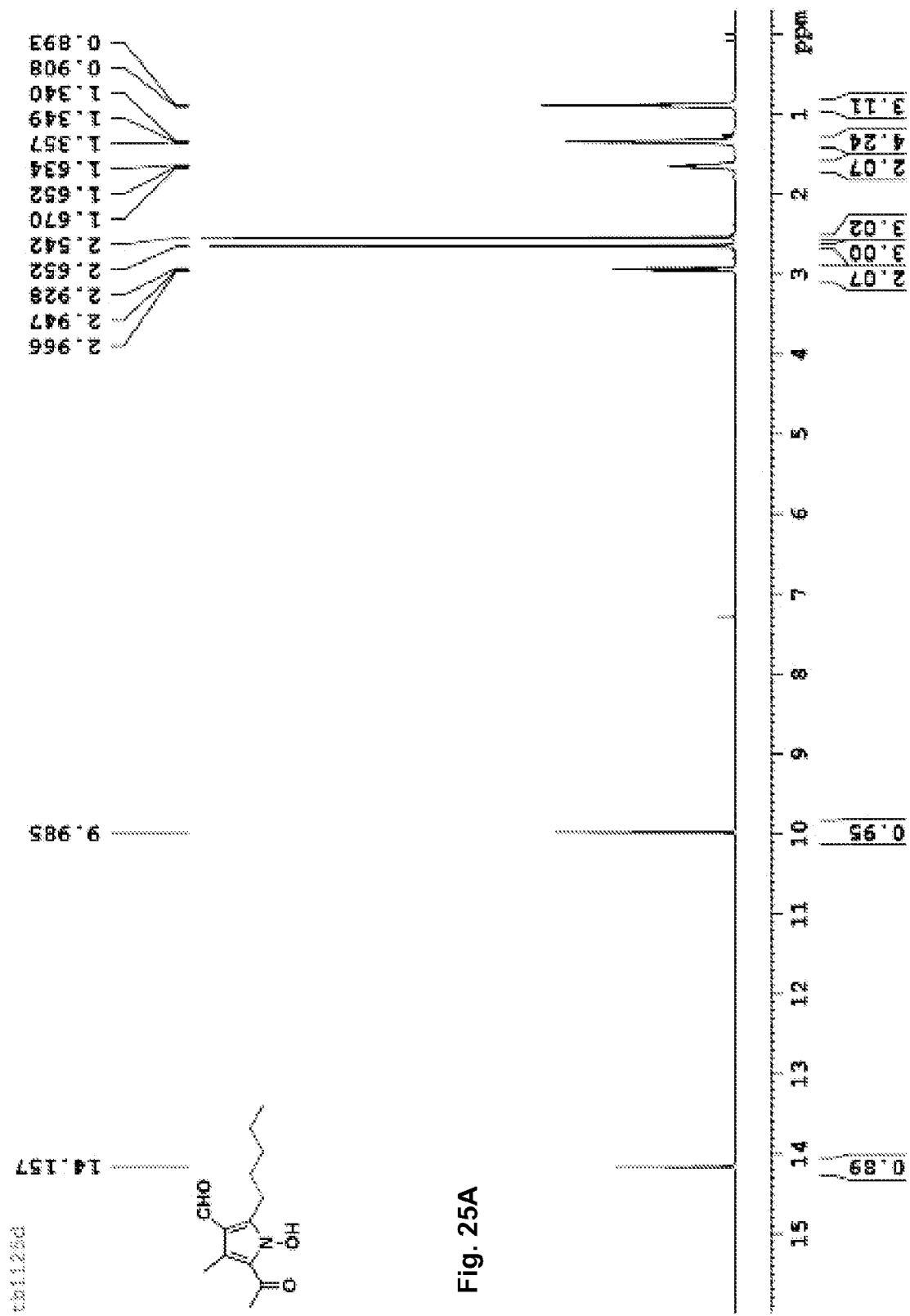
FIG. 25 depicts $^1$H NMR (A) and $^{13}$C NMR (B) spectra of compound 3q.
Figure 25B:
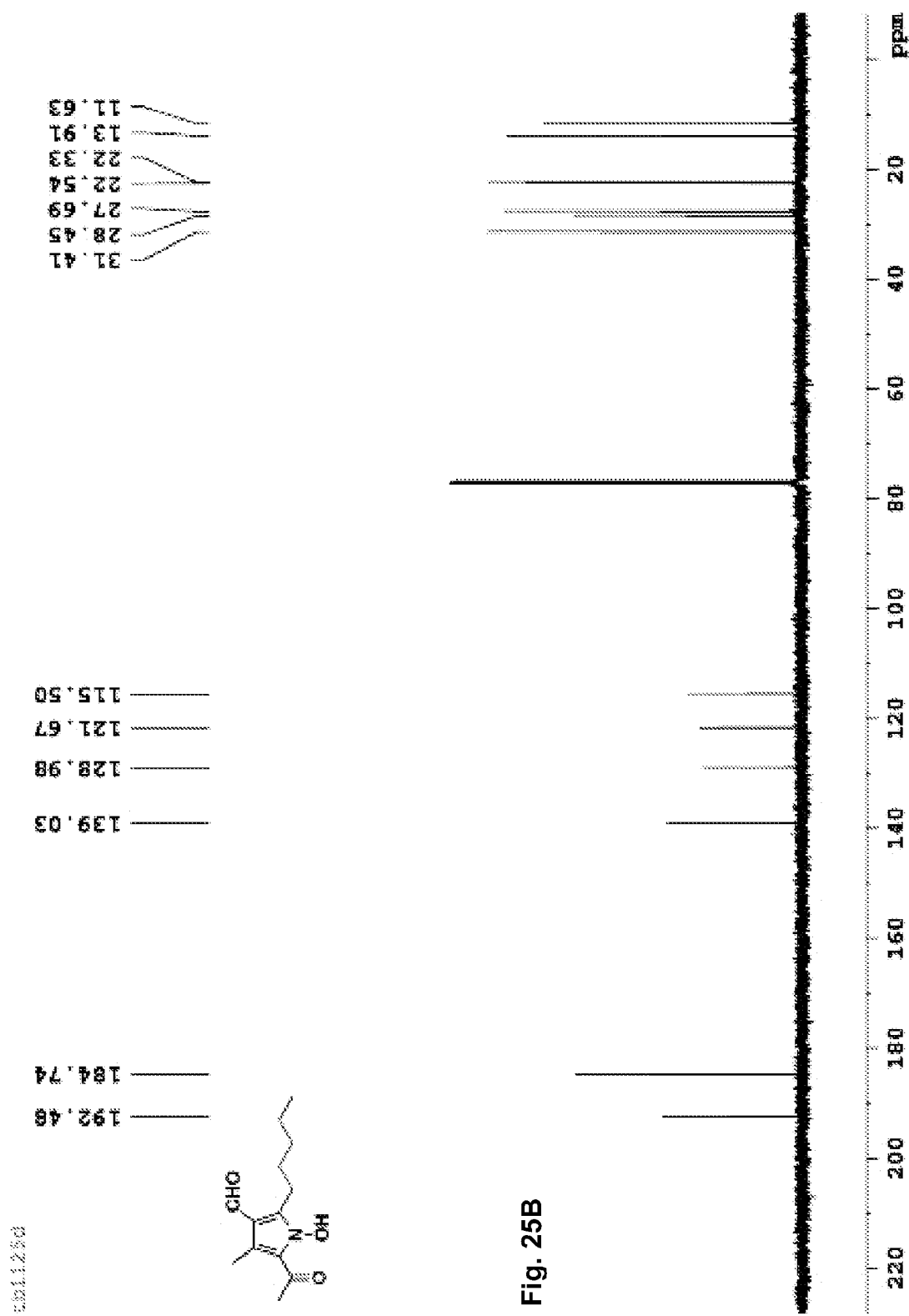
Figure 26A:
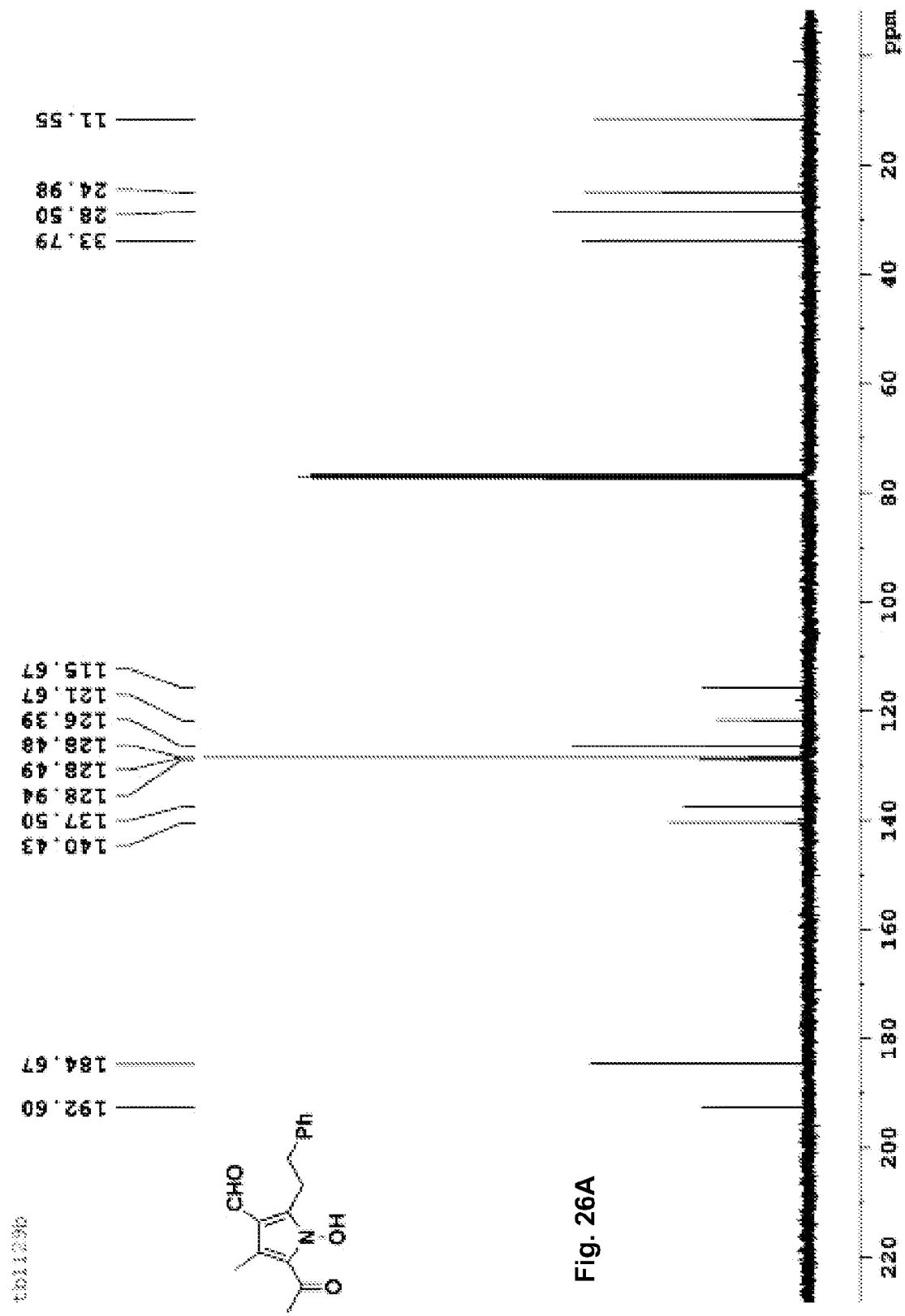
FIG. 26 depicts $^1$H NMR (A) and $^{13}$C NMR (B) spectra of compound 3r.
Figure 26B:
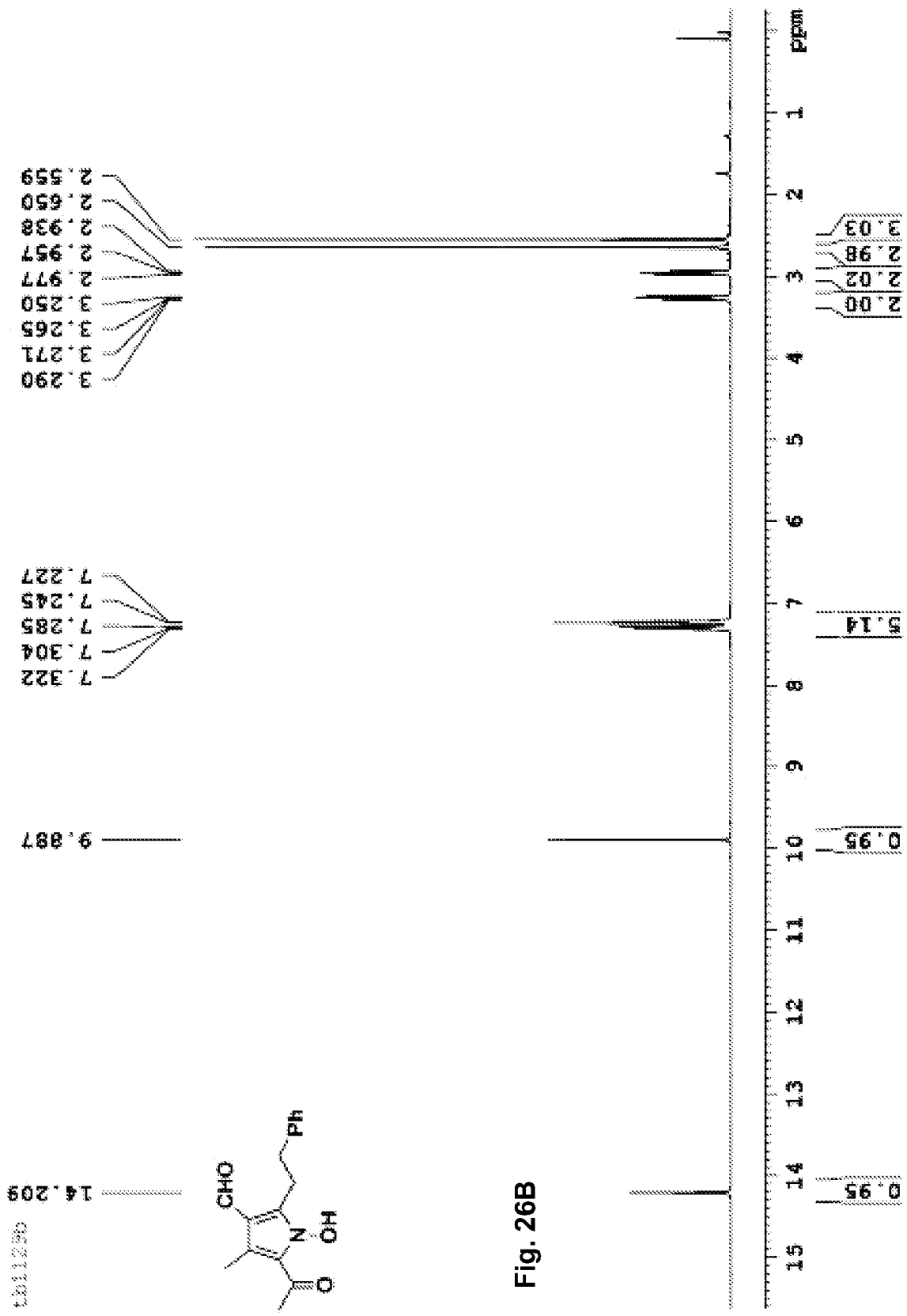
Figure 27A:
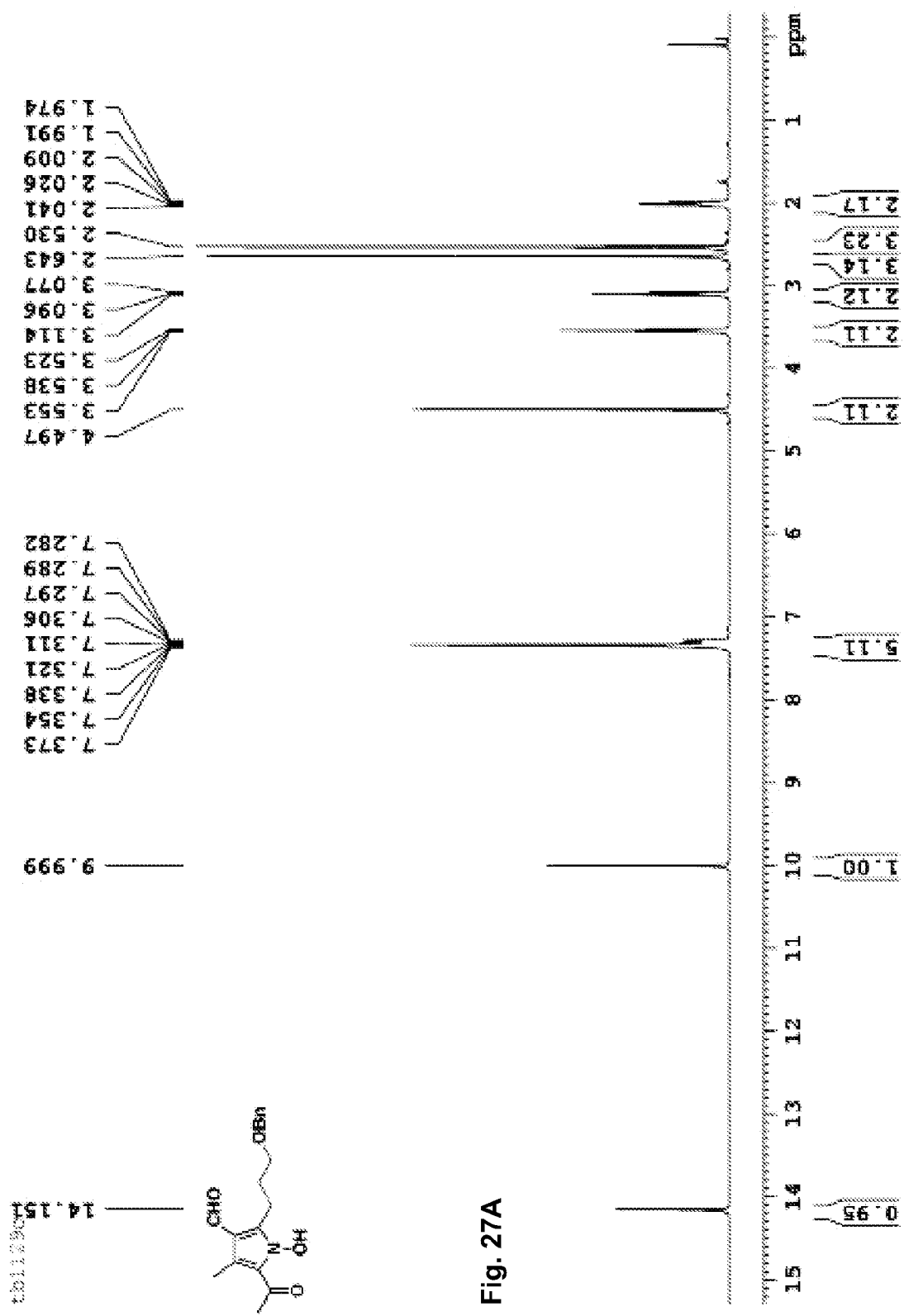
FIG. 27 depicts $^1$H NMR (A) and $^{13}$C NMR (B) spectra of compound 3s.
Figure 27B:
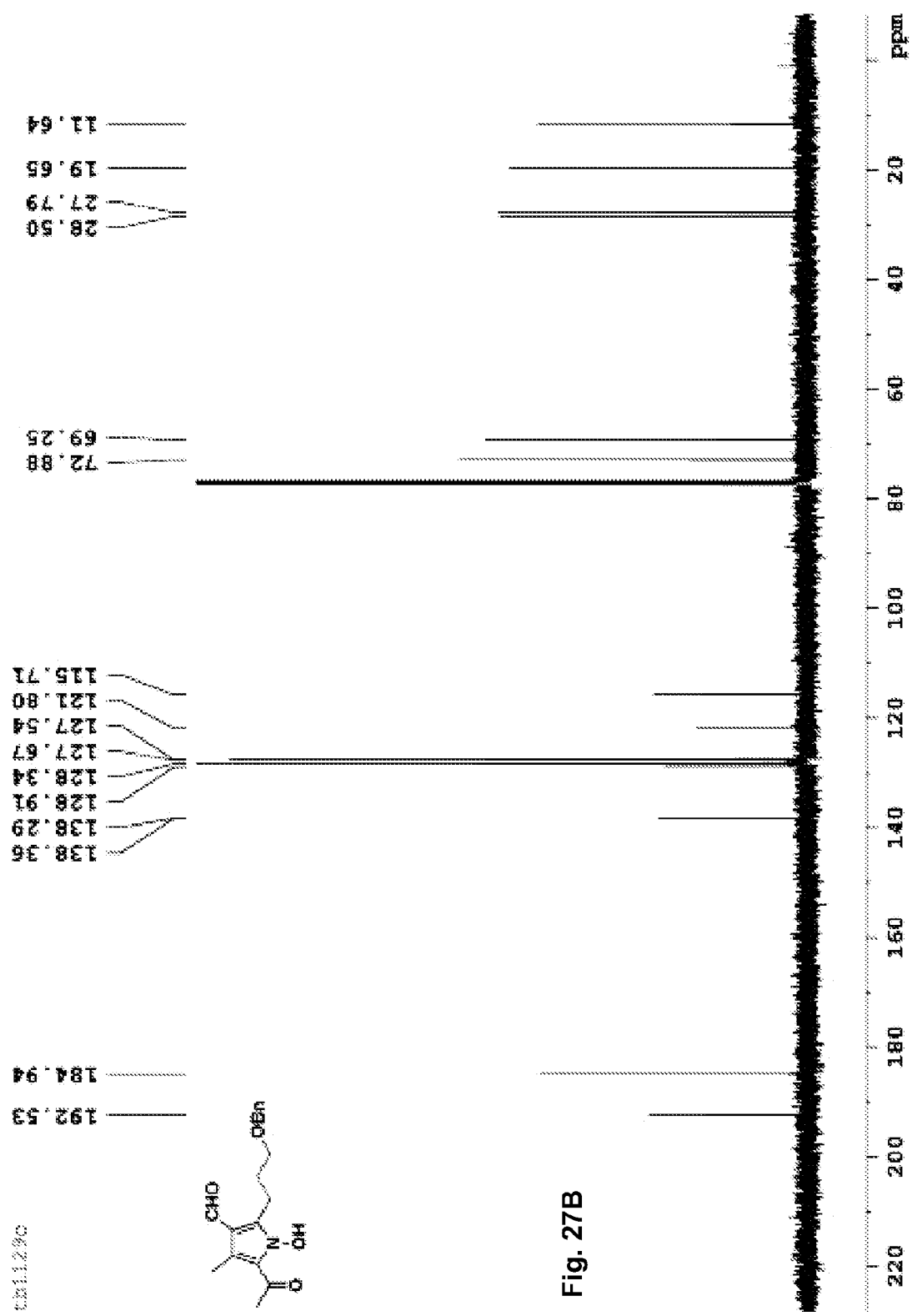
Figure 28A:
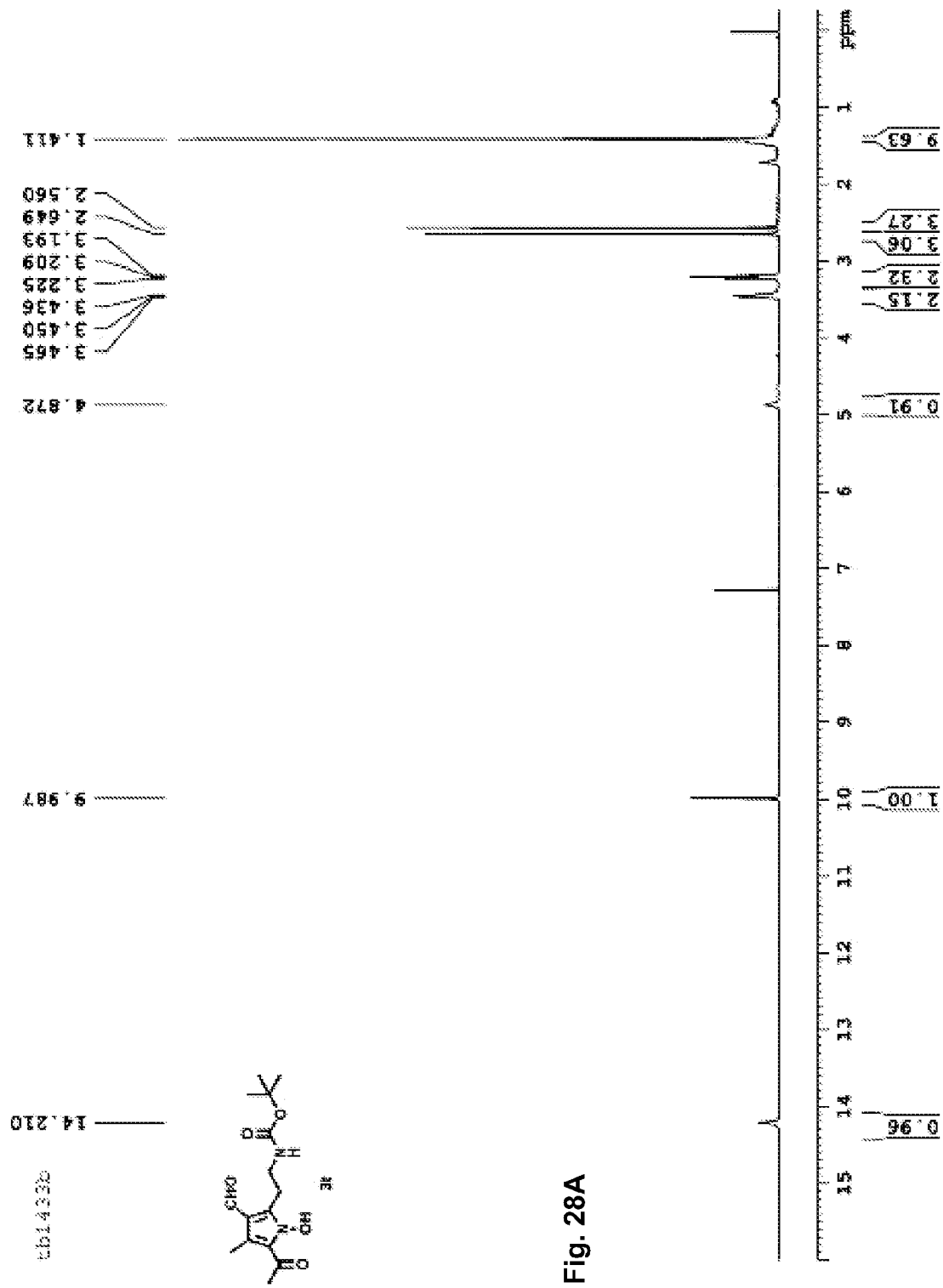
FIG. 28 depicts $^1$H NMR (A) and $^{13}$C NMR (B) spectra of compound 3t.
Figure 28B:
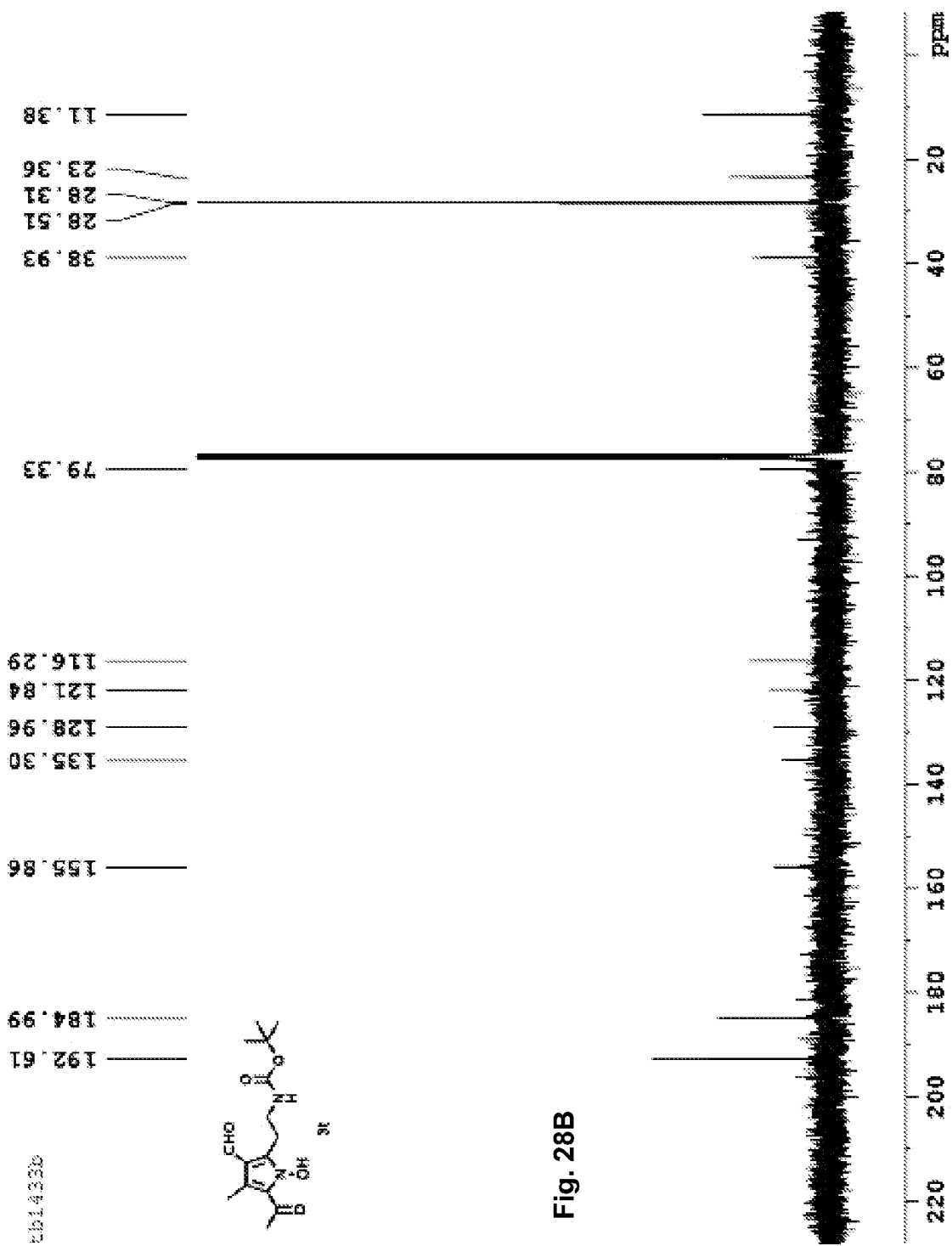
Figure 29A:
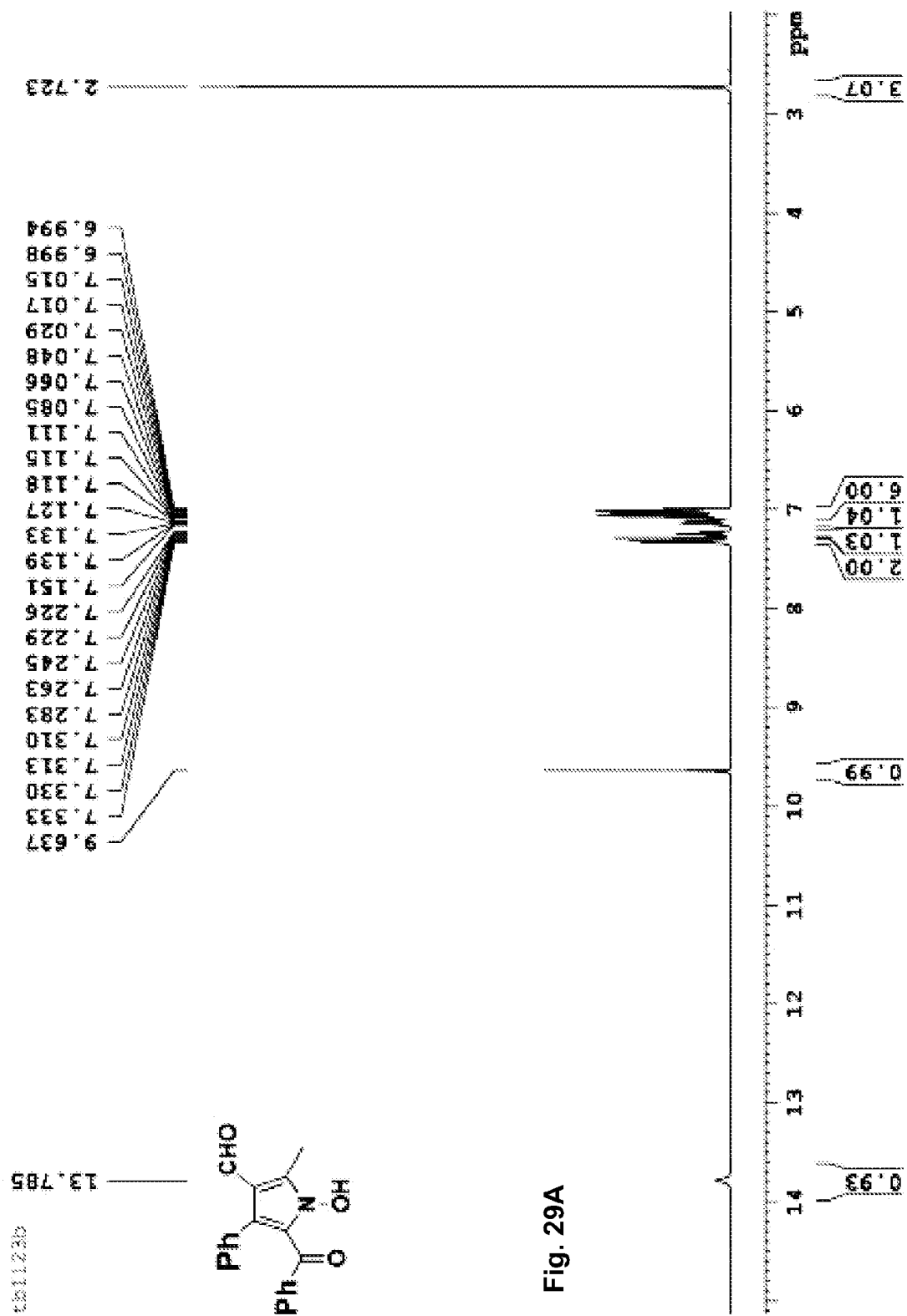
FIG. 29 depicts $^1$H NMR (A) and $^{13}$C NMR (B) spectra of compound 3u.
Figure 29B:
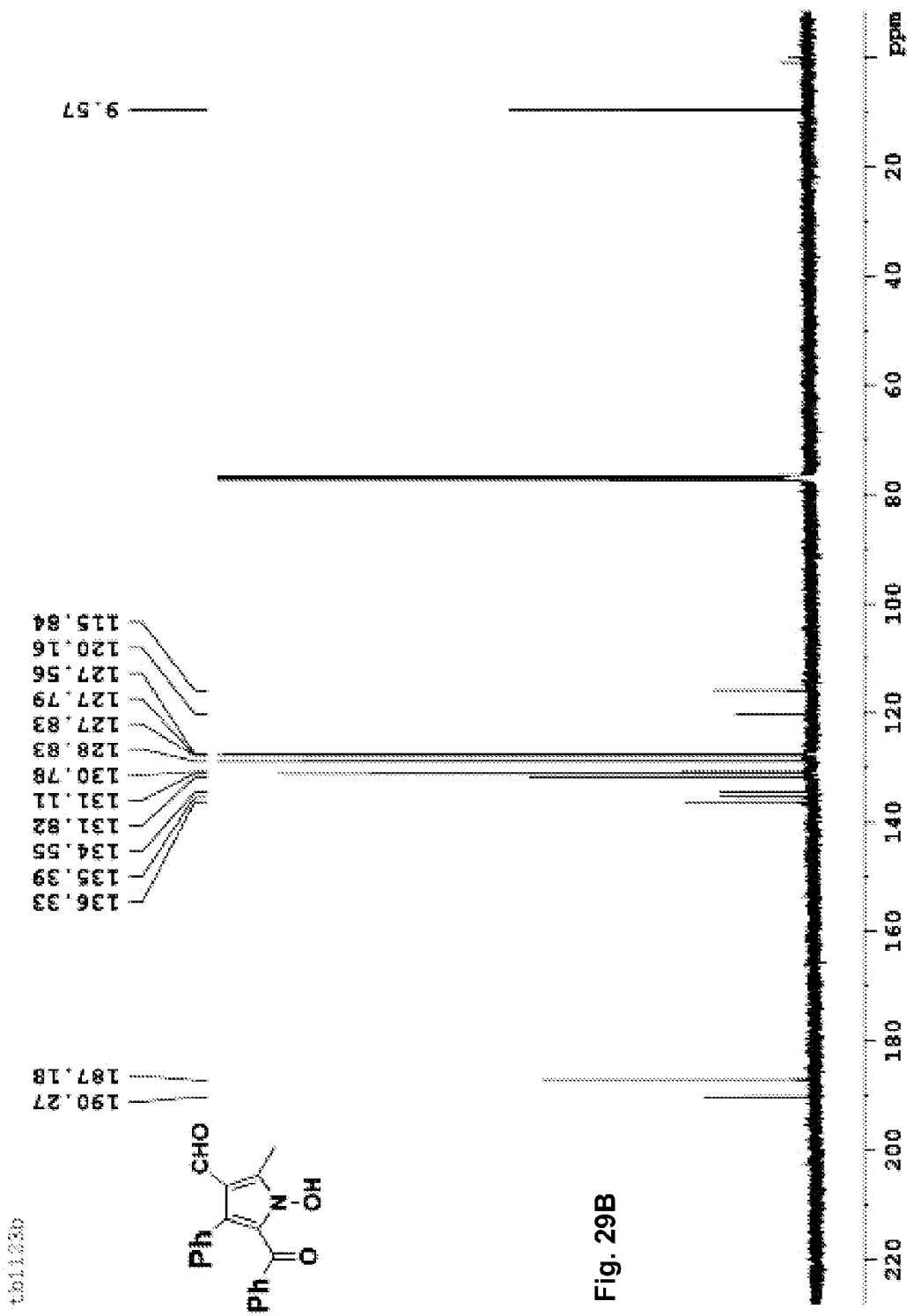
Figure 30A:
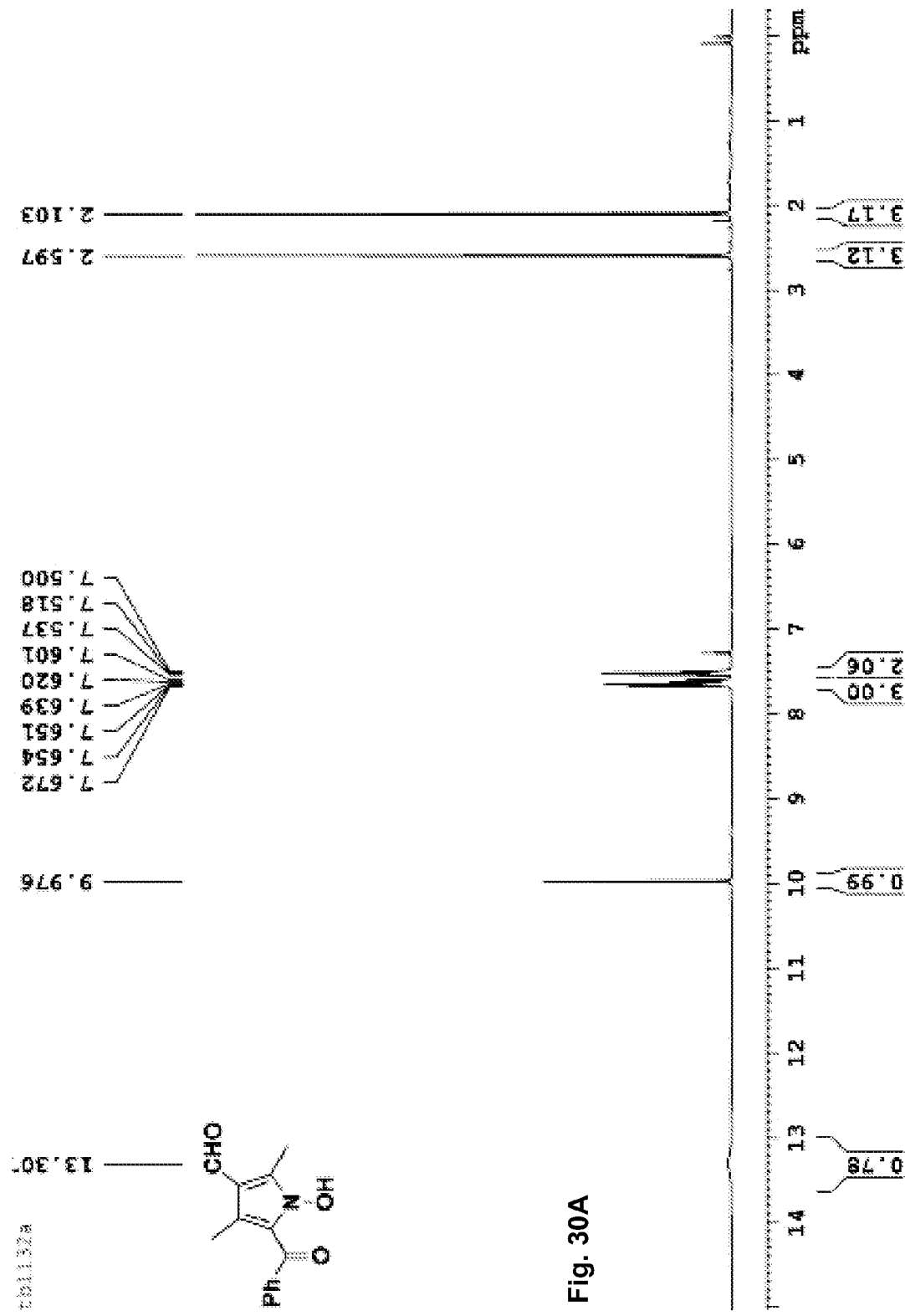
Figure 30B:
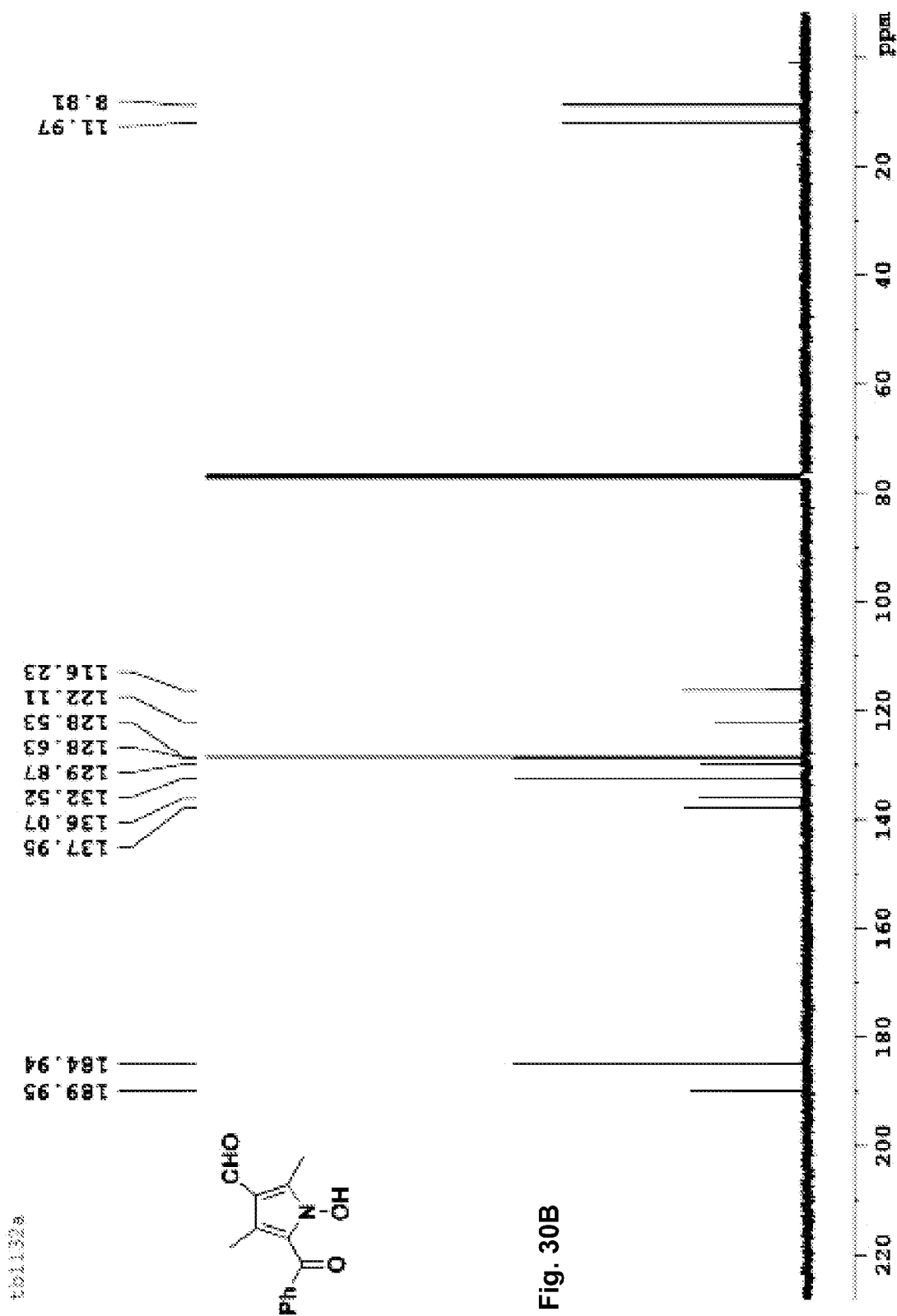
Figure 31A:
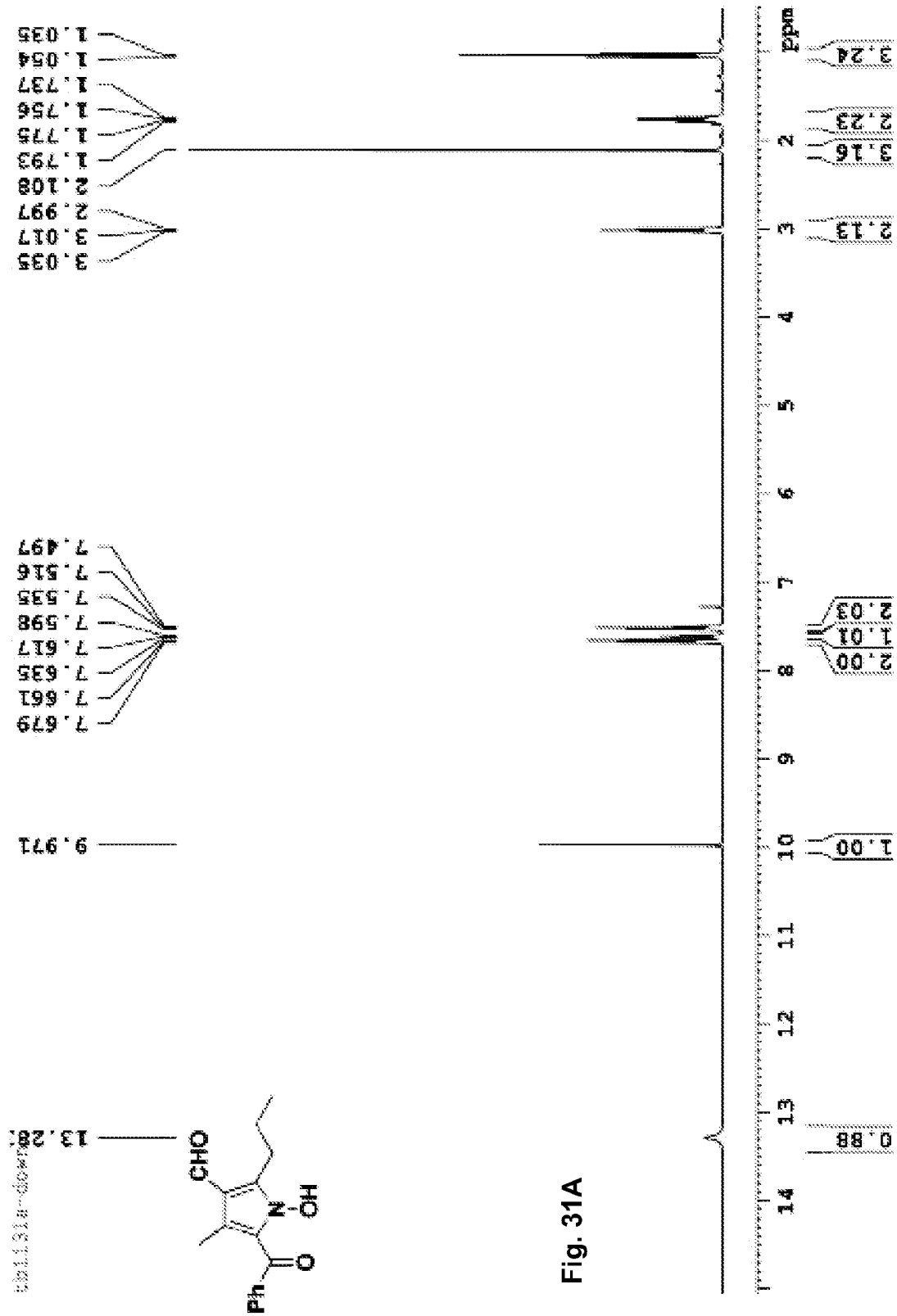
FIG. 31 depicts $^1$H NMR (A) and $^{13}$C NMR (B) spectra of compound 5b.
Figure 31B:
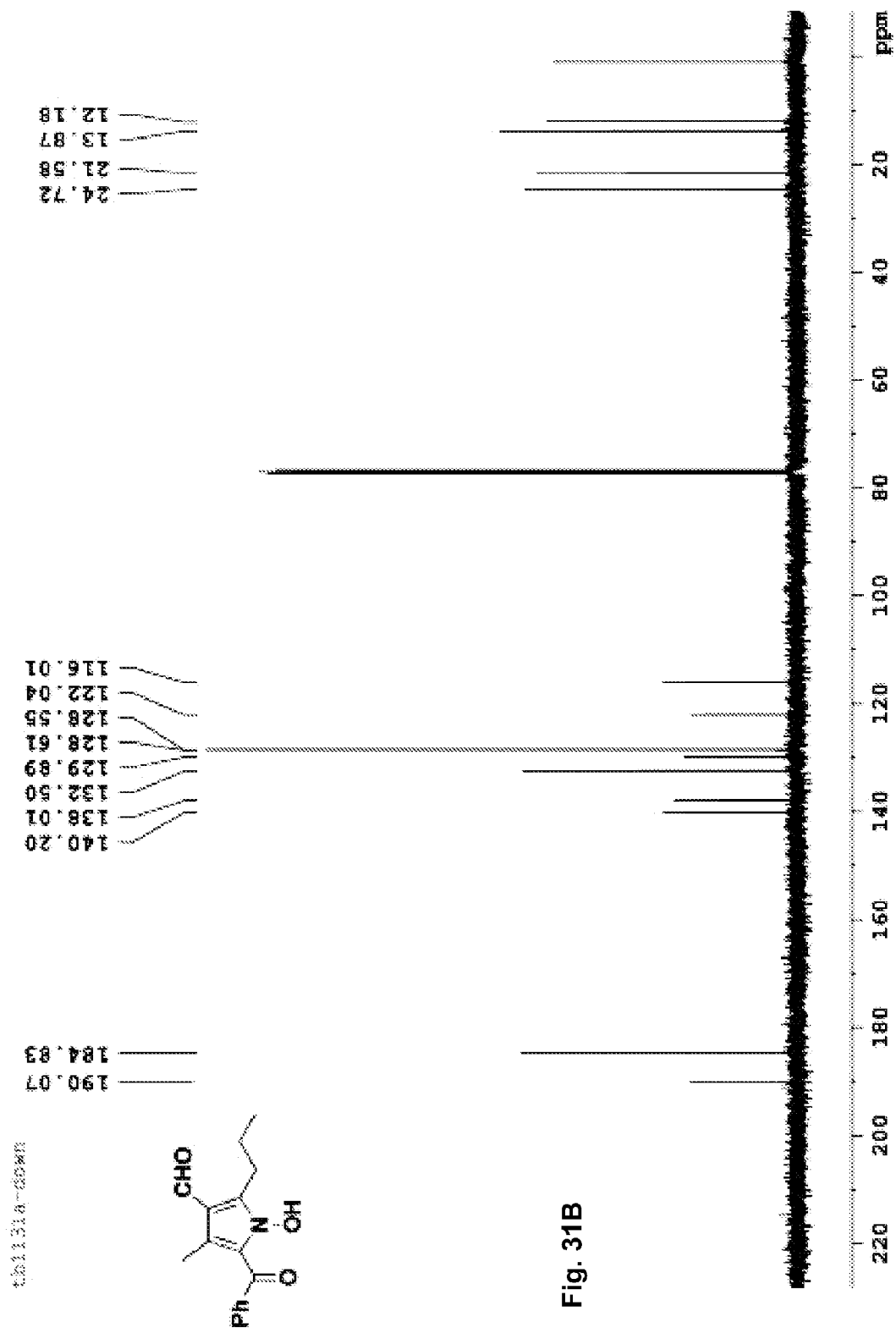
Figure 32A:
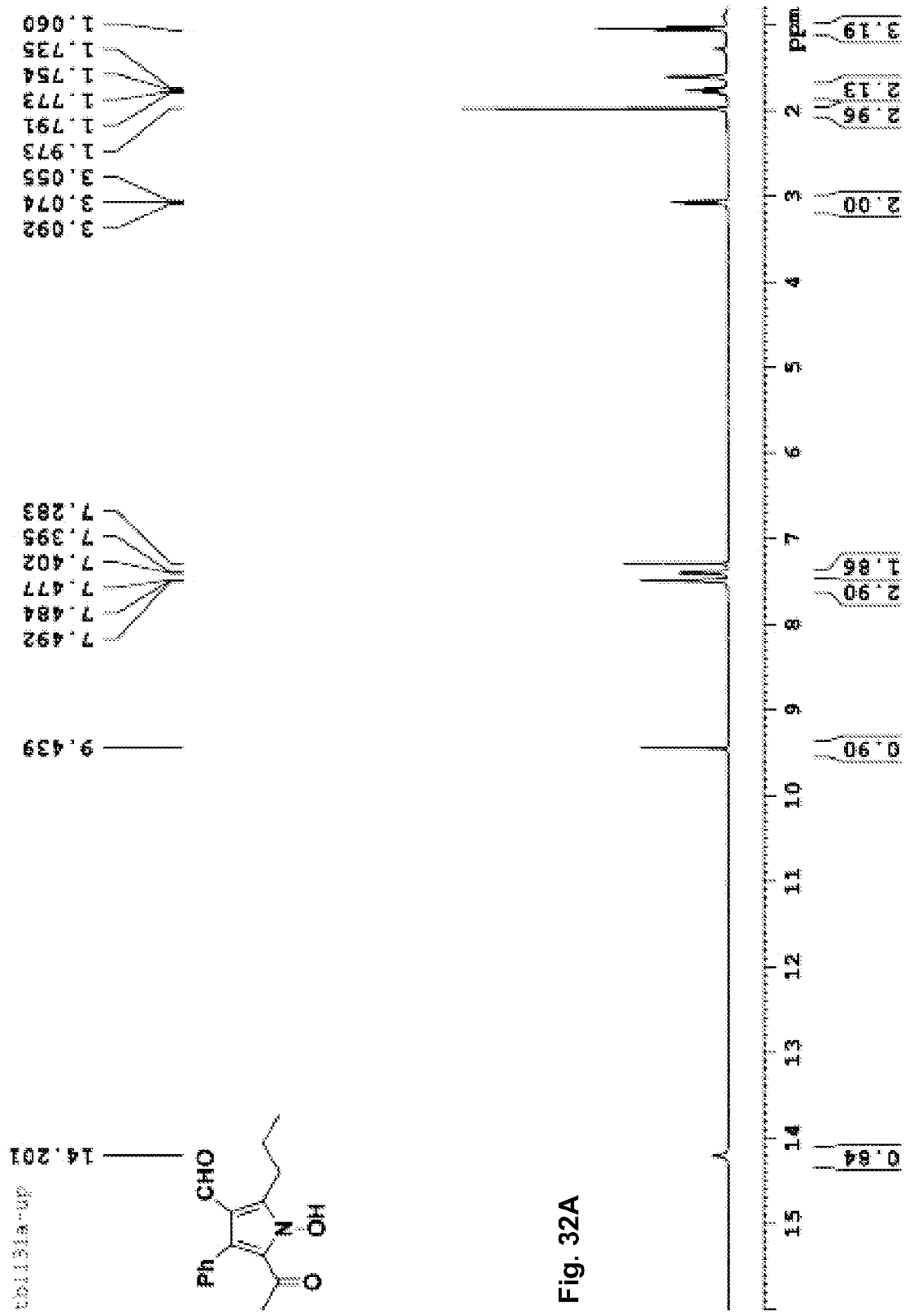
FIG. 32 depicts $^1$H NMR (A) and $^{13}$C NMR (B) spectra of compound 6b.
Figure 32B:
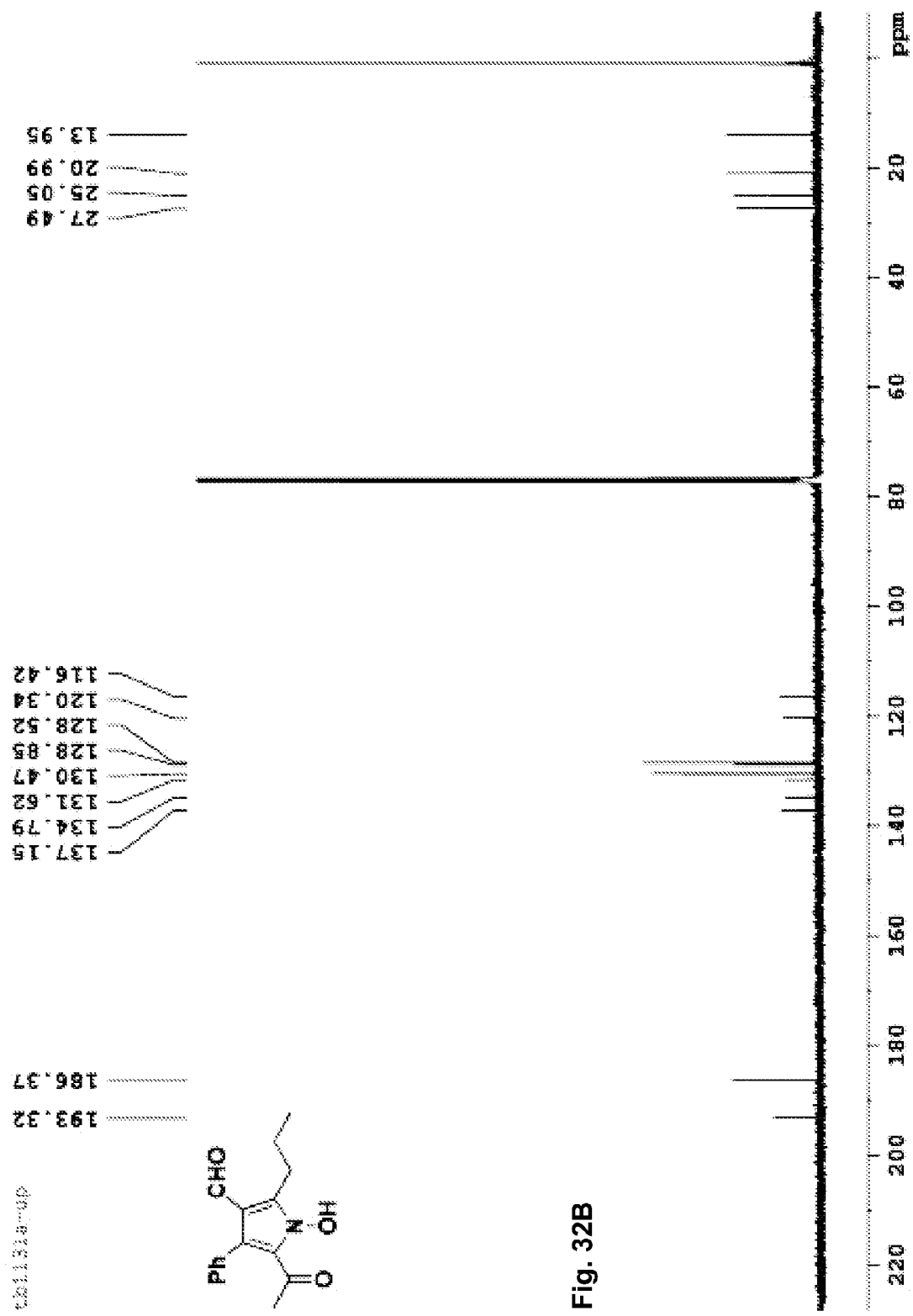
Figure 33A:
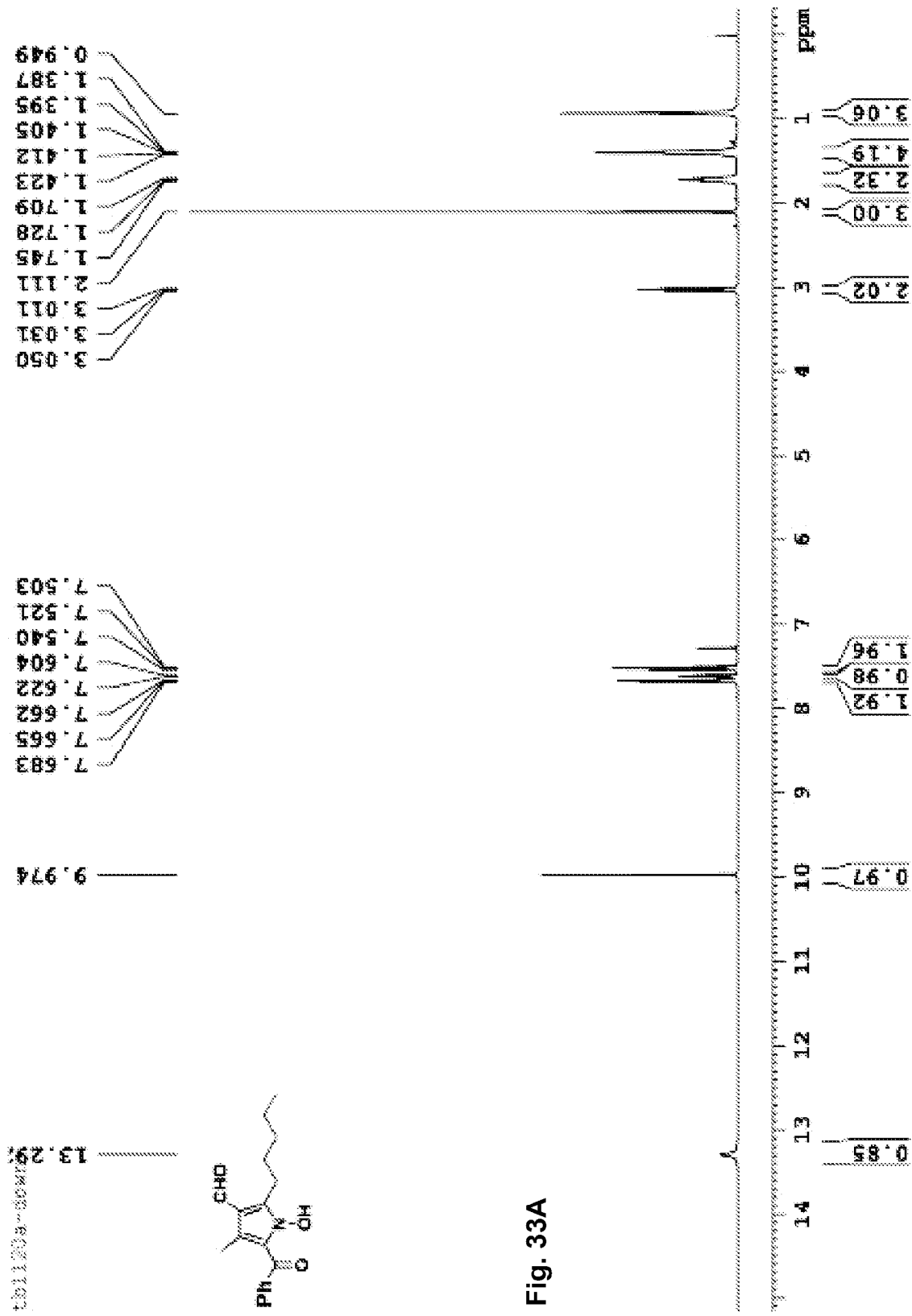
FIG. 33 depicts $^1$H NMR (A) and $^{13}$C NMR (B) spectra of compound 5c.
Figure 33B:
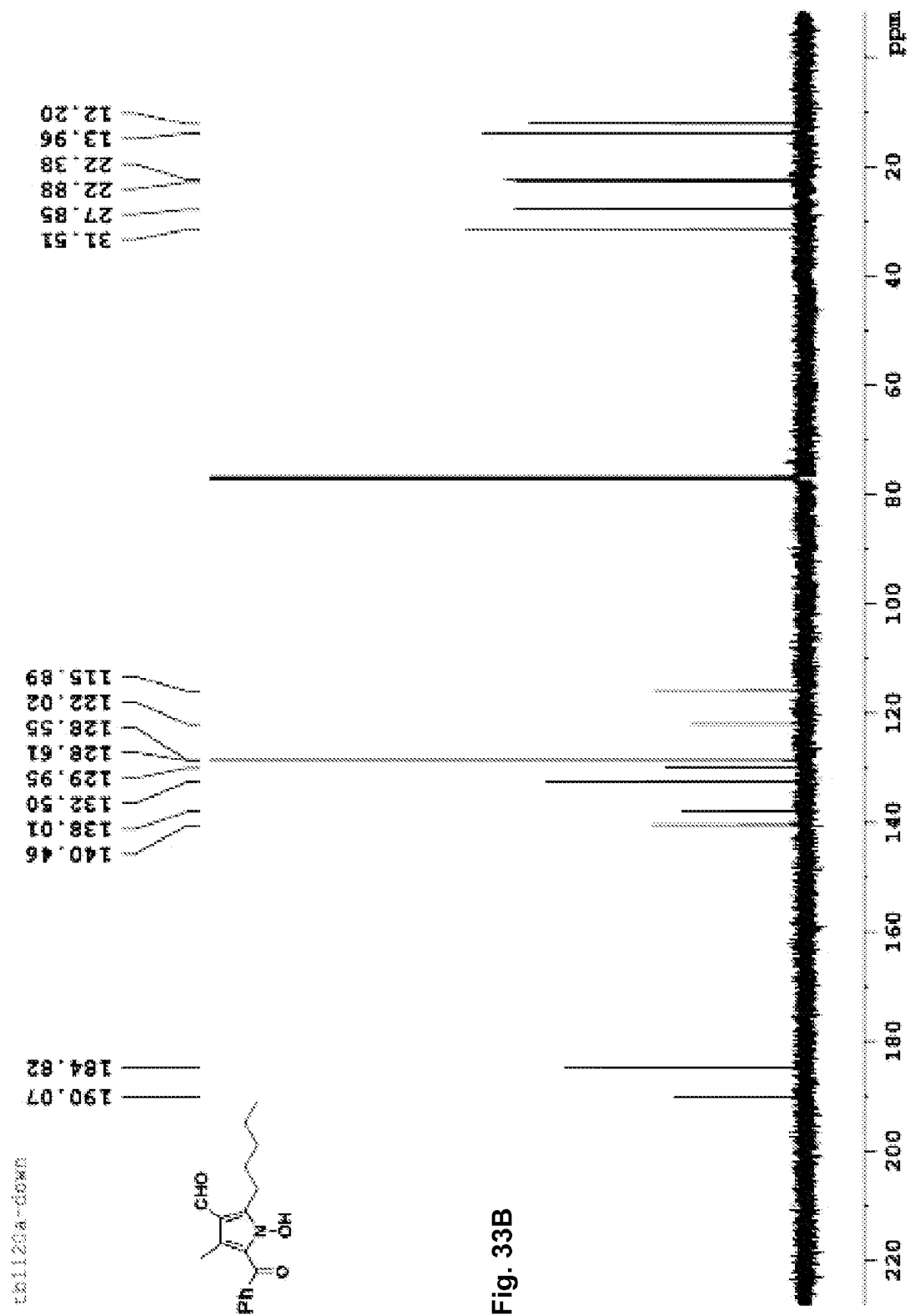
Figure 34A:
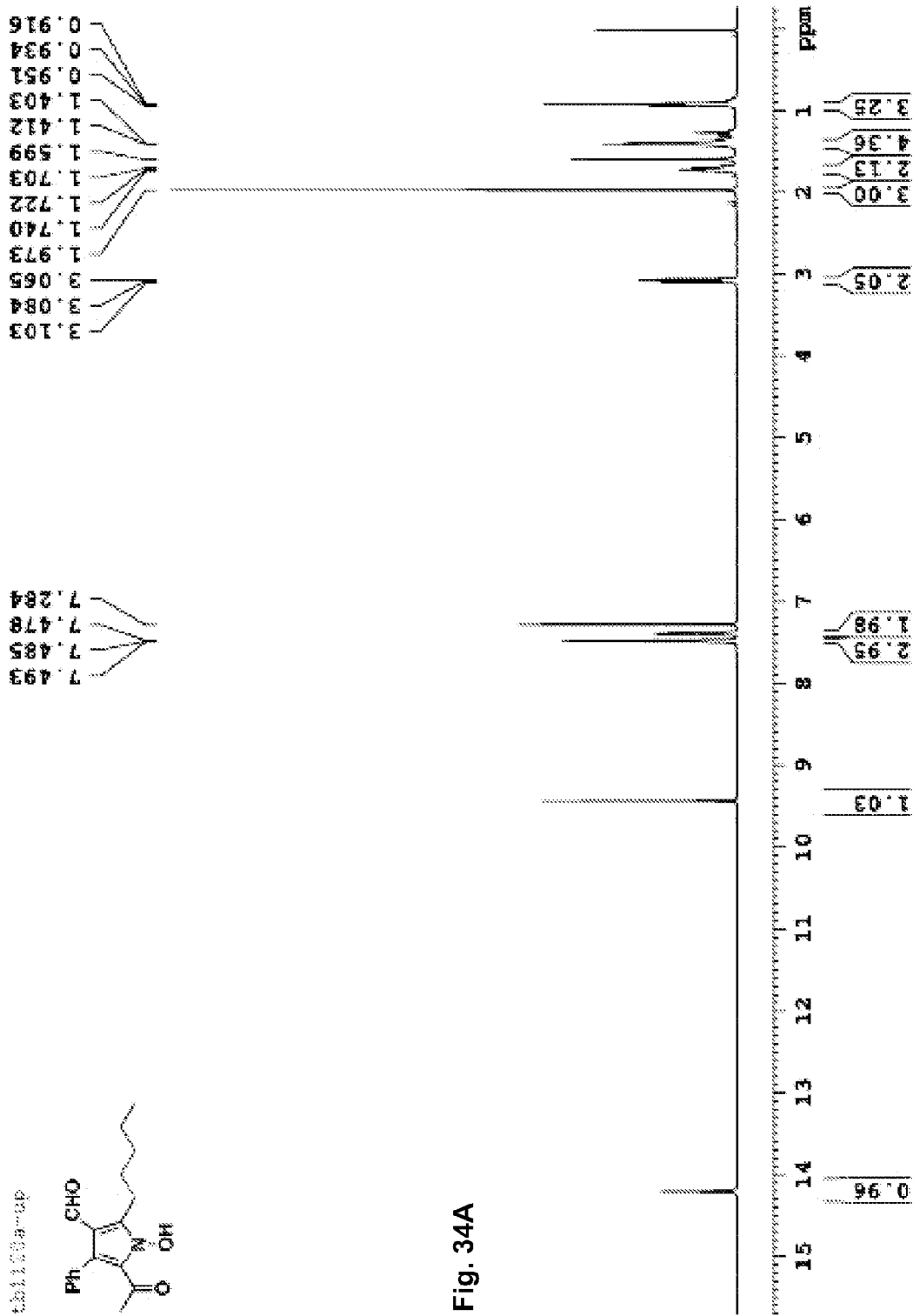
FIG. 34 depicts $^1$H NMR (A) and $^{13}$C NMR (B) spectra of compound 6c.
Figure 34B:
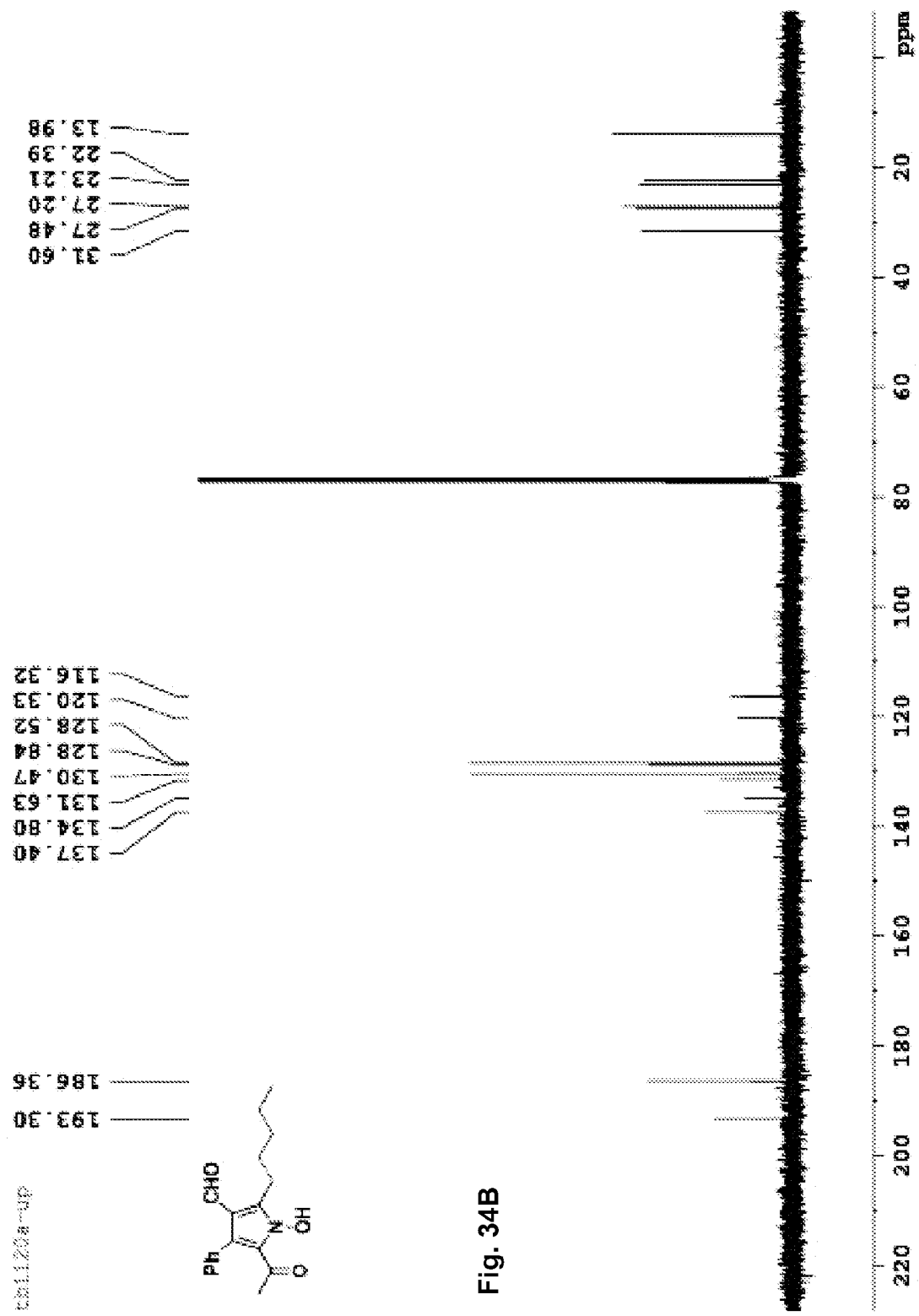
Figure 35A:
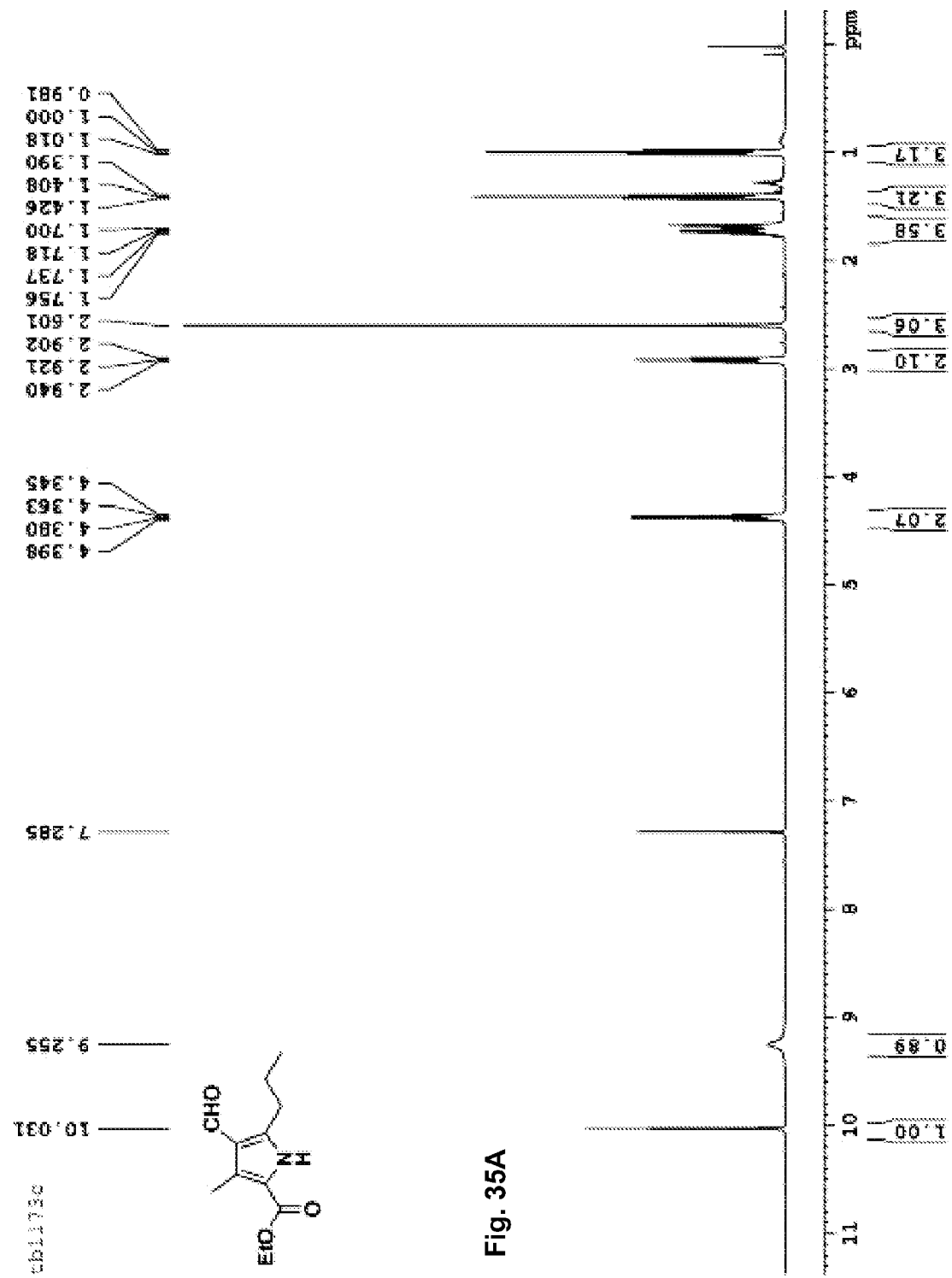
FIG. 35 depicts $^1$H NMR (A) and $^{13}$C NMR (B) spectra of ethyl-4-formyl-3-methyl-5-propyl-1H-pyrrole-2-carboxylate (reduction product of 3a).
Figure 35B:
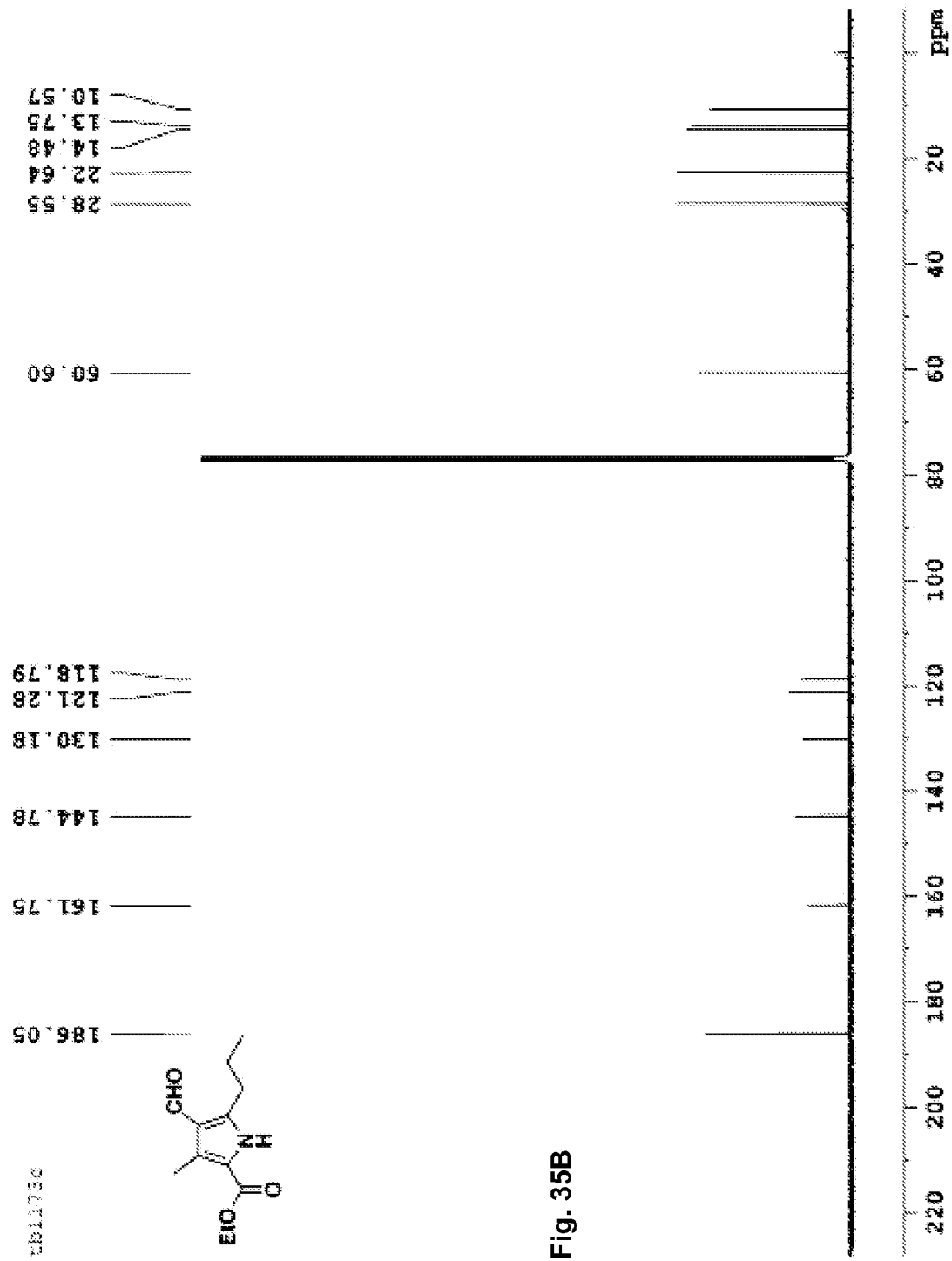
Figure 36A:
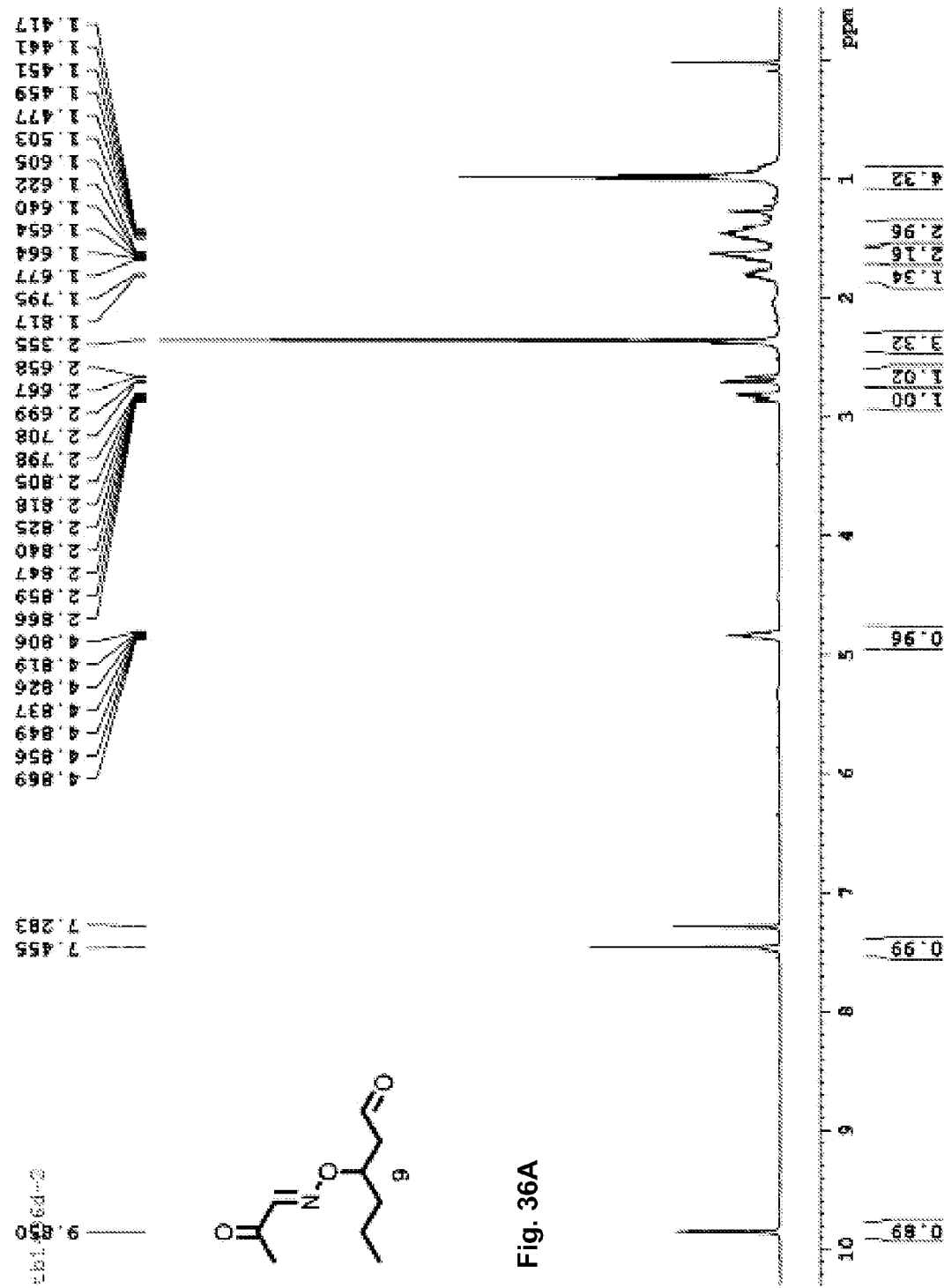
FIG. 36 depicts $^1$H NMR (A) and $^{13}$C NMR (B) spectra of (E)-3-(2-oxopropylidene-aminooxy)hexanal (compound 9).
Figure 36B:
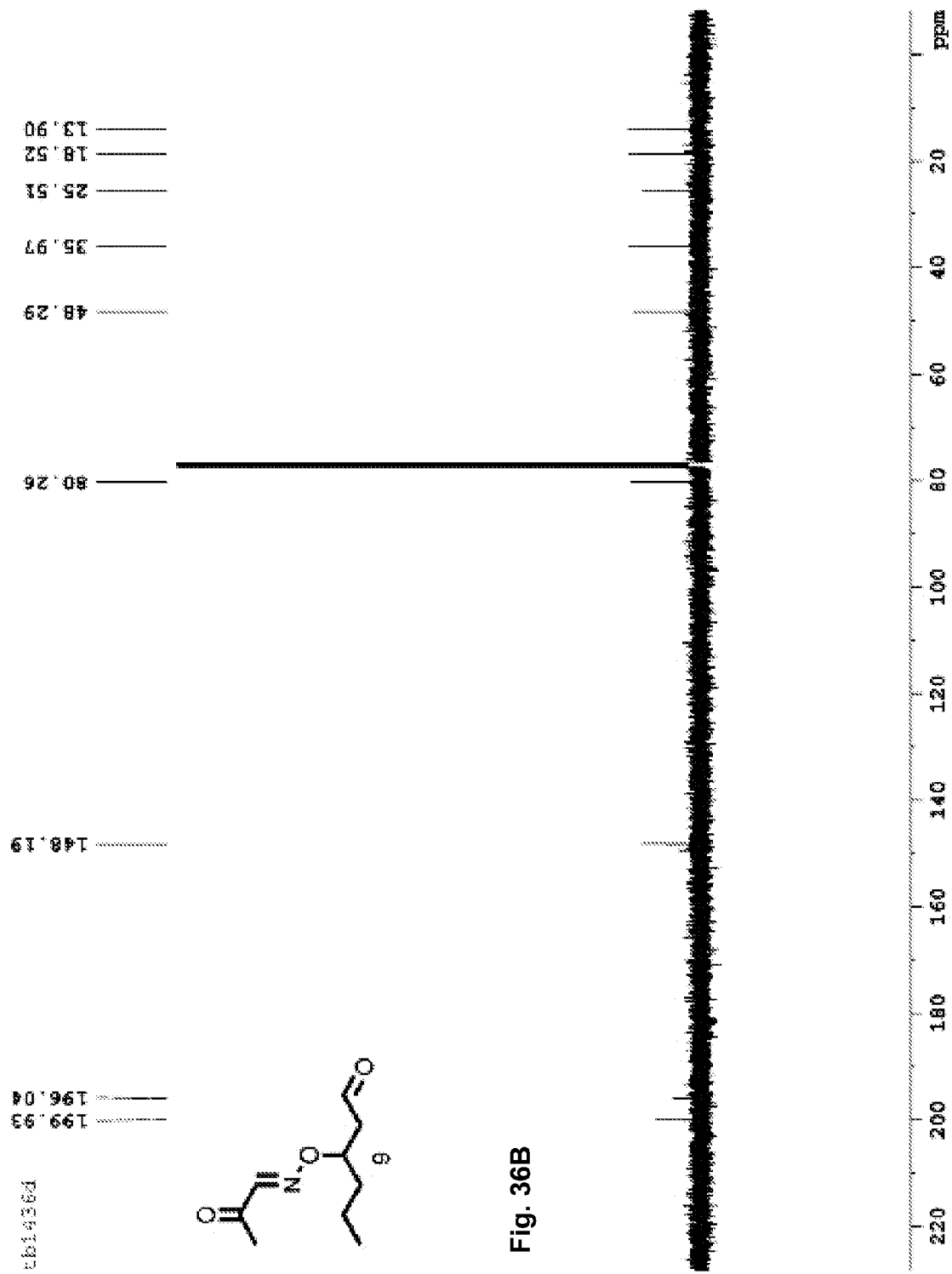
Figure 37A:
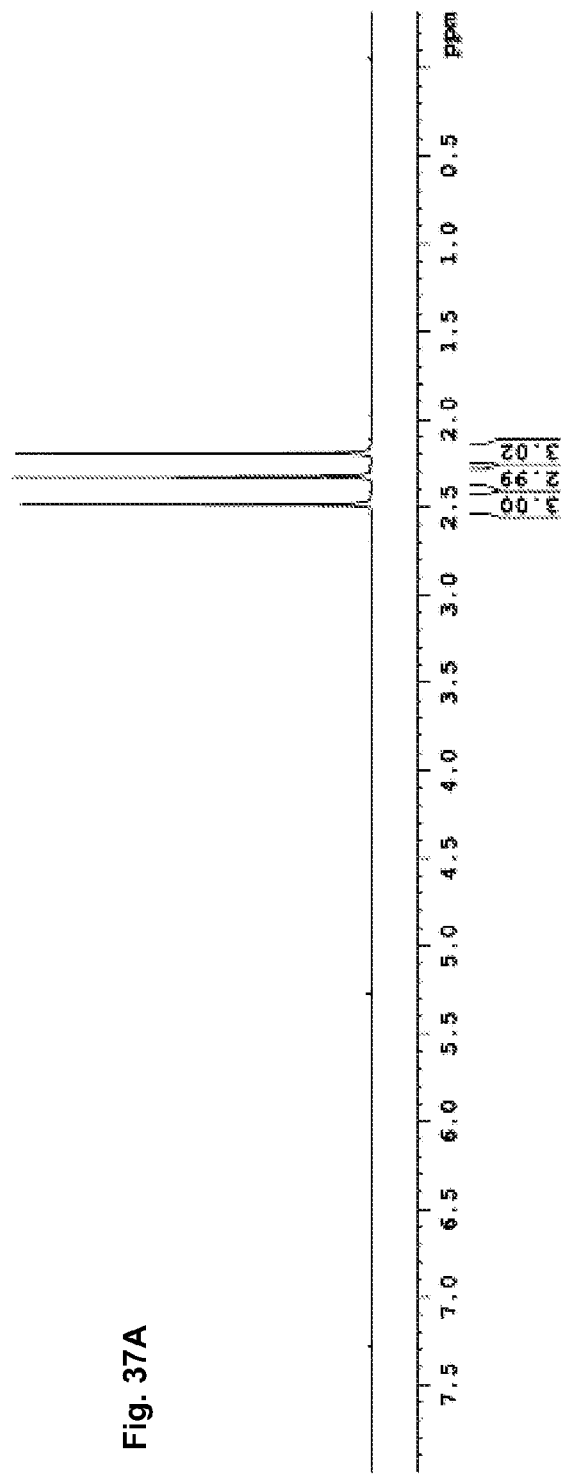
FIG. 37 depicts $^1$H NMR (A) and $^{13}$C NMR (B) spectra of 3-(acetoxyimino)pentane-2,4-dionecompound (compound 10).
Figure 37B:
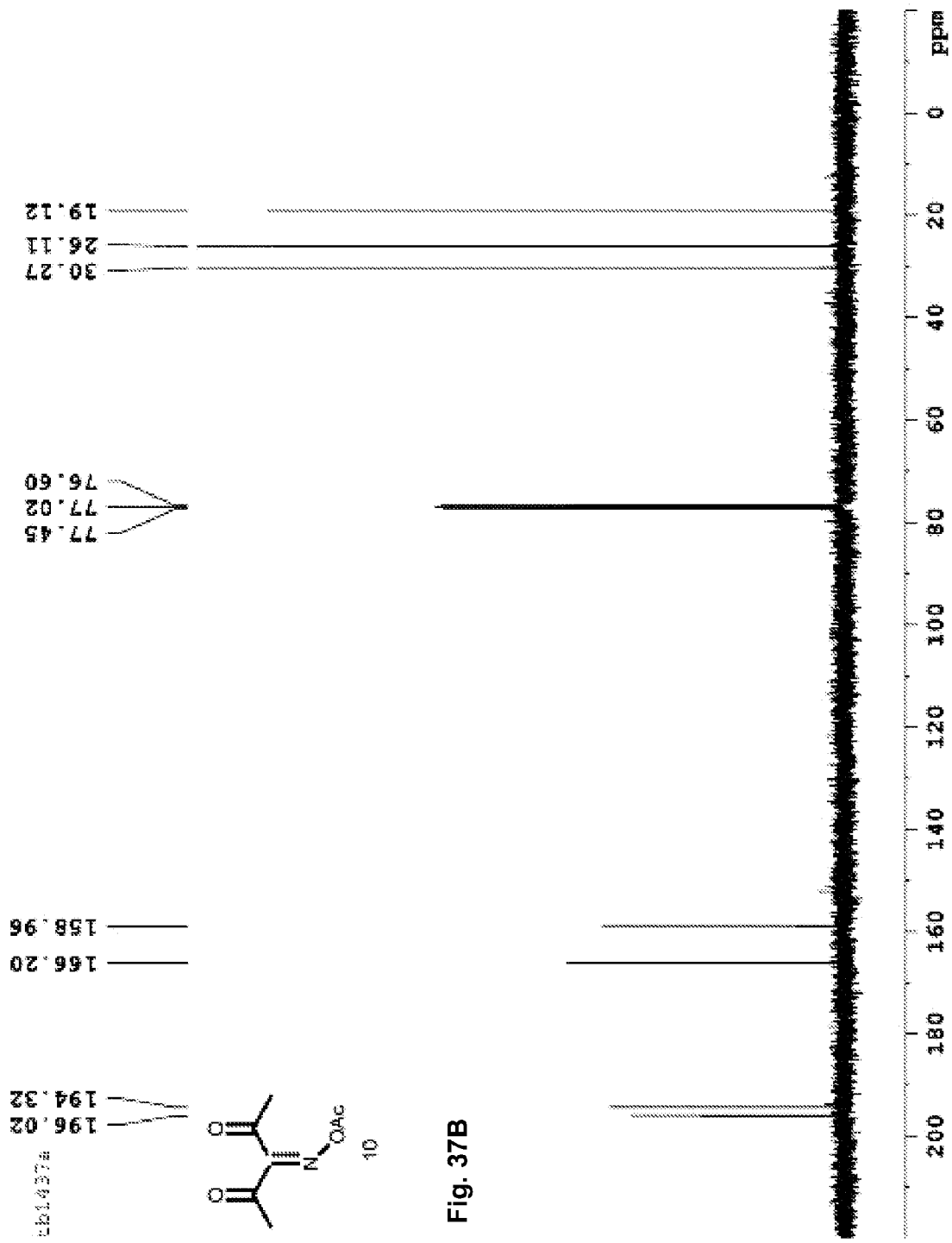
Figure 38A:
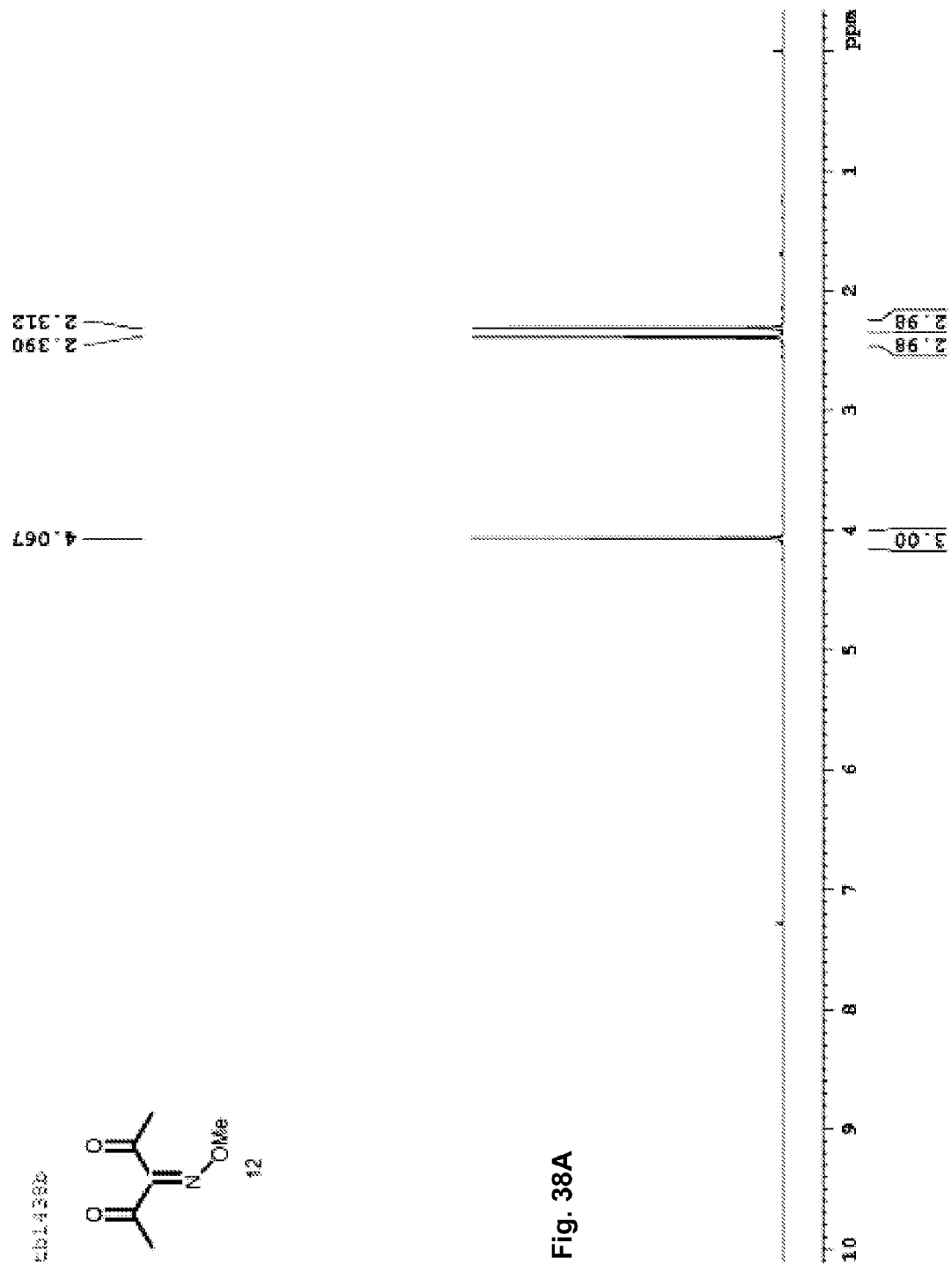
FIG. 38A depicts a $^1$H NMR spectrum and FIG. 38B a $^{13}$C NMR spectrum of 3-(methoxyimino)pentane-2,4-dione (compound 12).
Figure 38B:
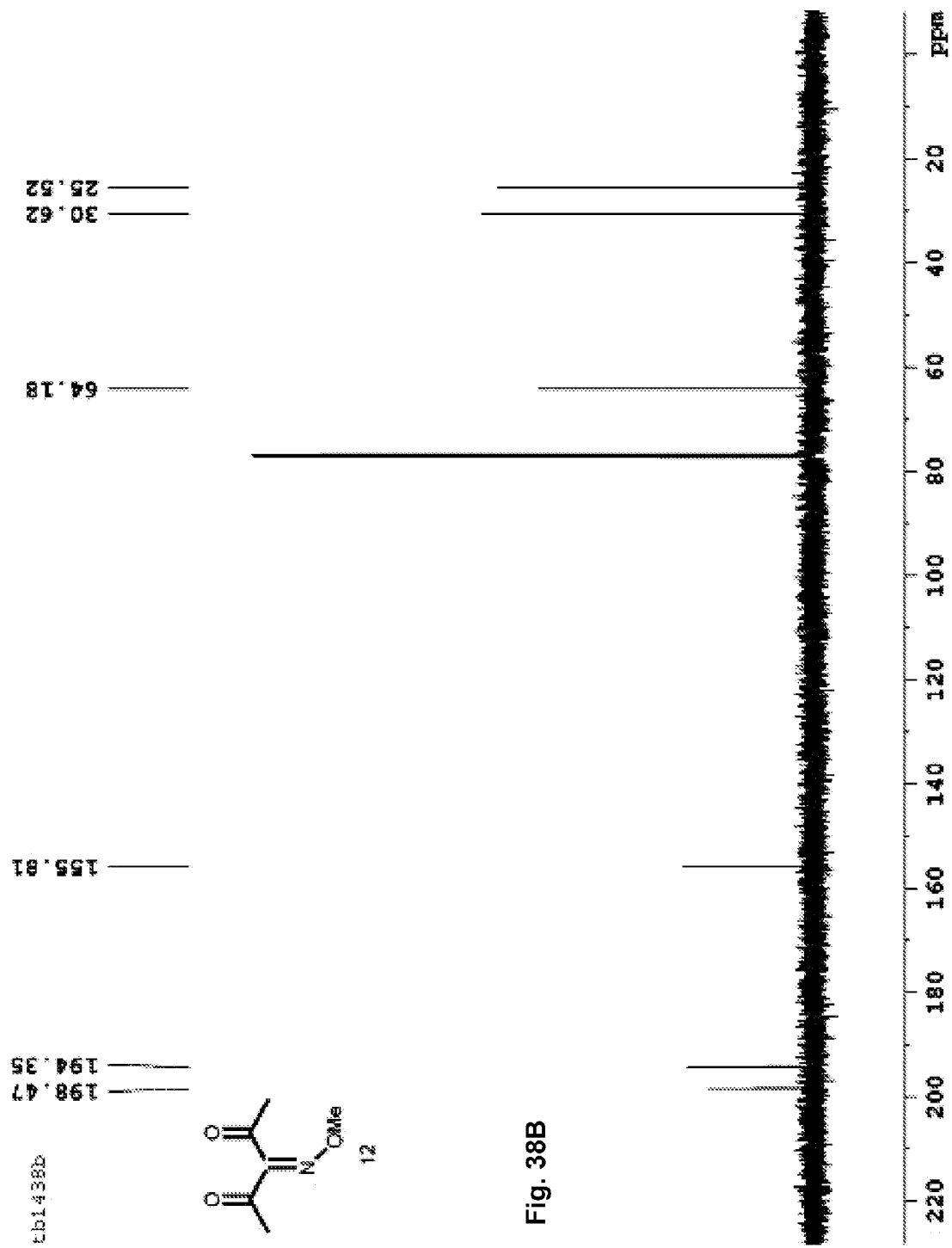

A possible explanation as to why the unusual N-selective Michael products were obtained from the above reaction protocol is attributed to the different substrate structures. The ability of the dicarbonyl oxime to form an intramolecular hydrogen bond (FIG. 9A). The intramolecular hydrogen bond could decrease the nucleophilicity of the oxime oxygen, thus increasing the nucleophilicity of the oxime nitrogen and resulting in N-selectivity. Based on the above deduction, some control experiments were carried out.

Mechanism Investigation (Control Experiments)
O-Selective Michael Addition of Enal

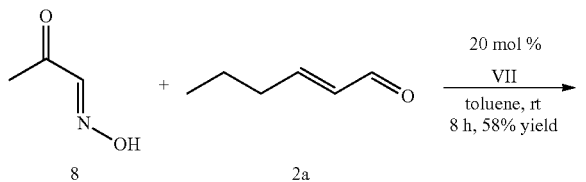

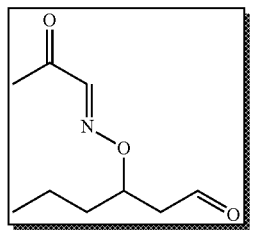

(E)-3-(2-Oxopropylideneaminooxy)hexanal (9)

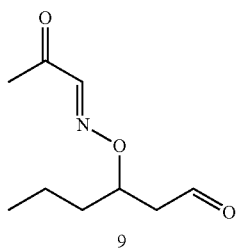

To a solution of oxime compound 8 (0.2 mmol, 1.0 eq) and (E)-hex-2-enal 2a (0.5 mmol, 2.5 eq) in toluene (1 mL) was added catalyst VII (0.04 mmol, 0.2 eq) at room temperature. The resulting mixture was stirred vigorously. After 8 hours, the product 9 was afforded by flash chromatography over silica gel (EtOAc/Hexane=1:10) in 58% yield.

$^1$H-NMR (400 MHz, CDCl$_3$): δ 9.85 (s, 1H), 7.45 (m, 2H), 4.87-4.81 (m, 1H), 2.86 (dd, J=7.6, 16.8 Hz, 1H), 2.66 (dd, J=3.6, 16.8 Hz, 1H), 2.36 (s, 3H), 1.82-1.71 (m, 1H), 1.68-1.61 (m, 2H), 1.50-1.42 (m, 2H), 0.98 (t, J=7.2 Hz, 3H).

$^{13}$C-NMR (100 MHz, CDCl$_3$): δ 199.9, 196.0, 148.2, 80.3, 48.3, 36.0, 25.5, 18.5, 13.9.

Synthesis of 3-(acetoxyimino)pentane-2,4-dione (10)

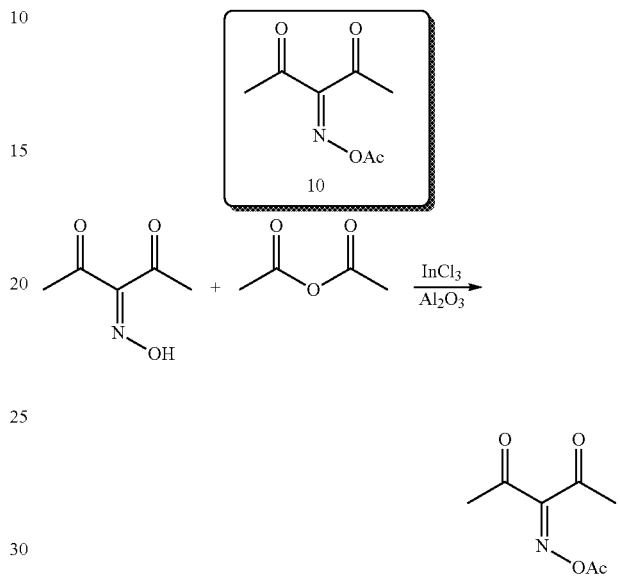

To a solution of oxime compound (5 mmol) and acetic anhydride (1 mL) was added catalyst InCl$_3$ (1.0 mmol, 0.2 eq) and Al$_2$O$_3$ (0.5 g) at room temperature. The resulting mixture was stirred vigorously for 8 hours. The product 10 was afforded by flash chromatography over silica gel (EtOAc/Hexane=1:8) in 62% yield.

$^1$H-NMR (400 MHz, CDCl$_3$): δ 2.48 (s, 3H), 2.33 (s, 3H), 2.20 (s, 3H).

$^{13}$C-NMR (100 MHz, CDCl$_3$): δ 13C-NMR (100 MHz, CDCl$_3$): δ 196.0, 194.3, 166.2, 159.0, 30.3, 26.1, 19.1.

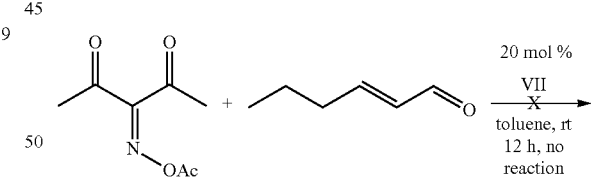

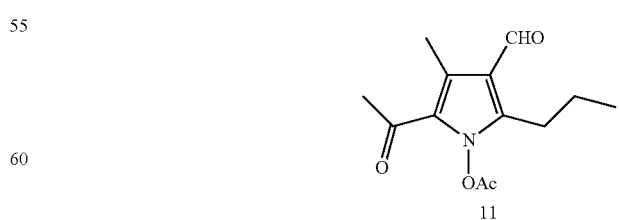

To a solution of 3-(acetoxyimino)pentane-2,4-dione 10 (0.2 mmol, 1.0 eq) and (E)-hex-2-enal (0.5 mmol, 2.5 eq) in toluene (0.8 mL) was added catalyst VII (0.04 mmol, 0.2 eq)

in toluene (0.2 mL) at room temperature. The resulting mixture was stirred vigorously. After 12 hours the reaction still didn't proceed.

3-(Methoxyimino)pentane-2,4-dione (12)

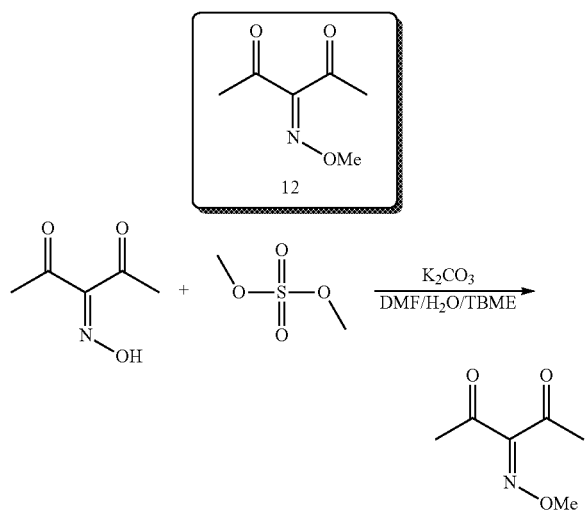

Oxime compound (5 mmol) and dimethyl sulfate (5 mmol) was dissolved in DMF (5 mL), H$_2$O (1 mL) and tert-Butyl methyl ether (4 mL), and then added K$_2$CO$_3$ (7.0 mmol) at room temperature. The resulting mixture was stirred vigorously for 12 hours. The product 10 was afforded by flash chromatography over silica gel (EtOAc/Hexane=1:10) in 95% yield.

$^1$H-NMR (400 MHz, CDCl$_3$): δ 4.07 (s, 3H), 2.39 (s, 3H), 2.31 (s, 3H).

$^{13}$C-NMR (100 MHz, CDCl$_3$): δ 198.5, 194.3, 155.8, 64.2, 30.6, 25.5.

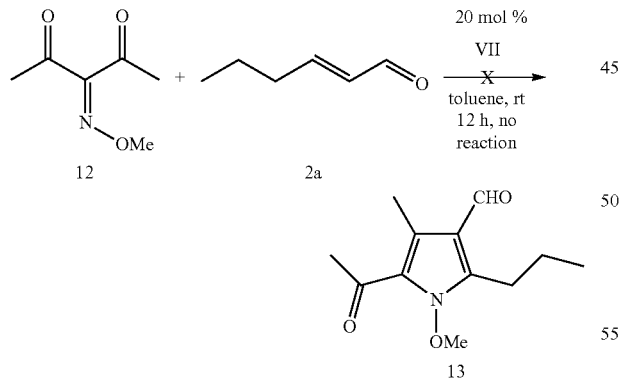

To a solution of 3-(acetoxyimino)pentane-2,4-dione 12 (0.2 mmol, 1.0 eq) and (E)-hex-2-enal (0.5 mmol, 2.5 eq) in toluene (0.8 mL) was added catalyst VII (0.04 mmol, 0.2 eq) in toluene (0.2 mL) at room temperature. The resulting mixture was stirred vigorously. After 12 hours the reaction still didn't proceed.

(E)-Oxime 8 afforded exclusively the O-selective Michael adduct, which supported the above hypothesis as 8 was unable to form intramolecular hydrogen bonds. Furthermore, when acetyl or methyl-protected oxime 11 or 13 was used in this reaction, the reaction did not proceed at all (FIG. 9B), which further strengthened the conjecture that the intramolecular hydrogen bond is the main driving force for producing N-selective products.

In summary, a facile and efficient one-pot synthesis of polyfunctionalized N-hydroxy-pyrroles has been developed, using readily available carbonyl oximes and α,β-unsaturated aldehydes. This synthesis involves sequential Michael addition, intramolecular aldol condensation, and aromatization reactions through iminium activation of α,β-unsaturated aldehydes by diisopropylamine. In the domino synthesis, carbonyl oximes acted as unusual N-selective nucleophiles in the Michael addition reaction. This method employed readily available starting materials and mild conditions, and proceeded in good yields with wide substrate scope, high regioselectivity, and flexible substitution patterns, affording products with great synthetic potential. Future studies will entail expansion of the scope and applications of these powerful domino processes.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of forming a pyrrole compound comprising:
contacting an α-carbonyl oxime compound 1

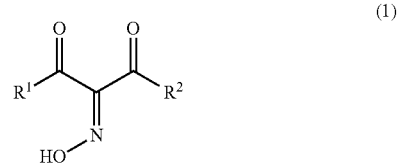

wherein R$^1$ and R$^2$ are independently selected from the group consisting of H, a silyl-group, an aliphatic group, an alicyclic group, an aromatic group, an arylaliphatic group, an arylalicyclic group, the group —$OR^{10}$ and the group —$NR^{10}$, wherein each moiety $R^{10}$ is independently selected from the group consisting of H, a silyl-group, an aliphatic group, an alicyclic group, an aromatic group, an arylaliphatic group, and an arylalicyclic group, the aliphatic, alicyclic, aromatic, arylaliphatic, and arylalicyclic groups comprised in $R^1$, $R^2$, and $R^{10}$ comprising 0 to about 3 heteroatoms selected from the group N, O, S, Se and Si, and an α,β-unsaturated aldehyde 2,

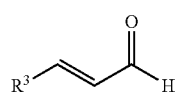

(2)

wherein $R^3$ is selected from the group consisting of H, a silyl-group, an aliphatic group, and an alicyclic group, the aliphatic and alicyclic groups comprising 0 to about 3 heteroatoms selected from the group N, O, S, Se and Si, in the presence of a secondary amine in a suitable solvent for a sufficient period of time to allow the formation of an N-hydroxypyrrole compound 3,

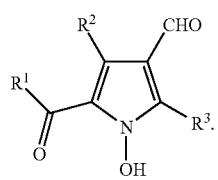

(3)

2. The process of claim 1, wherein the secondary amine is present in a catalytic amount.

3. The process of claim 1, comprising:
adding the α-carbonyl oxime compound 1 and the α,β-unsaturated aldehyde 2 to the suitable solvent, thereby forming a first solution,
adding to the first solution the secondary amine, thereby forming a second solution, and
allowing the formation of the N-hydroxypyrrole compound 3 in the second solution.

4. The process of claim 1, wherein the secondary amine is of general formula XX

(XX)

wherein $R^{20}$ and $R^{21}$ are independently selected from the group consisting of an aliphatic group, an alicyclic group, an aromatic group, an arylaliphatic group and an arylalicyclic group, comprising 0 to about 3 heteroatoms selected from the group N, O, S, Se and Si.

5. The process of claim 1, further comprising reducing N-hydroxypyrrole compound 3 to 1H-pyrrole compound 7

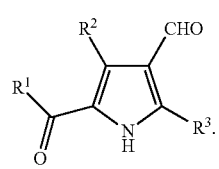

(7)

6. The process of claim 5, wherein reducing N-hydroxypyrrole compound 3 comprises contacting the same with a metal in the presence of a surfactant.

7. The process of claim 1, wherein contacting the α-carbonyl oxime compound 1 and the α,β-unsaturated aldehyde 2 is carried out at a temperature selected in the range from about −20° C. to about 60° C.

8. The process of claim 1, wherein contacting the α-carbonyl oxime compound 1 and the α,β-unsaturated aldehyde 2 is carried out at ambient temperature.

9. The process of claim 1, wherein the α-carbonyl oxime compound 1 and the α,β-unsaturated aldehyde 2 are contacted for a period of time selected in the range from about 8 to about 48 hours.

10. The process of claim 1, wherein the solvent is an aqueous liquid.

11. The process of claim 1, wherein the α-carbonyl oxime compound 1 is formed from (i) a 1,3-dicarbonyl compound 20

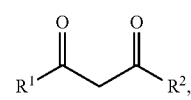

(20)

and (ii) an inorganic nitrite in a carboxylic acid solvent.

12. The process of claim 11, wherein the α-carbonyl oxime compound 1 is formed in situ from the 1,3-dicarbonyl compound 20.

13. The process of claim 12, comprising:
forming the α-carbonyl oxime compound 1 from the 1,3-dicarbonyl compound 20 and an inorganic nitrite in a carboxylic acid solvent,
adding the α,β-unsaturated aldehyde 2, thereby forming a first solution,
adding to the first solution the secondary amine, thereby forming a second solution, and
allowing the formation of the N-hydroxypyrrole compound 3 in the second solution.

* * * * *